(12) United States Patent
Alam et al.

(10) Patent No.: US 11,077,108 B2
(45) Date of Patent: Aug. 3, 2021

(54) ALLOSTERIC CORTICOTROPIN-RELEASING FACTOR RECEPTOR 1 (CRFR1) ANTAGONISTS THAT DECREASE P-TAU AND IMPROVE COGNITION

(71) Applicant: The Regents of the University of California, Oakland, CA (US)

(72) Inventors: Mohammad Parvez Alam, Los Angeles, CA (US); Varghese John, Los Angeles, CA (US); Barbara Jagodzinska, Redwood City, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/330,754

(22) PCT Filed: Sep. 6, 2017

(86) PCT No.: PCT/US2017/050347
§ 371 (c)(1),
(2) Date: Mar. 5, 2019

(87) PCT Pub. No.: WO2018/048953
PCT Pub. Date: Mar. 15, 2018

(65) Prior Publication Data
US 2019/0307747 A1   Oct. 10, 2019

Related U.S. Application Data

(60) Provisional application No. 62/384,656, filed on Sep. 7, 2016.

(51) Int. Cl.
| | |
|---|---|
| *C07D 239/47* | (2006.01) |
| *C07D 239/48* | (2006.01) |
| *A61K 31/506* | (2006.01) |
| *A61P 25/28* | (2006.01) |
| *A61K 9/00* | (2006.01) |
| *C07D 405/12* | (2006.01) |
| *C07D 239/34* | (2006.01) |
| *C07D 403/12* | (2006.01) |
| *C07D 239/52* | (2006.01) |
| *A61K 31/505* | (2006.01) |
| *A61K 45/06* | (2006.01) |

(52) U.S. Cl.
CPC .......... *A61K 31/506* (2013.01); *A61K 9/0053* (2013.01); *A61K 31/505* (2013.01); *A61P 25/28* (2018.01); *C07D 239/34* (2013.01); *C07D 239/47* (2013.01); *C07D 239/52* (2013.01); *C07D 403/12* (2013.01); *C07D 405/12* (2013.01); *A61K 45/06* (2013.01)

(58) Field of Classification Search
CPC .......................... C07D 239/47; C07D 239/48
See application file for complete search history.

(56) References Cited

U.S. PATENT DOCUMENTS

| | | |
|---|---|---|
| 6,844,351 B1 | 1/2005 | Chen |
| 8,362,248 B2 | 1/2013 | Jones et al. |
| 2001/0036945 A1 | 11/2001 | Yuan et al. |
| 2002/0019406 A1 | 2/2002 | Horvath et al. |
| 2002/0019525 A1 | 2/2002 | Yoon et al. |
| 2002/0042422 A1 | 4/2002 | Yuan et al. |
| 2002/0058668 A1 | 5/2002 | Yuan et al. |
| 2002/0065290 A1 | 5/2002 | Yuan et al. |
| 2002/0111490 A1 | 8/2002 | Horvath et al. |
| 2002/0123629 A1 | 9/2002 | Neumann |
| 2003/0105117 A1 | 6/2003 | Horvath et al. |
| 2005/0020601 A1 | 1/2005 | Corbett et al. |
| 2005/0038040 A1 | 2/2005 | Corbett et al. |
| 2005/0113379 A1 | 5/2005 | Ge et al. |
| 2006/0199823 A1 | 9/2006 | Ge et al. |
| 2008/0015196 A1 | 1/2008 | Doller et al. |

(Continued)

FOREIGN PATENT DOCUMENTS

| | | |
|---|---|---|
| EP | 0773023 A1 | 5/1997 |
| EP | 1059100 A2 | 12/2000 |

(Continued)

OTHER PUBLICATIONS

Banker et al. "Modern Pharmaceutics", 3rd Ed. p. 596 (1996).*
Burger's Medicinal Chemistry,, edited by Manfred E.Wolf, 5th Ed. Part 1, pp. 975-977 (1995).*
CA Registry No. 1500962-06-0, entered into CA Registry File on Dec. 22, 2013 ,supplied by Aurora Fine Chemicals.*
Aurora PrOductGuide, 1 p ag e, relrieved from the Internet at http.//www.aurorafinechemicals com/about.html on Apr. 28, 2015.*
European Extended Search Report dated Feb. 10, 2020 issued in EP 17849486.0.

(Continued)

Primary Examiner — Emily A Bernhardt
(74) Attorney, Agent, or Firm — Helen S. Baca; Tom Hunter; Weaver Austin Villeneuve & Sampson LLP

(57) ABSTRACT

In various embodiments novel allosteric antagonists of the CRFR1 receptor are provided. It discovered that allosteric CRFR1 receptor antagonists are effective to modulate p-Tau levels in Alzheimer's disease (AD) models. In one illustrative embodiment, a compound that is a CRFR1 receptor antagonist is a compound according to the formula

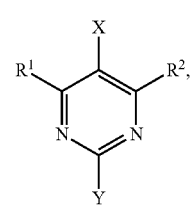

or a pharmaceutically acceptable salt, ester, amide, solvate, or prodrug thereof.

14 Claims, 19 Drawing Sheets

(56) References Cited

U.S. PATENT DOCUMENTS

| | | |
|---|---|---|
| 2009/0203755 A1 | 8/2009 | Richard |
| 2010/0222339 A1 | 9/2010 | Chen et al. |
| 2010/0249138 A1 | 9/2010 | Koob et al. |
| 2011/0301087 A1 | 12/2011 | Mcbride et al. |
| 2016/0039834 A1 | 2/2016 | Chesworth et al. |
| 2017/0020877 A1 | 1/2017 | Grigoriadis |

FOREIGN PATENT DOCUMENTS

| | | | |
|---|---|---|---|
| GB | 590706 | * | 7/1947 |
| WO | WO 95/33750 A1 | | 12/1995 |
| WO | WO 99/40089 A1 | | 8/1999 |
| WO | WO 2005/023806 A2 | | 3/2005 |
| WO | WO 2007/072163 A2 | | 6/2007 |
| WO | WO 2008/150446 A1 | | 12/2008 |
| WO | WO 2008/154026 A1 | | 12/2008 |

OTHER PUBLICATIONS

Chen et al. (1996) "Design and Synthesis of a Series of Non-Peptide High-Affinity Human Corticotropin-Releasing Factor 1 Receptor Antagonists", *J. Med. Chem*, 39: 4358-60 (3 pages).

Cocuzza et al. (1999) "Use of the suzuki reaction for the synthesis of aryl-substituted heterocycles as corticotropin-releasing hormone (CRH) antagonists", *Bioorganic & Medicinal Chemistry Letters*, 9(7): 1063-1066 (4 pages).

PCT International Search Report and Written Opinion dated Dec. 4, 2017 issued in PCT/US2017/050347.

PCT International Preliminary Report on Patentability dated Mar. 12, 2019 issued in PCT/US2017/050347.

Dautzenberg et al. (1997) "Identification of two corticotropin-releasing factor receptors from Xenopus laevis with high ligand selectivity: unusual pharmacology of the type 1 receptor." *J. Neurochem.*, 69(4): 1640-49 (10 pages).

DeLean et al. (1978) "Simultaneous analysis of families of sigmoidal curves: application to bioassay, radioligand assay, and physiological dose-response curves." *Am. J. Physiol.*, 235, E97-E102 (6 Pages).

Fleck et al. (2012) "Binding Kinetics Redefine the Antagonist Pharmacology of the Corticotropin-Releasing Factor Type 1 Receptor" *The Journal of Pharmacology and Experimental Therapeutics*. 341: 518-531 (14 pages).

Hollenstein et al. (2013) "Structure of class B GPCR corticotropin-releasing factor receptor 1." *Nature*, 499: 438-443 (8 pages—Supplementary Information).

Munson et al. (1980) "Ligand: a versatile computerized approach for characterization of ligand-binding systems." *Anal. Biochem.*, 107(1): 220-239 (20 pages).

Perrin et al. (1986) "Corticotropin-Releasing Factor Binding to the Anterior Pituitary Receptor Is Modulated by Divalent Cations and Guanyl Nucleotides" *Endocrinology*, 118(3): 1171-79 (9 pages).

Rissman et al. (2012) "Corticotropin-releasing factor receptor-dependent effects of repeated stress on tau phosphorylation, solubility, and aggregation" *P.N.A.S.*, 109: 6277-6282 (6 pages).

Zorrilla & Koob (2010) "Progress in corticotropin-releasing factor-1 antagonist development" *Drug. Discov. Today*, 15(9-10): 371-383 [NIH Public Access, Author Manuscript—24 pages].

Grigoriadis et al. (1989) "Corticotropin-Releasing Factor (CRF) Receptors in Intermediate Lobe of the Pituitary: Biochemical Characterization and Autoradiographic Localization" *Peptides*, 10: 179-188 (10 pages).

Australian Office Action dated Feb. 9, 2021 issued in AU 2017324942.

European Office Action dated Mar. 23, 2021 issued in EP 17849486.0.

\* cited by examiner

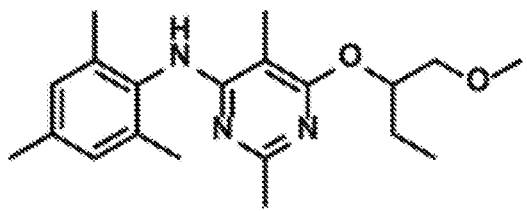
T41
NCE, LogP=5.04, TPSA= 56
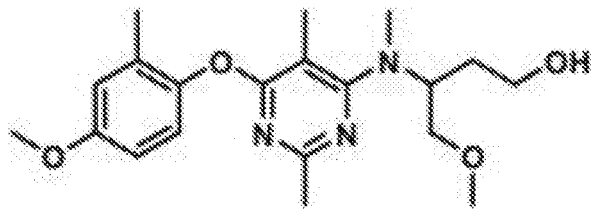
T42
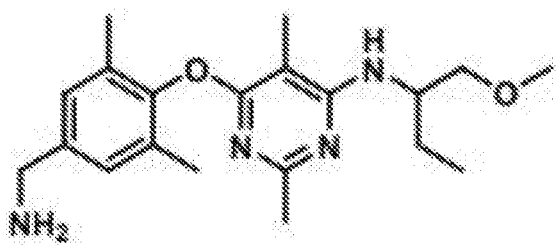
T43
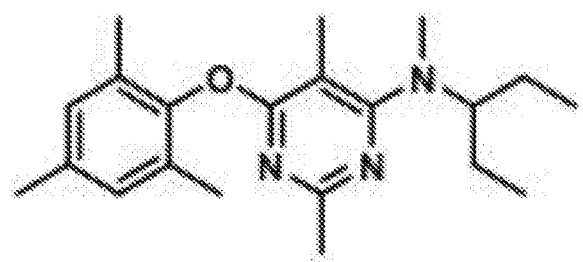
T44
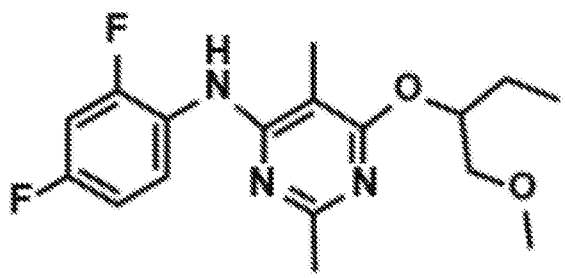
T45
NCE, LogP=4.1, TPSA=56
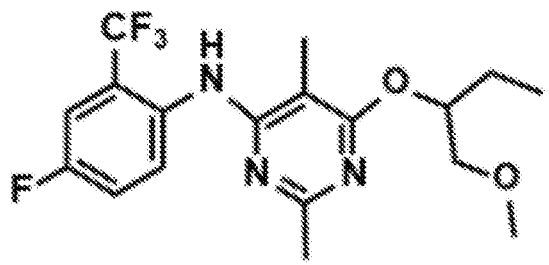
T46
NCE, LogP=4.83, TPSA=56
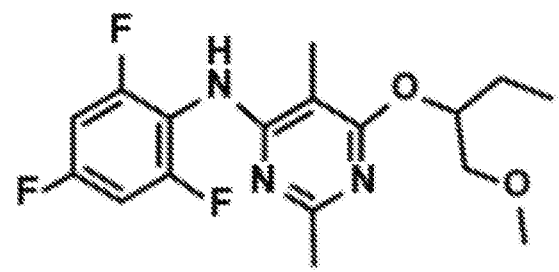
T47
NCE, LogP=4.19, TPSA=56
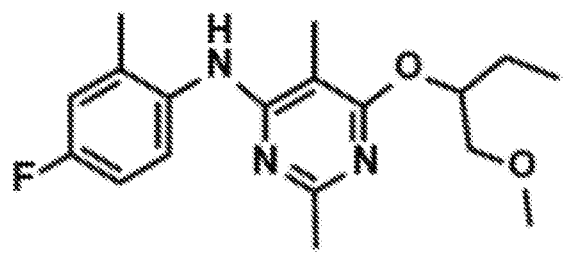
T48
NCE, LogP=4.38, TPSA=56
*Fig. 2, cont'd.*

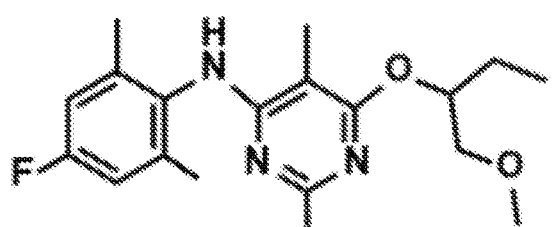
T49
NCE, LogP=4.76, TPSA=56
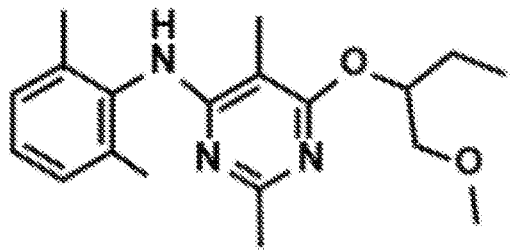
T50
NCE, LogP=4.64, TPSA=56
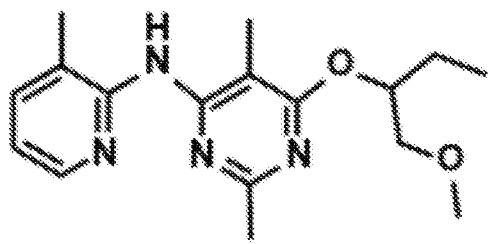
T51
NCE, LogP=3.77, TPSA=69
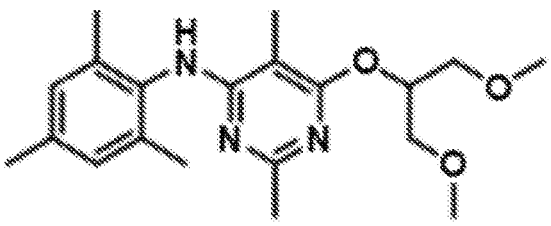
T52
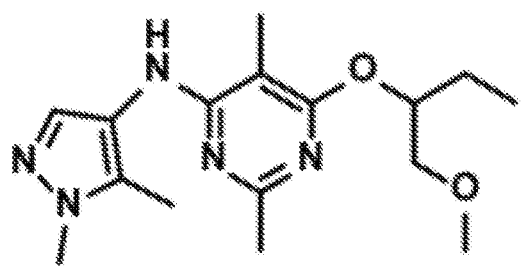
T53
NCE, LogP=2.44, TPSA=74
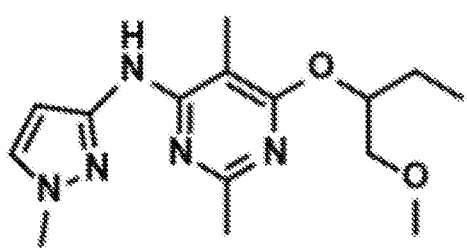
T54
NCE, LogP=2.41, TPSA=74
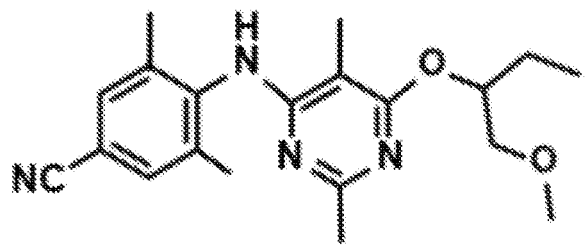
T55
NCE, LogP=4.35, TPSA=80
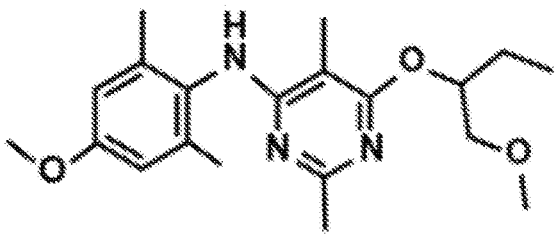
T56
NCE, LogP=4.65, TPSA=65
*Fig. 2, cont'd.*

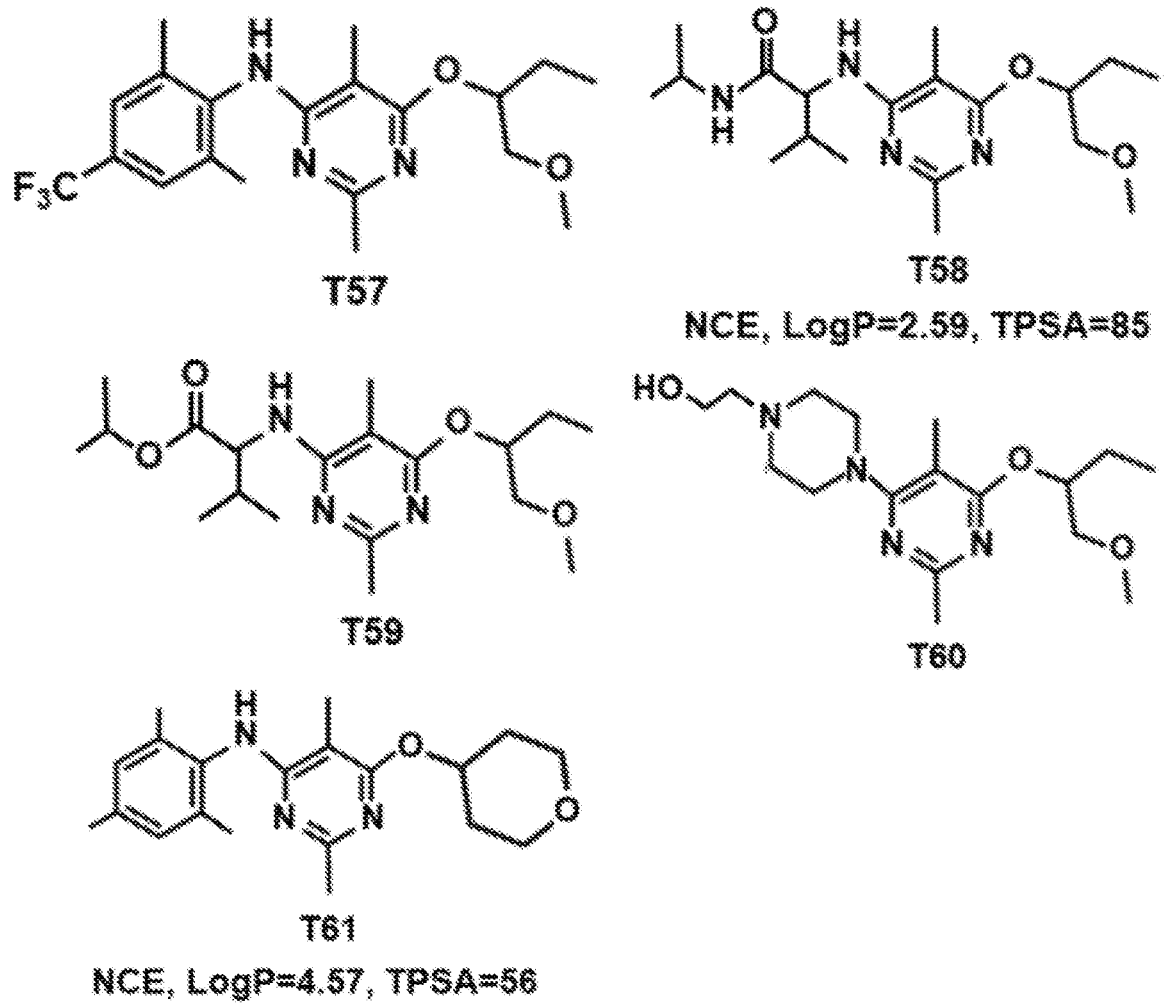
Fig. 2, cont'd.

ALLOSTERIC CORTICOTROPIN-RELEASING FACTOR RECEPTOR 1 (CRFR1) ANTAGONISTS THAT DECREASE P-TAU AND IMPROVE COGNITION

CROSS-REFERENCE TO RELATED APPLICATIONS

This application is a U.S. 371 National Phase of PCT/US2017/050347, filed on Sep. 6, 2017, which claims benefit of and priority to U.S. Ser. No. 62/384,656, filed on Sep. 7, 2016, both of which are incorporated herein by reference in their entirety for all purposes.

STATEMENT OF GOVERNMENTAL SUPPORT

[Not Applicable]

BACKGROUND

Corticotropin releasing factor (CRF) is a 41 amino acid peptide that is the primary physiological regulator of proopiomelanocortin (POMC) derived peptide secretion from the anterior pituitary gland (see, e.g., Rivier et al. (1983) *Proc. Natl. Acad. Sci. USA*, 80(15): 4851-4855; Vale et al. (1981) *Science*, 213(4514): 1394-1397). In addition to its endocrine role at the pituitary gland, CRF is known to have a broad extrahypothalmic distribution in the CNS, contributing therein to a wide spectrum of autonomic behavioral and physiological effects consistent with a neurotransmitter or neuromodulator role in the brain (see, e.g., Vale et al. (1983) *Rec. Prog. Horm. Res.* 39: 245-270; Koob (1985) *Persp. Behav. Med.* 2: 39; De Souza et al., (1985) *J. Neurosci.* 5(12): 3189-3203). There is evidence that CRF plays a significant role in integrating the response in the immune system to physiological, psychological, and immunological stressors, in psychiatric disorders and neurological diseases including depression, anxiety-related disorders and feeding disorders, and in the etiology and pathophysiology of Alzheimer's disease, Parkinson's disease, Huntington's disease, progressive supranuclear palsy and amyotrophic lateral sclerosis, particularly as they relate to the dysfunction of CRF neurons in the central nervous system (see, e.g., Blalock (1989) *Physiol. Rev.*, 69: 1-32; Morley (1987) *Life Sci.* 41(5): 527-544; De Souze (1988) *Hosp. Practice*, 23: 59-71).

CRFR1 activity has also been implicated in the etiology of Cushing's disease, hypertension, stroke, irritable bowel syndrome, stress-induced gastric ulceration, premenstrual syndrome, sexual dysfunction, premature labor, inflammatory disorders, allergies, multiple sclerosis, visceral pain, sleep disorders, pituitary tumors or ectopic pituitary-derived tumors, chronic fatigue syndrome and fibromyalgia.

SUMMARY

In various embodiments novel allosteric antagonists of the CRFR1 receptor are provided. It was a surprising discovery that allosteric CRFR1 receptor antagonist are effective to modulate p-Tau levels in Alzheimer's disease (AD) models. Without being bound to a particular theory, it is believed that being allosteric CRFR1 antagonists, the compounds described herein have greater selectivity for the CRFR1 receptor and hence a greater safety profile compared to direct CRFR1 receptor antagonists.

Various embodiments contemplated herein may include, but need not be limited to, one or more of the following:

Embodiment 1

A compound that is a CRFR1 receptor antagonist, wherein said compound is a compound according to the formula

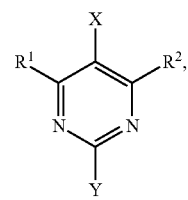

or a pharmaceutically acceptable salt, ester, amide, solvate, or prodrug thereof, wherein:
- X and Y are independently selected from the group consisting of Me, H, $CF_3$, deuterated methyl, and halogen;
- $R^1$ is, or comprises, a moiety selected from the group consisting of linear or substituted aminoalkyl, substituted phenoxide, unsubstituted phenoxide, substituted alkoxide, unsubstituted alkoxide, substituted aminoaryl, unsubstituted aminoaryl, substituted aminoheteroaryl, and unsubstituted aminoheteroaryl; and
- $R^2$ is, or comprises, a moiety selected from the group consisting of linear or substituted alkoxide, phenoxide, substituted aminoalkyl, unsubstituted aminoalkyl, and pyran.

Embodiment 2

The compound of embodiment 1, wherein said compound is an allosteric CRFR1 receptor antagonist.

Embodiment 3

The compound according to any one of embodiments 1-2, wherein X is $CH_3$.

Embodiment 4

The compound according to any one of embodiments 1-3, wherein Y is $CH_3$.

Embodiment 5

The compound according to any one of embodiments 1-4, wherein $R^2$ is

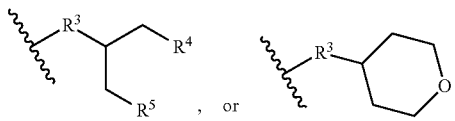

wherein:
- $R^3$ is selected from the group consisting of O, NH, and $NCH_3$;
- $R^4$ is selected from the group consisting of $OCH_3$, $CH_3$, $CH_2OH$; and $R^5$ is selected from the group consisting of $CH_3$, and $OCH_3$.

Embodiment 6

The compound according to any one of embodiments 1-5, wherein $R^2$ is

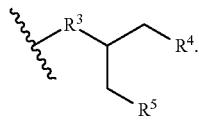

Embodiment 7

The compound of embodiment 6, wherein $R^4$ is $OCH_3$.

Embodiment 8

The compound of embodiment 6, wherein $R^4$ is $CH_3$.

Embodiment 9

The compound of embodiment 6, wherein $R^4$ is $CH_2OH$.

Embodiment 10

The compound according to any one of embodiments 6-9, wherein $R^5$ is $CH_3$.

Embodiment 11

The compound according to any one of embodiments 6-9, wherein $R^5$ is $OCH_3$.

Embodiment 12

The compound of embodiment 6, wherein $R^2$ is selected from the group consisting of

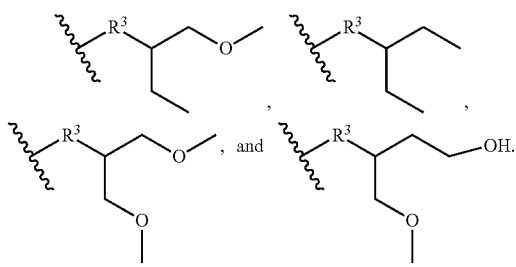

Embodiment 13

The compound of embodiment 6, wherein $R^2$ is

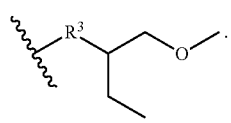

Embodiment 14

The compound of embodiment 5, wherein $R^2$ is

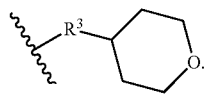

Embodiment 15

The compound according to any one of embodiments 5-14, wherein $R^3$ is O.

Embodiment 16

The compound according to any one of embodiments 5-14, wherein $R^3$ is NH.

Embodiment 17

The compound according to any one of embodiments 5-14, wherein $R^3$ is $NCH_3$.

Embodiment 18

The compound according to any one of embodiments 1-17, wherein $R^1$ comprises a substituted or unsubstituted phenyl.

Embodiment 19

The compound of embodiment 18, wherein $R^1$ comprises a substituted phenyl.

Embodiment 20

The compound of embodiment 19, wherein $R^1$ is

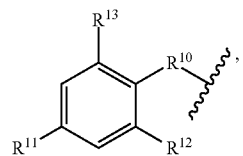

wherein:
$R^{10}$ is NH or O; $R^{11}$ is selected from the group consisting of H, $CH_3$, $OCH_3$, halogen, $CH_2NH_2$, CN, and $CR^8_3$ where $R^8$ is halogen;
$R^{12}$ is selected from the group consisting of H, $CH_3$, or halogen; and
$R^{13}$ is selected from the group consisting of $CH_3$, halogen, and $CR^9_3$ where $R^9$ is halogen.

Embodiment 21

The compound of embodiment 20, wherein $R^{11}$ is H.

Embodiment 22

The compound of embodiment 20, wherein $R^{11}$ is $CH_3$.

Embodiment 23

The compound of embodiment 20, wherein $R^{11}$ is $OCH_3$.

Embodiment 24

The compound of embodiment 20, wherein $R^{11}$ is halogen.

Embodiment 25

The compound of embodiment 24, wherein $R^{11}$ is Cl.

Embodiment 26

The compound of embodiment 24, wherein $R^{11}$ is F.

Embodiment 27

The compound of embodiment 24, wherein $R^{11}$ is $CH_2NH_2$.

Embodiment 28

The compound of embodiment 24, wherein $R^{11}$ is CN.

Embodiment 29

The compound of embodiment 24, wherein $R^{11}$ is $CF_3$.

Embodiment 30

The compound according to any one of embodiments 20-29, wherein $R^{12}$ is H.

Embodiment 31

The compound according to any one of embodiments 20-29, wherein $R^{12}$ is halogen.

Embodiment 32

The compound of embodiment 31, wherein $R^{12}$ is F.

Embodiment 33

The compound of embodiment 31, wherein $R^{12}$ is Cl.

Embodiment 34

The compound according to any one of embodiments 20-29, wherein $R^{12}$ is $CH_3$.

Embodiment 35

The compound of embodiment 20, wherein $R^1$ is selected from the group consisting of

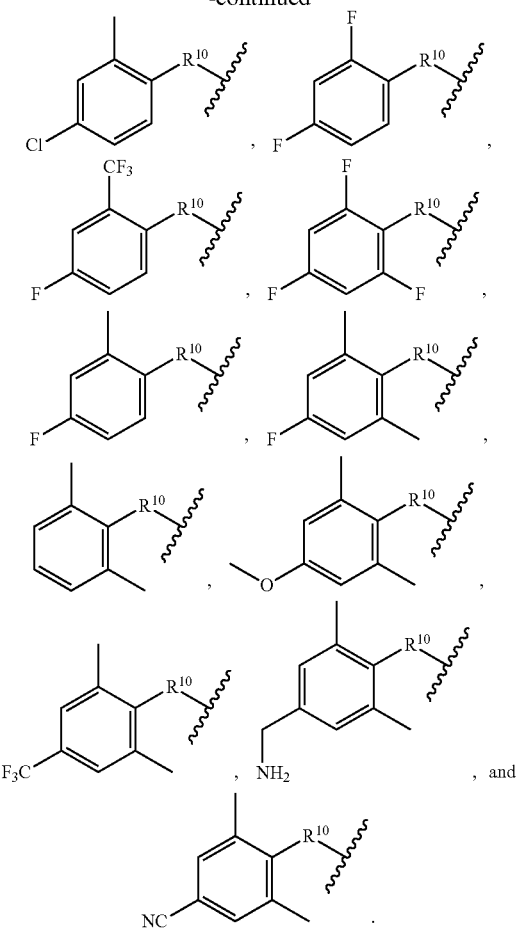

Embodiment 36

The compound of embodiment 20, wherein $R^1$ is

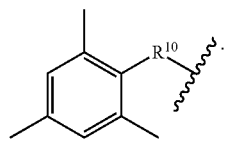

Embodiment 37

The compound according to any one of embodiments 1-17, wherein $R^1$ is

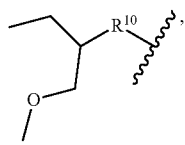

wherein $R^{10}$ is NH or O.

Embodiment 38

The compound according to any one of embodiments 1-17, wherein $R^1$ is

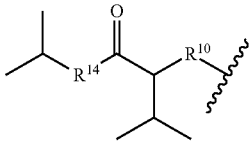

wherein: $R^{10}$ is NH or O; and $R^{14}$ is NH or O.

Embodiment 39

The compound of embodiment 38, wherein $R^{14}$ is NH.

Embodiment 40

The compound of embodiment 38, wherein $R^{14}$ is O.

Embodiment 41

The compound according to any one of embodiments 1-17, wherein $R^1$ is selected from the group consisting of

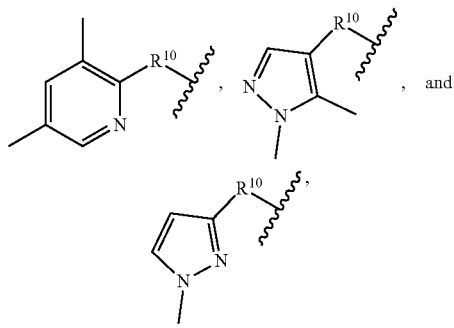

wherein $R^{10}$ is NH or O.

Embodiment 42

The compound according to any one of embodiments 20-41, wherein $R^{10}$ is NH.

Embodiment 43

The compound according to any one of embodiments 20-41, wherein $R^{10}$ is O.

Embodiment 44

The compound according to any one of embodiments 1-17, wherein $R^1$ is

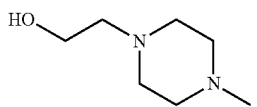

Embodiment 45

The compound according to any one of embodiments 1, 5, 6, 12, and 20, wherein said compound is selected from the group consisting of T41, T33, T34, T35, T36, T37, T38, T39, T42, T43, T44, T45, T46, T47, T48, T49, T50, T51, T52, T55, T56, and T57, or a pharmaceutically acceptable salt, ester, amide, solvate, or prodrug thereof.

Embodiment 46

The compound of embodiment 45, wherein said compound comprises T41, or a pharmaceutically acceptable salt, ester, amide, solvate, or prodrug thereof.

Embodiment 47

The compound according to any one of embodiments 1, 5, 6, 12, 13, and 41, wherein said compound is selected from the group consisting of T53, and T54 or a pharmaceutically acceptable salt, ester, amide, solvate, or prodrug thereof.

Embodiment 48

The compound according to any one of embodiments 1, 5, 6, 12, 13, and 38, wherein said compound is selected from the group consisting of T58, and T59 or a pharmaceutically acceptable salt, ester, amide, solvate, or prodrug thereof.

Embodiment 49

The compound according to any one of embodiments 1, 5, 6, 12, 13, and 44, wherein said compound is T60 or a pharmaceutically acceptable salt, ester, amide, solvate, or prodrug thereof.

Embodiment 50

The compound according to any one of embodiments 1, 5, 14, 35, and 36, wherein said compound is T61 or a pharmaceutically acceptable salt, ester, amide, solvate, or prodrug thereof.

Embodiment 51

A compound that is a CRFR1 receptor antagonist, wherein said compound is a compound according to the formula

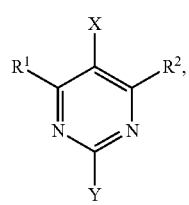

I or a pharmaceutically acceptable salt, ester, amide, or prodrug thereof, wherein:
  X and Y are independently selected from the group consisting of Me, H, $CF_3$, deuterated methyl, and halogen;
  $R^1$ is selected from the group consisting of linear or substituted aminoalkyl, substituted or unsubstituted, aminoaryl, aminoheteroaryl, substituted aminoheteroaryl; and $R^2$ is selected from the group consisting of linear or substituted alkoxide or phenoxide.

Embodiment 52

The compound of embodiment 51, wherein said compound is an allosteric CRFR1 receptor antagonist.

Embodiment 53

The compound according to any one of embodiments 51-52, wherein X is $CH_3$.

Embodiment 54

The compound according to any one of embodiments 51-53, wherein Y is $CH_3$.

Embodiment 55

The compound according to any one of embodiments 51-54, wherein $R^2$ is

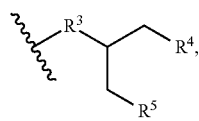

wherein:
- $R^3$ is selected from the group consisting of O, NH, and $NCH_3$;
- $R^4$ is selected from the group consisting of $OCH_3$, $CH_3$, $CH_2OH$; and
- $R^5$ is selected from the group consisting of $CH_3$, and $OCH_3$.

Embodiment 56

The compound of embodiment 55, wherein $R^4$ is $OCH_3$.

Embodiment 57

The compound of embodiment 55, wherein $R^4$ is $CH_3$.

Embodiment 58

The compound of embodiment 55, wherein $R^4$ is $CH_2OH$.

Embodiment 59

The compound according to any one of embodiments 55-58, wherein $R^5$ is $CH_3$.

Embodiment 60

The compound according to any one of embodiments 55-58, wherein $R^5$ is $OCH_3$.

Embodiment 61

The compound of embodiment 55, wherein $R^2$ is selected from the group consisting of

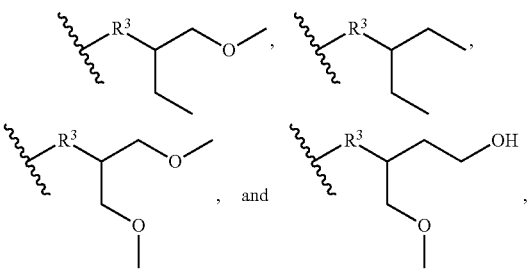

, and

Embodiment 62

The compound of embodiment 55, wherein $R^2$ is

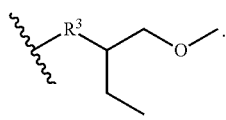

Embodiment 63

The compound according to any one of embodiments 51-54, wherein $R^2$ is

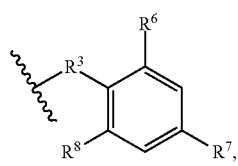

wherein:
- $R^6$ is selected from the group consisting of $CH_3$, halogen, and $CR^9_3$ where $R^9$ is halogen;
- $R^7$ is halogen; and
- $R^8$ is selected from the group consisting of H, and halogen.

Embodiment 64

The compound of embodiment 63, wherein $R^6$ is $CH_3$.

Embodiment 65

The compound of embodiment 63, wherein $R^6$ is halogen.

Embodiment 66

The compound of embodiment 65, wherein $R^6$ is Cl or F.

Embodiment 67

The compound of embodiment 65, wherein $R^6$ is F.

Embodiment 68

The compound of embodiment 63, wherein $R^6$ is $CR^9{}_3$.

Embodiment 69

The compound of embodiment 68, wherein $R^9$ is Cl or F.

Embodiment 70

The compound of embodiment 68, wherein $R^9$ is F.

Embodiment 71

The compound according to any one of embodiments 63-70, wherein $R^7$ is Cl or F.

Embodiment 72

The compound according to any one of embodiments 63-70, wherein $R^7$ is F.

Embodiment 73

The compound according to any one of embodiments 63-72, wherein $R^8$ is H.

Embodiment 74

The compound according to any one of embodiments 63-72, wherein $R^8$ is halogen.

Embodiment 75

The compound of embodiment 74, wherein $R^8$ is Cl or F.

Embodiment 76

The compound of embodiment 74, wherein $R^8$ is F.

Embodiment 77

The compound of embodiment 63, wherein $R^2$ is selected from the group consisting of

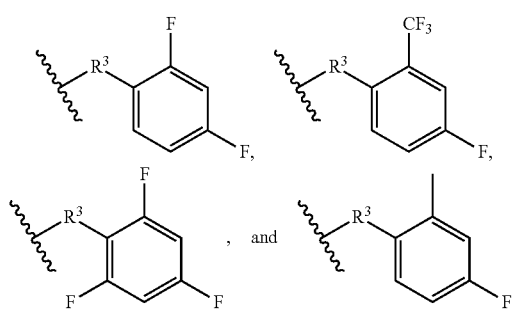

Embodiment 78

The compound according to any one of embodiments 55-77, wherein $R^3$ is O.

Embodiment 79

The compound according to any one of embodiments 55-77, wherein $R^3$ is NH.

Embodiment 80

The compound according to any one of embodiments 55-77, wherein $R^3$ is $NCH_3$.

Embodiment 81

The compound according to any one of embodiments 51-80, wherein $R^1$ is

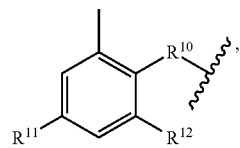

wherein:
$R^{10}$ is NH or O;
$R^{11}$ is selected from the group consisting of $CH_3$, $OCH_3$, halogen, $CH_2NH_2$, and
$R^{12}$ is H or $CH_3$.

Embodiment 82

The compound of embodiment 81, wherein $R^{11}$ is $CH_3$.

Embodiment 83

The compound of embodiment 81, wherein $R^{11}$ is $OCH_3$.

Embodiment 84

The compound of embodiment 81, wherein $R^{11}$ is halogen.

Embodiment 85

The compound of embodiment 84, wherein $R^{11}$ is Cl or F.

Embodiment 86

The compound of embodiment 84, wherein $R^{11}$ is F.

Embodiment 87

The compound according to any one of embodiments 81-86, wherein $R^{12}$ is H.

Embodiment 88

The compound according to any one of embodiments 81-86, wherein $R^{12}$ is $CH_3$.

Embodiment 89

The compound according to any one of embodiments 51-80, wherein R¹ is

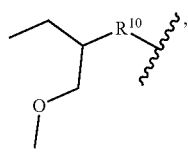

wherein R¹⁰ is NH or O.

Embodiment 90

The compound according to any one of embodiments 51-80, wherein R¹ is selected from the group consisting of

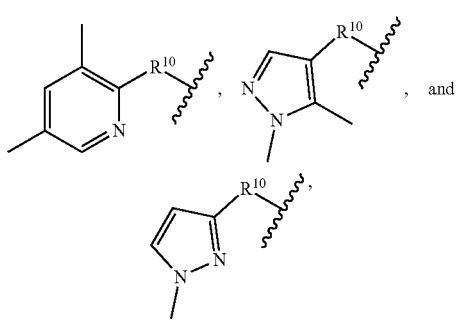

wherein R¹⁰ is NH or O.

Embodiment 91

The compound according to any one of embodiments 33-43, wherein R¹⁰ is NH.

Embodiment 92

The compound according to any one of embodiments 33-43, wherein R¹⁰ is O.

Embodiment 93

The compound according to any one of embodiments 51, 55, 61, 62, and 81, wherein said compound is selected from the group consisting of

T33

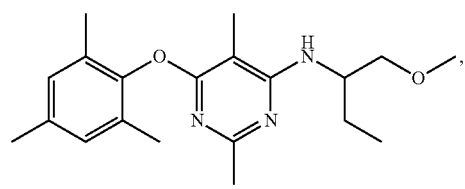

T35

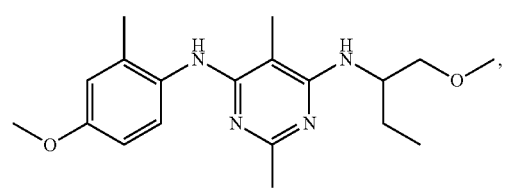

T36

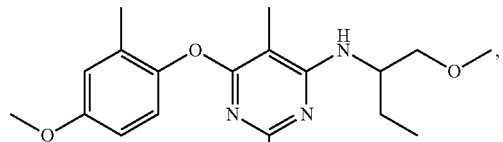

T37

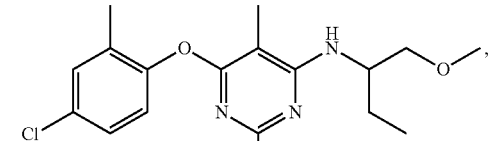

T43

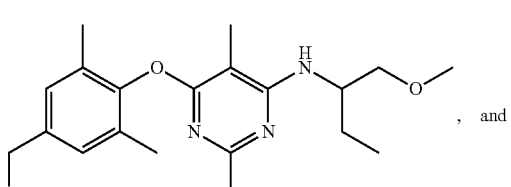

, and

T49

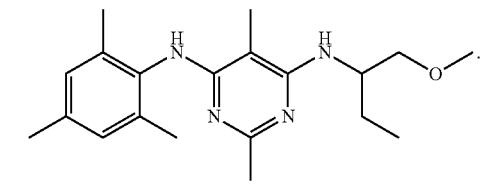

Embodiment 94

The compound according to any one of embodiments 51, 55, 61, and 62, wherein said compound is selected from the group consisting of

T38

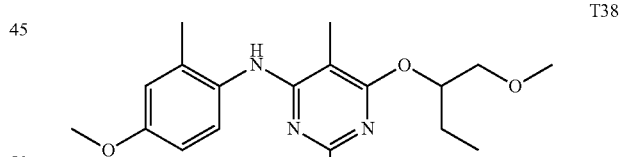

T39

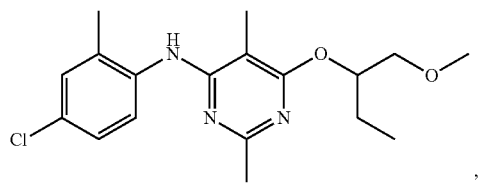

T40

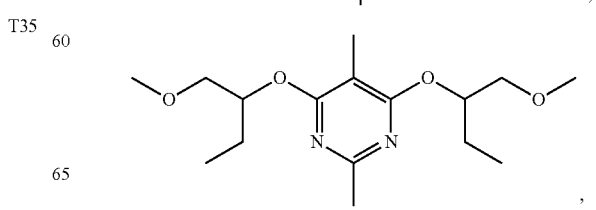

-continued

T41
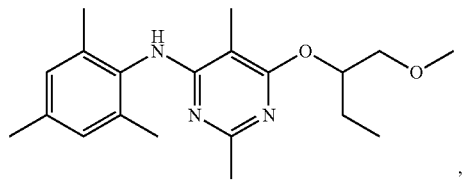,

T50
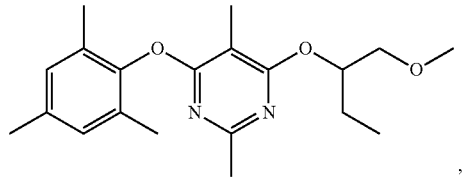,

T51
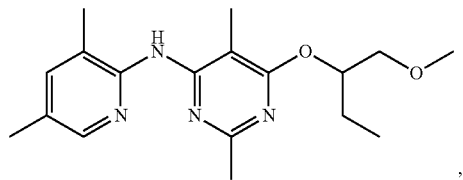,

T53
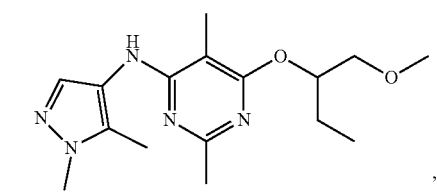,

T54
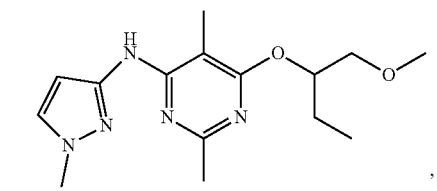,

T33
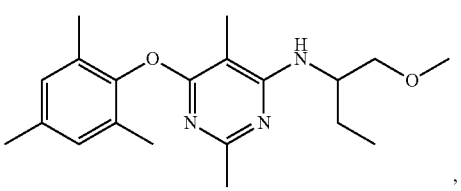, and

T56
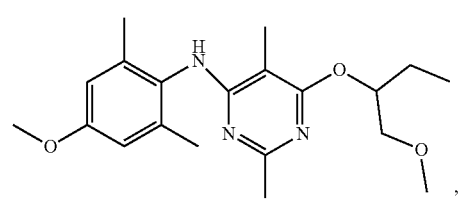, and/or T55.

Embodiment 95

The compound according to any one of embodiments 51, 55, 61, and 81, wherein said compound is selected from the group consisting of T34
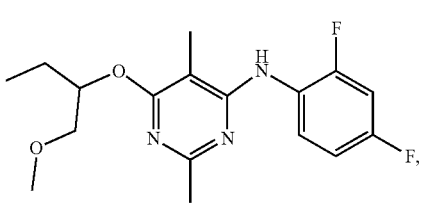, and

T44

Embodiment 96

The compound according to any one of embodiments 51, 55, 61, and 81, wherein said compound is selected from the group consisting of

T42

, and

T52

Embodiment 97

The compound according to any one of embodiments 51, 63, and 89, wherein said compound is selected from the group consisting of

T45

T46 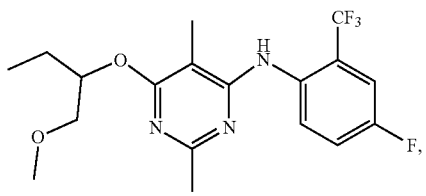

T47 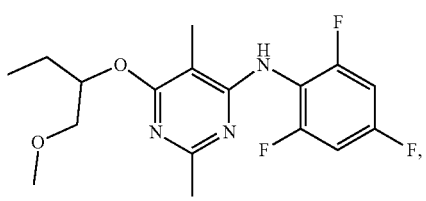

T48 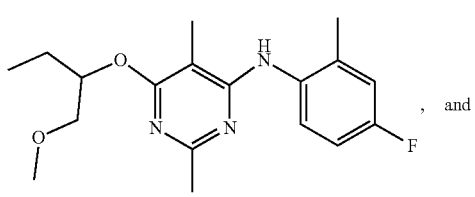, and

T57 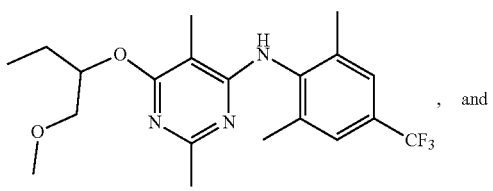, and

T60 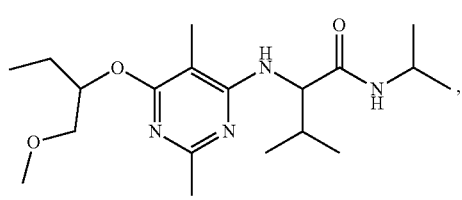

Embodiment 98

The compound of embodiment 1, wherein said compound comprises a compound selected from the group consisting of T58 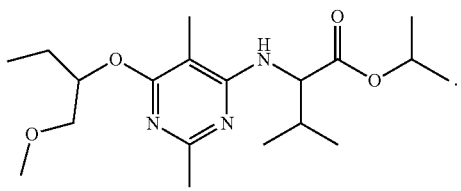,

T59

[structure]

Embodiment 99

The compound of embodiments 1 or 51, wherein said compound comprises a compound according to a formula shown in FIG. 2, or a pharmaceutically acceptable salt, ester, amide, solvate, or prodrug thereof.

Embodiment 100

The compound according to any one of embodiments 1-99, wherein said compound is a substantially pure "R" enantiomer.

Embodiment 101

The compound according to any one of embodiments 1-99, wherein said compound is a substantially pure "S" enantiomer.

Embodiment 102

A pharmaceutical formulation comprising the compound according to any one of embodiments 1-101, and a pharmaceutically acceptable carrier or excipient.

Embodiment 103

The formulation of embodiment 102, wherein said formulation is formulated for administration via a route selected from the group consisting of oral administration, nasal administration, administration via inhalation, oral administration, rectal administration, intraperitoneal injection, intravascular injection, subcutaneous injection, transcutaneous administration, and intramuscular injection.

Embodiment 104

The formulation according to any one of embodiments 102-103, wherein said formulation is a unit dosage formulation.

Embodiment 105

The formulation according to any one of embodiments 102-104, wherein said formulation is sterile.

Embodiment 106

A method of mitigating in a mammal one or more symptoms associated with a disease characterized by amyloid deposits in the brain, or delaying or preventing the onset of said symptoms, said method comprising:
administering, or causing to be administered, to said mammal a compound according to any one of embodiments 1-101, or a pharmaceutical formulation according to any one of embodiments 102-105, wherein said administering is in an amount sufficient to mitigate said one or more symptoms.

Embodiment 107

A method of reducing the risk, lessening the severity, or delaying the progression or onset of a disease characterized by beta-amyloid deposits in the brain of a mammal, said method comprising:
administering, or causing to be administered, to said mammal a compound according to any one of embodiments 1-101, or a pharmaceutical formulation according to any one of embodiments 102-105, wherein said administering is in an amount sufficient to reducing the risk, lessen the severity, or delay the progression or onset of said disease.

Embodiment 108

The method according to any one of embodiments 106-107, wherein said disease is a disease selected from the group consisting of Alzheimer's disease, Cerebrovascular dementia, Parkinson's disease, Huntington's disease, Cerebral amyloid angiopathy, amyotrophic lateral sclerosis (ALS), traumatic brain injury (TBI), and stroke.

Embodiment 109

A method of preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease in a mammal, said method comprising:
administering, or causing to be administered, to said mammal a compound according to any one of embodiments 1-101, or a pharmaceutical formulation according to any one of embodiments 102-105, wherein said administering is in an amount sufficient to promote the processing of amyloid precursor protein (APP) by the non-amyloidogenic pathway.

Embodiment 110

A method of promoting the processing of amyloid precursor protein (APP) by the non-amyloidogenic pathway as characterized by increasing sAPPα and/or the sAPPα/Aβ42 ratio in a mammal, said method comprising: administering, or causing to be administered, to said mammal a compound according to any one of embodiments 1-101, or a pharmaceutical formulation according to any one of embodiments 102-105, wherein said administering is in an amount sufficient to promote the processing of amyloid precursor protein (APP) by the non-amyloidogenic pathway.

Embodiment 111

The method according to any one of embodiments 106 to 110, wherein the mammal is human.

Embodiment 112

The method according to any one of embodiments 106 to 111, wherein the mammal is diagnosed as having mild cognitive impairment (MCI).

Embodiment 113

The method according to any one of embodiments 106 to 112, wherein administration of said compound delays or prevents the progression of MCI to Alzheimer's disease.

Embodiment 114

The method according to any one of embodiments 106-108, and 110-111, wherein the disease is Alzheimer's disease.

Embodiment 115

The method of embodiment 114, wherein the mammal is diagnosed as having Alzheimer's disease.

Embodiment 116

The method according to any one of embodiments 106 to 114, wherein the mammal is at risk of developing Alzheimer's disease.

Embodiment 117

The method of embodiment 116, wherein the mammal has a familial risk for having Alzheimer's disease.

Embodiment 118

The method of embodiment 116, wherein the mammal has a familial Alzheimer's disease (FAD) mutation.

Embodiment 119

The method of embodiment 116, wherein the mammal has the APOE ε4 allele.

Embodiment 120

The method according to any one of embodiments 106 to 119, wherein the mammal is free of and does not have genetic risk factors of for a neurological disorder not associated with or characterized by the formation of beta-amyloid plaques.

Embodiment 121

The method according to any one of embodiments 106 to 119, wherein the mammal is not diagnosed as having or at risk schizophrenia or other neuropsychiatric disorders.

Embodiment 122

The method according to any one of embodiments 106 to 121, wherein the mammal does not have a neurological disease or disorder other than Alzheimer's disease.

Embodiment 123

The method according to any one of embodiments 106 to 121, wherein the mammal is not diagnosed as having or at risk for a neurological disease or disorder other than Alzheimer's disease.

Embodiment 124

The method according to any one of embodiments 106 to 123, wherein the mitigation comprises a reduction in the CSF of levels of one or more components selected from the group consisting of Tau, phospho-Tau (pTau), APPneo, soluble Aβ40 and soluble Aβ 42.

Embodiment 125

The method according to any one of embodiments 106 to 123, wherein the mitigation comprises a reduction of the plaque load in the brain of the mammal.

Embodiment 126

The method according to any one of embodiments 106 to 123, wherein the mitigation comprises a reduction in the rate of plaque formation in the brain of the mammal.

Embodiment 127

The method according to any one of embodiments 106 to 123, wherein the mitigation comprises an improvement in the cognitive abilities of the mammal.

Embodiment 128

The method according to any one of embodiments 106 to 123, wherein the mammal is a human and the mitigation comprises a perceived improvement in quality of life by the human.

Embodiment 129

The method according to any one of embodiments 106 to 128, wherein the compound is administered orally.

Embodiment 130

The method according to any one of embodiments 106 to 128, wherein the administering is over a period of at least three weeks.

Embodiment 131

The method according to any one of embodiments 106 to 128, wherein the administering is over a period of at least 6 months.

Embodiment 132

The method according to any one of embodiments 106 to 131, wherein the compound is formulated for administration via a route selected from the group consisting of isophoretic delivery, transdermal delivery, aerosol administration, administration via inhalation, oral administration, intravenous administration, and rectal administration.

Embodiment 133

The method according to any one of embodiments 106 to 132, wherein the compound is administered via a route selected from the group consisting of isophoretic delivery, transdermal delivery, aerosol administration, administration via inhalation, oral administration, intravenous administration, and rectal administration.

Embodiment 134

The method according to any one of embodiments 106 to 133, wherein said compound is administered in conjunction with an agent selected from the group consisting of tropisetron, a tropisetron analog, disulfiram, a disulfiram analog, honokiol, a honokiol analog, nimetazepam, a nimetazepam analog, donepezil, rivastigmine, galantamine, tacrine, memantine, solanezumab, bapineuzmab, alzemed, flurizan, ELND005, valproate, semagacestat, rosiglitazone, phenserine, cernezumab, dimebon, egcg, gammagard, PBT2, PF04360365, NIC5-15, bryostatin-1, AL-108, nicotinamide, EHT-0202, BMS708163, NP12, lithium, ACC001, AN1792, ABT089, NGF, CAD106, AZD3480, SB742457, AD02, huperzine-A, EVP6124, PRX03140, PUFA, HF02, MEM3454, TTP448, PF-04447943, GSK933776, MABT5102A, talsaclidine, UB311, begacestat, R1450, PF3084014, V950, E2609, MK0752, CTS21166, AZD-3839, LY2886721, CHF5074, an anti-inflammatory, dapsone, an anti-TNF antibody, a statin, and a BACE inhibitor.

Embodiment 135

A kit comprising:
a container containing a compound according to any one of embodiments 1-101, or a pharmaceutical formulation according to any one of embodiments 102-105; and
instructional materials teaching the use of said composition to mitigate one or more symptoms associated with a disease characterized by amyloid deposits in the brain, and/or the use of said composition in delaying or preventing the onset of one or more of said symptoms.

Embodiment 136

The kit of embodiment 135, wherein said disease is a disease selected from the group consisting of MCI. Alzheimer's disease, Cerebrovascular dementia, Parkinson's disease, Huntington's disease, Cerebral amyloid angiopathy, amyotrophic lateral sclerosis (ALS), traumatic brain injury (TBI) and stroke.

Embodiment 137

The kit of embodiment 135, wherein said disease is Alzheimer's disease.

Embodiment 138

The kit of embodiment 135, wherein said disease is MCI.

Embodiment 139

A method for the treatment or prophylaxis of age related macular degeneration (AMD) in a mammal, said method comprising:
administering, or causing to be administered, to a mammal in need thereof a compound according to any one of embodiments 1-101, or a pharmaceutical formulation according to any one of embodiments 102-105, in an amount sufficient to ameliorate one or more symptoms of AMD and/or to slow the progression of AMD, and/or to reverse the effects of AMD.

Embodiment 140

The method of embodiment 139, wherein the mammal is a human.

Embodiment 141

The method of embodiment 139, wherein said mammal is a human diagnosed as having or as at risk for AMD.

Embodiment 142

A method for the treatment or prophylaxis of a pathology in a mammal, said pathology being selected from the group consisting of a psychiatric disorder (including depression, anxiety-related disorders and feeding disorders), Parkinson's disease, Huntington's disease, progressive supranuclear palsy and amyotrophic lateral sclerosis, Cushing's disease, hypertension, stroke, irritable bowel syndrome, stress-induced gastric ulceration, premenstrual syndrome, sexual dysfunction, premature labor, inflammatory disorders, allergies, multiple sclerosis, visceral pain, sleep disorders, pituitary tumors or ectopic pituitary-derived tumors, chronic fatigue syndrome, and fibromyalgia, said method comprising:
  administering, or causing to be administered, to a mammal in need thereof an effective amount of a compound according to any one of embodiments 1-101, or a pharmaceutical formulation according to any one of embodiments 102-105.

Definitions

A receptor antagonist is a type of receptor ligand or drug that blocks or dampens agonist-mediated responses rather than provoking a biological response itself upon binding to a receptor. They are sometimes called blockers; examples include alpha blockers, beta blockers, and calcium channel blockers. In various embodiments receptor antagonists can comprise direct receptor antagonists, or allosteric receptor antagonists. Typically, direct antagonists have affinity but no little or no efficacy for their cognate receptors, and binding will typically disrupt the interaction and inhibit the function of an agonist or inverse agonist at their cognate receptor. Direct antagonists mediate their effects by binding to the active orthosteric (i.e., right place) site of a receptor (e.g., the binding site of the cognate ligand for that receptor).

An "allosteric antagonist" typically binds to other sites (than the native ligand (e.g., agonist) site) on the receptor or they may interact at unique binding sites not normally involved in the biological regulation of the receptor's activity.

The terms "allosteric CRFR1 antagonist" or "allosteric CRFR1 receptor antagonist" or "allosteric CRFR1R antagonist) are used interchangeably and refer to a compound that has allosteric antagonist activity at the CRFR1 receptor.

The terms "subject," "individual," and "patient" may be used interchangeably and typically a mammal, in certain embodiments a human or a non-human primate. While the compositions and methods are described herein with respect to use in humans, they are also suitable for animal, e.g., veterinary use. Thus certain illustrative organisms include, but are not limited to humans, non-human primates, canines, equines, felines, porcines, ungulates, lagomorphs, and the like. Accordingly, certain embodiments contemplate the compositions and methods described herein for use with domesticated mammals (e.g., canine, feline, equine), laboratory mammals (e.g., mouse, rat, rabbit, hamster, guinea pig), and agricultural mammals (e.g., equine, bovine, porcine, ovine), and the like. The term "subject" does not require one to have any particular status with respect to a hospital, clinic, or research facility (e.g., as an admitted patient, a study participant, or the like). Accordingly, in various embodiments, the subject can be a human (e.g., adult male, adult female, adolescent male, adolescent female, male child, female child) under the care of a physician or other health worker in a hospital, psychiatric care facility, as an outpatient, or other, clinical context. In certain embodiments, the subject may not be under the care or prescription of a physician, or other, health worker. In certain embodiments the subject may not be under the care a physician or health worker and, in certain embodiments, may self-prescribe and/or self-administer the compounds described herein.

As used herein, the phrase "a subject in need thereof" refers to a subject, as described infra, that suffers or is at a risk of suffering (e.g., pre-disposed such as genetically pre-disposed) from the diseases or conditions listed herein.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount is less than the therapeutically effective amount.

The terms "treatment," "treating," or "treat" as used herein, refer to actions that produce a desirable effect on the symptoms or pathology of a disease or condition, particularly those that can be effected utilizing the multi-component formulation(s) described herein, and may include, but are not limited to, even minimal changes or improvements in one or more measurable markers of the disease or condition being treated. Treatments also refers to delaying the onset of, retarding or reversing the progress of, reducing the severity of, or alleviating or preventing either the disease or condition to which the term applies, or one or more symptoms of such disease or condition. "Treatment," "treating," or "treat" does not necessarily indicate complete eradication or cure of the disease or condition, or associated symptoms thereof. In one embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

An "effective amount" refers to an amount effective, at dosages and for periods of time necessary, to achieve the desired therapeutic or prophylactic result. A "therapeutically effective amount" of compound (e.g., a CRFR1 antagonist) or formulation thereof described herein may vary according to factors such as the disease state, age, sex, and weight of the individual, and the ability of the treatment to elicit a desired response in the individual. A therapeutically effective amount is also one in which any toxic or detrimental effects of a treatment are substantially absent or are outweighed by the therapeutically beneficial effects. The term "therapeutically effective amount" refers to an amount of one or more active agents described herein (e.g., CRFR1 receptor antagonists) or composition comprising the same that is effective to "treat" a disease or disorder in a mammal (e.g., a patient). In one embodiment, a therapeutically effective amount is an amount sufficient to improve at least one symptom associated with a neurological disorder, improve neurological function, improve cognition, or one or more markers of a neurological disease, or to enhance the efficacy of one or more pharmaceuticals administered for the treatment or prophylaxis of a neurodegenerative pathology. In certain embodiments, an effective amount is an amount sufficient alone, or in combination with a pharmaceutical agent to prevent advancement or the disease, delay progression, or to cause regression of a disease, or which is capable of reducing symptoms caused by the disease.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

As used herein, the phrases "improve at least one symptom" or "improve one or more symptoms" or equivalents thereof, refer to the reduction, elimination, or prevention of one or more symptoms of pathology or disease. Illustrative symptoms of pathologies treated, ameliorated, or prevented by the compositions (active agents) described herein (e.g., allosteric CRFR1 receptor antagonists, or an enantiomer, a mixture of enantiomers, or a mixture of two or more diastereomers thereof, or a pharmaceutically acceptable salt, ester, amide, solvate, hydrate, or prodrug thereof, or derivatives thereof) include, but are not limited to, reduction, elimination, or prevention of one or more markers that are characteristic of the pathology or disease (e.g., of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, βAPPα/βAPPβ ratio, βAPPα/Aβ40 ratio, βAPPα/Aβ42 ratio, etc.) and/or reduction, stabilization or reversal of one or more diagnostic criteria (e.g., clinical dementia rating (CDR)). Illustrative measures for improved neurological function include, but are not limited to the use of the mini-mental state examination (MMSE) or Folstein test (a questionnaire test that is used to screen for cognitive impairment), the General Practitioner Assessment of Cognition (GPCOG), a brief screening test for cognitive impairment described by Brodaty et al., (2002) *Geriatrics Society* 50(3): 530-534, and the like.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

The phrase "cause to be administered" refers to the actions taken by a medical professional (e.g., a physician), or a person prescribing and/or controlling medical care of a subject, that control and/or determine, and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

A "derivative" of a compound means a chemically modified compound wherein the chemical modification takes place at one or more functional groups of the compound. The derivative however, is expected to retain, or enhance, the pharmacological activity of the compound from which it is derived and/or to reduce undesired side effects of the compound when administered to a mammal.

Generally, reference to a certain element such as hydrogen or H is meant to include all isotopes of that element. For example, if an R group is defined to include hydrogen or H, it also includes deuterium and tritium. Accordingly, isotopically labeled compounds are within the scope of this invention.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

The term "alkyl" includes both branched and straight chain alkyl groups. Typical alkyl groups are methyl, ethyl, n-propyl, isopropyl (iPr), n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl and the like.

As used herein, for example, "$C_{0-6}$ alkyl" is used to mean an alkyl having 0-6 carbons—that is 0, 1, 2, 3, 4, 5 or 6 carbons in a straight or branched configuration. An alkyl having no carbon is hydrogen when the alkyl is a terminal group. An alkyl having no carbon is a direct bond when the alkyl is a bridging (connecting) group. Non-limiting examples of alkyl groups include those with 0-1 carbon, 0-2 carbons, 0-3 carbons, 0-4 carbons, 0-5 carbons, 0-6 carbons, 1-2 carbons, 1-3 carbons, 1-4 carbons, 1-5 carbons, 1-6 carbons, 2-3 carbons, 2-4 carbons, 2-5 carbons, 2-6 carbons, 3-4 carbons, 3-5 carbons, 3-6 carbons, 4-5 carbons, 4-6 carbons, 5-6 carbons, 5 carbons or 6 carbons. These examples may be referred to, respectively, as $C_{0-1}$ alkyl, $C_{0-2}$ alkyl, $C_{0-3}$ alkyl, respectively, etc.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "aminoalkyl" refers to an amino derivative of an alkyl radical.

The term "halo" or "halogen" refers to fluoro, chloro, bromo or iodo.

The term "aryl" refers to phenyl or naphthyl which may be optionally substituted. Typical aryl groups include, but are not limited to, phenyl, 4-chlorophenyl, 4-fluorophenyl, 4-bromophenyl, 3-chlorophenyl, 3-fluorophenyl, 3-nitrophenyl, 3-(trifluoromethyl)phenyl, 2-methoxyphenyl, 2-methylphenyl, 3-methylphenyl, 4-methylphenyl, 4-ethylphenyl, 2-methyl-3methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, 2-iodo-4-methylphenyl, and the like.

The terms "heteroaryl" or "hetaryl" refer to a substituted or unsubstituted 3-10 membered unsaturated ring containing one, two, three or four heteroatoms, preferably one or two heteroatoms independently selected from oxygen, nitrogen and sulfur or to a bicyclic unsaturated ring system containing up to 10 atoms including at least one heteroatom selected from oxygen, nitrogen and sulfur. Examples of heteroaryls include, but are not limited to, 2-pyridinyl (synonym: 2-pyridyl), 3-pyridinyl (synonym: 3-pyridyl) or 4-pyridinyl (synonym: 4-pyridyl), pyrazinyl, 2-, 4-, or 5-pyrimidinyl, pyridazinyl, triazolyl, tetrazolyl, imidazolyl, 2- or 3-thienyl (synonym: thiophenyl), 2- or 3-furyl (synonym: furanyl), pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. In certain embodiments the heterocyclic ring may be optionally substituted with up to two substituents.

The term aminoaryl" refers to an amino substituted heteroaryl.

The term "phenoxide" is a conjugate base of phenol and can be synthesized by mixing phenol with a base (e.g. sodium hydride, sodium hydroxide etc.)

The term "substantially pure" when used with respect to enantiomers indicates that one particular enantiomer (e.g. an S enantiomer or an R enantiomer) is substantially free of its stereoisomer. In various embodiments substantially pure indicates that a particular enantiomer is at least 70%, or at least 80%, or at least 90%, or at least 95%, or at least 98%, or at least 99% of the purified compound. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (see, e.g., Stereochemistry of Carbon Compounds, (1962) by E. L. Eliel, McGraw Hill; Lochmuller (1975) *J. Chromatogr.*, 113(3): 283-302). Racemic mixtures of chiral compounds of the can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

DETAILED DESCRIPTION

In various embodiments novel allosteric antagonists of the CRFR1 receptor are provided. It was a surprising discovery that allosteric CRFR1 receptor antagonist are effective to modulate p-Tau levels in Alzheimer's disease (AD) models. Without being bound to a particular theory, it is believed that being allosteric CRFR1 antagonists, the compounds described herein have greater selectivity for the CRFR1 receptor and hence a greater safety profile compared to direct CRFR1 receptor antagonists.

As evidenced by their ability to modulate p-tau levels in AD animal models, it is believed the compounds described herein find utility, inter alia, in the prophylaxis and/or treatment of pathologies characterized by an amyloidogenic process.

Figure 1:
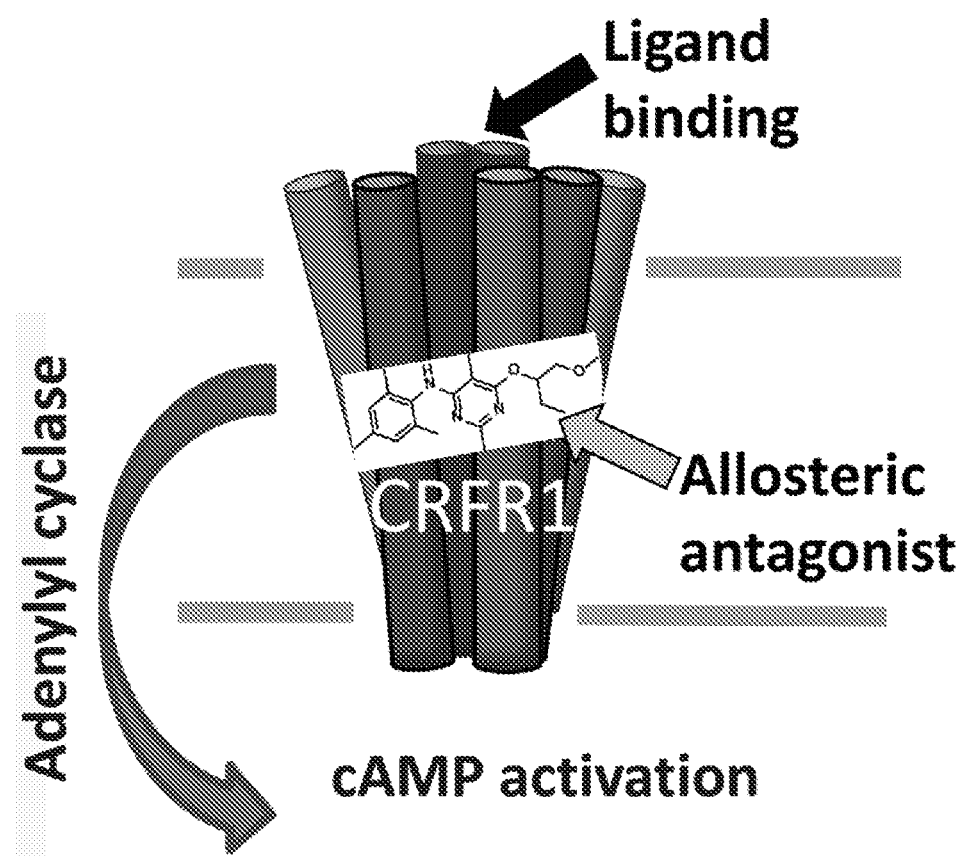
FIG. 1 schematically illustrates action of corticotropin-releasing factor 1 (CRF1) antagonists that interact with an allosteric site on the CRF1 receptor (CRFR1).

The T series of compounds described herein (e.g., T33, T34, T35, T36, T37, T38, T39, T40, T41, T42, T43, T44, T45, T46, T47, T48, T49, T50, T51, T52, T53, T54, T55, T56, T57, T58, T59, T60, T61) are corticotropin-releasing factor 1 (CRF1) antagonists that interact with an allosteric site on the CRF1 receptor (CRFR1) (see, e.g., FIG. 1). Chronic stress can result in increased phosphorylation of the microtubule-stabilizing protein tau, and this hyperphosphorylation of tau (ptau) is associated with the formation of the neurofibrillary tangles that are a hallmark of Alzheimer's disease (AD). Many studies indicate there is a closer association of neurofibrillary tangle load than amyloid plaque load with cognitive decline in AD. In addition to AD, increases in ptau and tangle formation occur in tauopathies, neurodegenerative diseases distinct from AD.

Corticotropin-releasing hormone or factor (CRH, CRF) is released in response to stress and binds the CRFR1 receptor, ultimately triggering increased phosphorylation of tau. Direct ligand-site antagonists exist and have been shown to lower ptau. An allosteric antagonist does not bind at the ligand binding site, but rather a site remote from it; it may either prevent or decreases effective ligand binding by inducing a conformational change or disrupt signaling. This type of antagonism may be more specific for receptor type and/or ligand and this specificity/selectivity may reduce off-target effects of the antagonist.

Like other CRFR1 receptor antagonists, it is believed the compounds described herein (e.g., the "T series" compounds) also find utility in the treatment of various psychiatric disorders and neurological diseases including depression, anxiety-related disorders and feeding disorders, and in the etiology and pathophysiology of Parkinson's disease, Huntington's disease, progressive supranuclear palsy and amyotrophic lateral sclerosis. Additionally, it is believed the compounds described herein can be used in the prophylaxis and treatment of conditions such as Cushing's disease, hypertension, stroke, irritable bowel syndrome, stress-induced gastric ulceration, premenstrual syndrome, sexual dysfunction, premature labor, inflammatory disorders, allergies, multiple sclerosis, visceral pain, sleep disorders, pituitary tumors or ectopic pituitary-derived tumors, chronic fatigue syndrome and fibromyalgia.

With respect to amyloidogenic pathologies such as Alzheimer's disease (and amyloidogenic MCI), it is noted that the prevailing view of Alzheimer's disease (AD) is that amyloid-beta peptides cause toxicity through chemical and physical mechanisms, such as metal binding, ROS production, and membrane damage. Our data suggest an alternative view of AD as an imbalance in physiological signaling mediated by APP. In this model, Aβ functions physiologically as an anti-trophin, and Aβ binding to APP induces the formation of peptides that mediate neurite retraction and cell death (see, e.g., Lu et al., (2000) *Nat. Med.*, 6: 397-404). This imbalance in physiological signaling can result in increased processing of APP by an amyloidogenic pathway and reduced processing of APP by a non-amyloidogenic pathway.

In the amyloidogenic pathway is initiated when β-secretase cleaves APP at the amino terminus of the Aβ, thereby releasing the APPsβ ectodomain ("sAPPβ"). In contrast, in the non-amyloidogenic pathway, APP is first cleaved by α-secretase within the Aβ sequence, releasing the APPsα ectodomain ("sAPPα"). APP processing by the nonamyloidogenic and amyloidogenic pathways is known in the art and reviewed, e.g., by Xu (2009) *J Alzheimer's Dis.* 16(2):211-224 and De Strooper et al. (2010) *Nat. Rev. Neurol.* 6(2) 99-107.

Without being bound to a particular theory, it is believe the compounds described herein can be used, inter alia, to promote processing of APP by the non-amyloidogenic pathway and/or reduce or inhibit processing of APP by the amyloidogenic pathway.

Accordingly, in various embodiments compositions and methods are provided for mitigating in a mammal one or more symptoms associated with a disease characterized by amyloid deposits in the brain (e.g., Alzheimer's disease, Cerebrovascular dementia, Parkinson's disease, Huntington's disease, Cerebral amyloid angiopathy, etc.), or delaying or preventing the onset of symptoms. Compositions and methods are also provided for reducing the risk, lessening the severity, or delaying the progression or onset of a disease characterized by beta-amyloid deposits in the brain of a mammal (e.g., Alzheimer's disease, Cerebrovascular dementia, Parkinson's disease, Huntington's disease, Cerebral amyloid angiopathy, etc.). In certain embodiments compositions and methods are provided for preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease in a mammal. In certain embodiments compositions and methods are provided for promoting the processing of amyloid precursor protein (APP) by the non-amyloidogenic pathway as characterized by increasing sAPPα and/or the sAPPα/Aβ42 ratio in a mammal.

Figure 2:
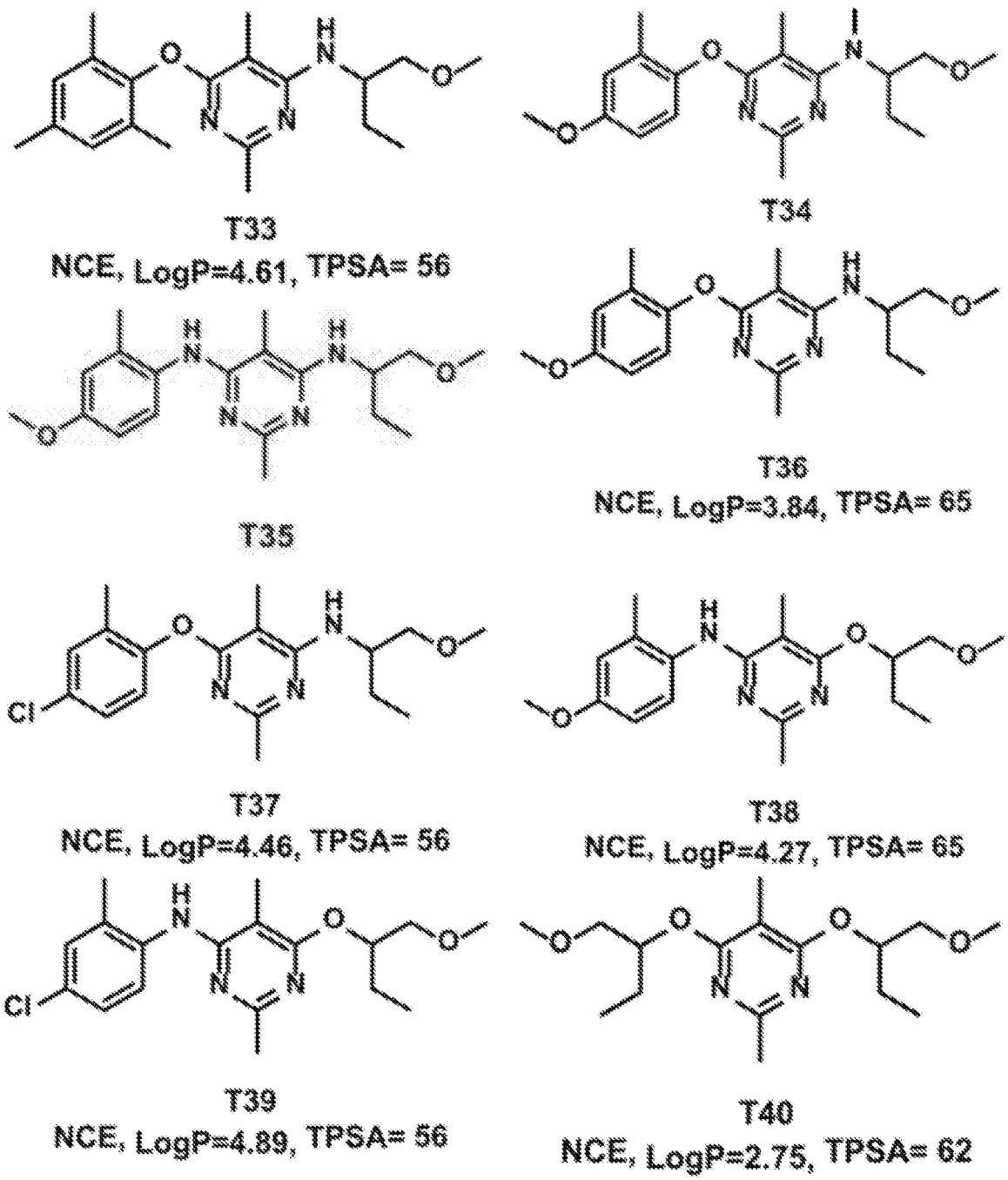
FIG. 2 illustrative CRFR1 receptor antagonists.

Accordingly, in various embodiments, the use of one or more CRFR1 receptor antagonists described herein (see, e.g., Formula I, FIG. 2, Table 5, and the like) or formulations thereof and/or an enantiomer thereof, and/or a mixture of enantiomers, and/or a mixture of two or more diastereomers thereof, and/or a pharmaceutically acceptable salt, ester, amide, solvate, hydrate, or prodrug thereof, and/or a derivative thereof for the modulation, and in particular in the reduction of amyloidogenic pathologies (e.g., MCI, Alzheimer's disease, age-related macular degeneration (AMD), Cerebrovascular dementia, Parkinson's disease, and the like) is provided. In certain embodiments, the compounds and/or formulations described herein are used to prevent or delay the onset of a pre-Alzheimer's condition and/or cognitive dysfunction, and/or to ameliorate one or more symptoms of a pre-Alzheimer's condition and/or cognitive dysfunction, and/or to prevent or delay the progression of a pre-Alzheimer's condition or cognitive dysfunction to Alzheimer's disease. In certain embodiments, the compounds and formulations described herein are used in a method of mitigating in a mammal one or more symptoms associated with a disease characterized by amyloid deposits in the brain, or delaying or preventing the onset of said symptoms. In certain embodiments, methods of reducing the risk, lessening the severity, or delaying the progression or onset of a disease characterized by beta-amyloid deposits in the brain of a mammal are also provided. In addition, methods of promoting the processing of amyloid precursor protein (APP) by the non-amyloidogenic pathway in a mammal are provided.

Typically each of these methods involve administering one or more CRFR1 receptor antagonist(s) described herein compound or formulations thereof and/or an enantiomer thereof, and/or a mixture of enantiomers thereof, and/or a mixture of two or more diastereomers thereof, and/or a pharmaceutically acceptable salt, ester, amide, solvate, hydrate, or prodrug thereof, and/or a derivative thereof, in an amount sufficient to produce the desired activity (e.g., mitigating one or more symptoms associated with a disease characterized by amyloid deposits in the brain, or delaying or preventing the onset of said symptoms, and/or reducing the risk, lessening the severity, or delaying the progression or onset of a disease characterized by beta-amyloid deposits in the brain of a mammal, and/or promoting the processing of amyloid precursor protein (APP) by the non-amyloidogenic pathway).

While the methods described herein are detailed primarily in the context of mild cognitive impairment (MCI) and Alzheimer's disease (AD) it is believed they can apply equally to other pathologies characterized by amyloidosis. Illustrative, but non-limiting list of conditions characterized by amyloid plaque formation are shown in Table 1.

TABLE 1

Illustrative, but non-limiting pathologies characterized by amyloid formation/deposition.

| Disease | Characteristic Protein | Abbreviation |
|---|---|---|
| Alzheimer's disease | Beta amyloid | Aβ |
| Diabetes mellitus type 2 | IAPP (Amylin) | AIAPP |
| Parkinson's disease | Alpha-synuclein | |
| Transmissible spongiform encephalopathy e.g. Bovine spongiform encephalopathy | Prion | APrP |
| Huntington's Disease | Huntingtin | |
| Medullary carcinoma of the thyroid | Calcitonin | ACal |
| Cardiac arrhythmias, Isolated atrial amyloidosis | Atrial natriuretic factor | AANF |
| Atherosclerosis | Apolipoprotein AI | AApoA1 |
| Rheumatoid arthritis | Serum amyloid A | AA |
| Aortic medial amyloid | Medin | AMed |
| Prolactinomas | Prolactin | APro |
| Familial amyloid polyneuropathy | Transthyretin | ATTR |
| Hereditary non-neuropathic systemic amyloidosis | Lysozyme | ALys |

TABLE 1-continued

Illustrative, but non-limiting pathologies characterized by amyloid formation/deposition.

| Disease | Characteristic Protein | Abbreviation |
|---|---|---|
| Dialysis related amyloidosis | Beta 2 microglobulin | Aβ2M |
| Finnish amyloidosis. | Gelsolin | AGel |
| Lattice corneal dystrophy | Keratoepithelin | AKer |
| Cerebral amyloid angiopathy | Beta amyloid[15] | Aβ |
| Cerebral amyloid angiopathy (Icelandic type) | Cystatin | ACys |
| systemic AL amyloidosis | Immunoglobulin light chain AL[14] | AL |
| Sporadic Inclusion Body Myositis | S-IBM | none |
| Age-related macular degeneration (AMD) | | |
| Cerebrovascular dementia | | |

Allosteric CRFR1 Receptor Antagonists.

As explained above, it was a surprising discovery that the CRFR1 receptor antagonists described herein, in particular allosteric CRFR1 receptor antagonists described herein are effective to modulate p-Tau levels in Alzheimer's disease (AD) models. In certain embodiments the CRFR1 receptor antagonist is a compound according to Formula I:

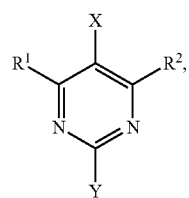

or a pharmaceutically acceptable salt, ester, amide, or prodrug thereof, where X and Y are independently selected from the group consisting of Me ($CH_3$), H, $CF_3$, deuterated methyl, and halogen; $R^1$ is, or comprises, a moiety selected from the group consisting of linear or substituted aminoalkyl, substituted phenoxide, unsubstituted phenoxide, substituted alkoxide, unsubstituted alkoxide, substituted aminoaryl, unsubstituted aminoaryl, unsubstituted aminoheteroaryl, and substituted aminoheteroaryl; and $R^2$ is, or comprises, a moiety selected from the group consisting of linear or substituted alkoxide, phenoxide, substituted aminoalkyl, unsubstituted aminoalkyl, and pyran (e.g., tetrahydro-2H-pyran-4-oxide). In certain embodiments $R^1$ is selected from the group consisting of linear or substituted aminoalkyl, substituted or unsubstituted, aminoaryl, aminoheteroaryl, substituted aminoheteroaryl, and $R^2$ is selected from the group consisting of linear or substituted alkoxide or phenoxide. In certain embodiments X is $CH_3$, or Y is $CH_3$, or both X and Y are $CH_3$. In various embodiments the compound is an allosteric CRFR1 receptor antagonist.

In certain embodiments X is $CH_3$, and/or Y is $CH_3$. In certain embodiments $R^2$ is

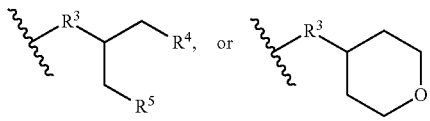

where $R^3$ is selected from the group consisting of O, NH, and $NCH_3$; $R^4$ is selected from the group consisting of $OCH_3$, $CH_3$, $CH_2OH$; and $R^5$ is selected from the group consisting of $CH_3$, and $OCH_3$. In certain embodiments $R^2$ is

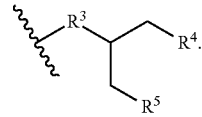

In certain embodiments $R^4$ is $OCH_3$, in certain embodiments $R^4$ is $CH_3$, and in certain embodiments, $R^4$ is $CH_2OH$. In certain embodiments $R^5$ is $CH_3$, in certain embodiments, and in certain embodiments, $R^5$ is $OCH_3$. In certain embodiments $R^2$ is selected from the group consisting of

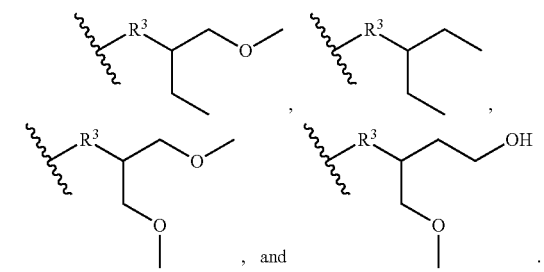

In certain embodiments $R^2$ is

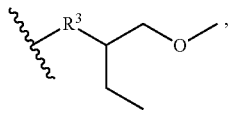

while in other embodiments, $R^2$ is

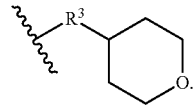

In certain embodiments of the foregoing embodiments, $R^3$ is O, while in other embodiments, $R^3$ is NH, and in other embodiments, $R^3$ is $NCH_3$.

In certain embodiments $R^1$ is

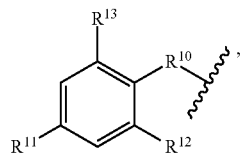

where $R^{10}$ is NH or O; $R^{11}$ is selected from the group consisting of H, $CH_3$, $OCH_3$, halogen, $CH_2NH_2$, CN, and $CR^8{}_3$ where $R^8$ is halogen (e.g., Cl or F); $R^{12}$ is selected from the group consisting of H, $CH_3$, or halogen; and $R^{13}$ is selected from the group consisting of $CH_3$, halogen, and $CR^9{}_3$ where $R^9$ is halogen (e.g., Cl or F). In certain embodiments $R^{11}$ is H, or in certain embodiments, $R^{11}$ is $CH_3$, or in certain embodiments, $R^{11}$ is $OCH_3$, or in certain embodiments $R^{11}$ is halogen (e.g., Cl or F), or in certain embodiments, $R^{11}$ is $CH_2NH_2$, or in certain embodiments, $R^{11}$ is CN, or in certain embodiments, $R^{11}$ is $CF_3$.

In certain embodiments $R^{12}$ is H, or in certain embodiments $R^{12}$ is halogen, or in certain embodiments $R^{12}$ is $CH_3$. In certain embodiments $R^1$ is selected from the group consisting of

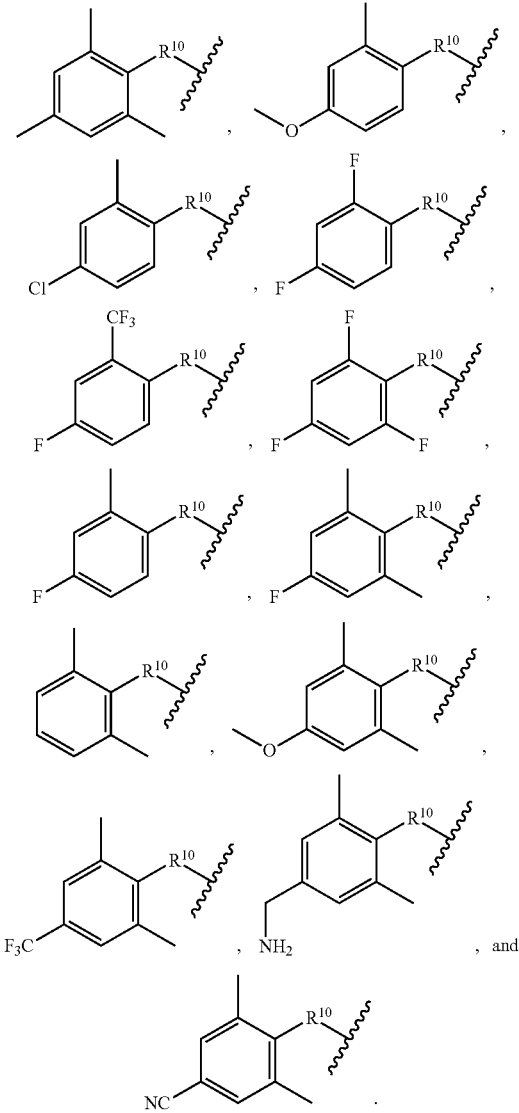

In certain embodiments $R^1$ is

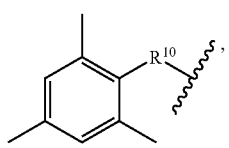

while in certain other embodiments, $R^1$ is

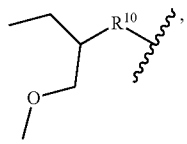

where $R^{10}$ is NH or O, and in certain other embodiments, $R^1$ is

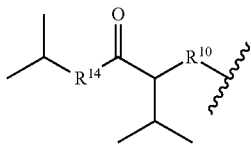

where $R^{10}$ is NH or O; and $R^{14}$ is NH or O. In certain embodiments $R^1$ is selected from the group consisting of

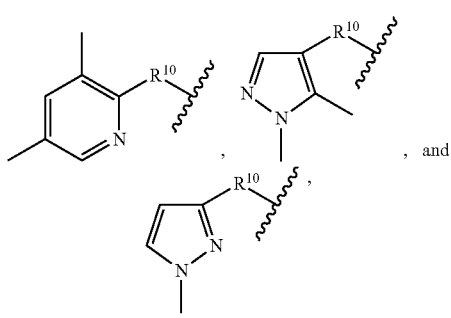

where $R^{10}$ is NH or O. In certain embodiments $R^{10}$ is NH. In certain embodiments $R^{10}$ is O. In certain embodiments $R^1$ is

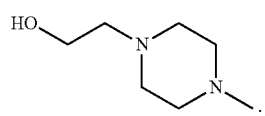

In certain embodiments the compound is selected from the group consisting of T41, T33, T34, T35, T36, T37, T38, T39, T42, T43, T44, T45, T46, T47, T48, T49, T50, T51, T52, T55, T56, and T57, or a pharmaceutically acceptable salt, ester, amide, solvate, or prodrug thereof. In certain embodiments the compound comprises T41, or a pharmaceutically acceptable salt, ester, amide, solvate, or prodrug thereof. In certain embodiments the compound is selected from the group consisting of T53, and T54 or a pharmaceutically acceptable salt, ester, amide, solvate, or prodrug thereof. In certain embodiments the compound is selected from the group consisting of T58, and T59 or a pharmaceutically acceptable salt, ester, amide, solvate, or prodrug thereof. In certain embodiments the compound is T60 or a pharmaceutically acceptable salt, ester, amide, solvate, or prodrug thereof. In certain embodiments the compound is T61 or a pharmaceutically acceptable salt, ester, amide, solvate, or prodrug thereof. In certain embodiments compound comprises a compound according to a formula shown in FIG. 2, or a pharmaceutically acceptable salt, ester, amide, solvate, or prodrug thereof. In certain embodiments the compound is a substantially pure "R" enantiomer. In certain embodiments the compound is a substantially pure "S" enantiomer.

Methods of making the compounds described herein are illustrated in the examples provided herein. Using the teaching provided herein numerous variants and/or derivatives of the compound described herein will be readily synthesized by one of skill in the art.

Also included within the scope of the compositions and methods provided herein are the individual enantiomers of the compounds represented by the formulas shown herein (e.g., Formula (I)) or pharmaceutically acceptable salts thereof, as well as any wholly or partially racemic mixtures thereof. The compositions and methods also cover the individual enantiomers of the compounds represented by the formulas described herein or pharmaceutically acceptable salts thereof, as well as mixtures with diastereoisomers thereof in which one or more stereocenters are inverted. Unless otherwise stated, structures depicted herein are also meant to include compounds that differ only in the presence of one or more isotopically enriched atoms. For example, compounds having the present structure except for the replacement of a hydrogen atom by a deuterium or tritium, or the replacement of a carbon atom by a $^{13}C$- or $^{14}C$- enriched carbon are within the scope of the invention. Formula (I) also implicitly includes any tautomeric forms of the compounds included, even though those forms may not be expressly depicted by the chemical formula.

Subjects Who can Benefit from the Present Methods

Subjects/patients amenable to treatment using the methods described herein include individuals at risk of disease (e.g., a pathology characterized by amyloid plaque formation) but not showing symptoms, as well as subjects presently showing symptoms. Accordingly, certain subjects include subjects at increased risk for the onset of a pre-Alzheimer's condition and/or cognitive dysfunction (e.g., MCI), and/or subjects diagnosed as having a pre-Alzheimer's condition and/or cognitive dysfunction (e.g., MCI).

Accordingly, in various embodiments, therapeutic and/or prophylactic methods are provided that utilize the CRFR1 receptor antagonists (or formulations thereof and/or an enantiomer thereof, a mixture of enantiomers, or a mixture of two or more diastereomers thereof; or a pharmaceutically acceptable salt, ester, amide, solvate, hydrate, or prodrug thereof, or a derivative thereof) are provided. Typically the methods involve administering one or more CRFR1 receptor antagonists described herein and/or a formulation thereof to a subject (e.g., to a human in need thereof) in an amount sufficient/effective to realize the desired therapeutic or prophylactic result.

Prophylaxis

In certain embodiments, the CRFR1 receptor antagonists described herein (or enantiomer thereof, a mixture of enantiomers, or a mixture of two or more diastereomers thereof; or a pharmaceutically acceptable salt, ester, amide, solvate, hydrate, or prodrug thereof or derivatives thereof, and/or formulations comprising any of these) are utilized in various prophylactic contexts. Thus, for example, ion certain embodiments, the CRFR1 receptor antagonist(s) can be used to prevent or delay the onset of a pre-Alzheimer's cognitive dysfunction, and/or to ameliorate one more symptoms of a pre-Alzheimer's condition and/or cognitive dysfunction, and/or to prevent or delay the progression of a pre-Alzheimer's condition and/or cognitive dysfunction to Alzheimer's disease.

Accordingly in certain embodiments, the prophylactic methods described herein are contemplated for subjects identified as "at risk" and/or as having evidence of early MCI and/or early Alzheimer's Disease (AD) pathological changes, but who do not meet clinical criteria for MCI or dementia. Without being bound to a particular theory, it is believed that even this "preclinical" stage of the disease represents a continuum from completely asymptomatic individuals with biomarker evidence suggestive of AD-pathophysiological process(es) (abbreviated as AD-P, see, e.g., Sperling et al., (2011) *Alzheimer's & Dementia*, 1-13) at risk for progression to AD dementia to biomarker-positive individuals who are already demonstrating very subtle decline but not yet meeting standardized criteria for MCI (see, e.g., Albert et al., (2011) *Alzheimer's and Dementia*, 1-10 (doi: 10.1016/j.jalz.2011.03.008)).

This latter group of individuals might be classified as "not normal, not MCI" but can be designated "pre-symptomatic" or "pre-clinical or "asymptomatic" or "premanifest"). In various embodiments, this continuum of pre-symptomatic AD can also encompass (1) individuals who carry one or more apolipoprotein E (APOE) ε4 alleles who are known or believed to have an increased risk of developing AD dementia, at the point they are AD-P biomarker-positive, and (2) carriers of autosomal dominant mutations, who are in the presymptomatic biomarker-positive stage of their illness, and who will almost certainly manifest clinical symptoms and progress to dementia.

A biomarker model has been proposed in which the most widely validated biomarkers of AD-P become abnormal and likewise reach a ceiling in an ordered manner (see, e.g., Jack et al., (2010) *Lancet Neurol.*, 9: 119-128.). This biomarker model parallels proposed pathophysiological sequence of (pre-AD/AD), and is relevant to tracking the preclinical (asymptomatic) stages of AD (see, e.g., FIG. 3 in Sperling et al., (2011) *Alzheimer's & Dementia*, 1-13). Biomarkers of brain amyloidosis include, but are not limited to reductions in CSF A$\beta_{42}$ and increased amyloid tracer retention on positron emission tomography (PET) imaging. Elevated CSF tau is not specific to AD and is thought to be a biomarker of neuronal injury. Decreased fluorodeoxyglucose 18F (FDG) uptake on PET with a temporoparietal pattern of hypometabolism is a biomarker of AD-related synaptic dysfunction. Brain atrophy on structural magnetic resonance imaging (MRI) in a characteristic pattern involving the medial temporal lobes, paralimbic and temporoparietal cortices is a biomarker of AD-related neurodegeneration. Other markers include, but are not limited to volumetric MRI, FDG-PET, or plasma biomarkers (see, e.g., Vemuri et al., (2009) *Neurology*, 73: 294-301; Yaffe et al., (2011) *JAMA* 305: 261-266).

In certain embodiments, the subjects suitable for the prophylactic methods contemplated herein include, but are not limited to subject characterized as having asymptomatic cerebral amyloidosis. In various embodiments, these individuals have biomarker evidence of Aβ accumulation with elevated tracer retention on PET amyloid imaging and/or low Aβ42 in CSF assay, but typically no detectable evidence of additional brain alterations suggestive of neurodegeneration or subtle cognitive and/or behavioral symptomotology.

It is noted that currently available CSF and PET imaging biomarkers of Aβ primarily provide evidence of amyloid accumulation and deposition of fibrillar forms of amyloid. Data suggest that soluble or oligomeric forms of Aβ are likely in equilibrium with plaques, which may serve as reservoirs. In certain embodiments, it is contemplated that there is an identifiable preplaque stage in which only soluble forms of Aβ are present. In certain embodiments, it is contemplated that oligomeric forms of amyloid may be critical in the pathological cascade, and provide useful markers. In addition, early synaptic changes may be present before evidence of amyloid accumulation.

In certain embodiments, the subjects suitable for the prophylactic methods contemplated herein include, but are not limited to, subjects characterized as amyloid positive with evidence of synaptic dysfunction and/or early neurodegeneration. In various embodiments, these subjects have evidence of amyloid positivity and presence of one or more markers of "downstream" AD-P-related neuronal injury. Illustrative, but non-limiting markers of neuronal injury include, but are not limited to (1) elevated CSF tau or phospho-tau, (2) hypometabolism in an AD-like pattern (e.g., posterior cingulate, precuneus, and/or temporoparietal cortices) on FDG-PET, and (3) cortical thinning/gray matter loss in a specific anatomic distribution (e.g., lateral and medial parietal, posterior cingulate, and lateral temporal cortices) and/or hippocampal atrophy on volumetric MRI. Other markers include, but are not limited to fMRI measures of default network connectivity. In certain embodiments, early synaptic dysfunction, as assessed by functional imaging techniques such as FDG-PET and fMRI, can be detectable before volumetric loss. Without being bound to a particular theory, it is believed that amyloid-positive individuals with evidence of early neurodegeneration may be farther down the trajectory (e.g., in later stages of preclinical (asymptomatic) AD).

In certain embodiments, the subjects suitable for the prophylactic methods contemplated herein include, but are not limited to, subjects characterized as amyloid positive with evidence of neurodegeneration and subtle cognitive decline. Without being bound to a particular theory, it is believed that those individuals with biomarker evidence of amyloid accumulation, early neurodegeneration, and evidence of subtle cognitive decline are in the last stage of preclinical (asymptomatic) AD, and are approaching the border zone with clinical criteria for mild cognitive impairment (MCI). These individuals may demonstrate evidence of decline from their own baseline (particularly if proxies of cognitive reserve are taken into consideration), even if they still perform within the "normal" range on standard cognitive measures. Without being bound to a particular theory, it is believed that more sensitive cognitive measures, particularly with challenging episodic memory measures, may detect very subtle cognitive impairment in amyloid-positive individuals. In certain embodiments, criteria include, but are not limited to, self-complaint of memory decline or other subtle neurobehavioral changes.

As indicated above, subjects/patients amenable to prophylactic methods described herein include individuals at risk of disease (e.g., a pathology characterized by amyloid plaque formation such as MCI) but not showing symptoms, as well as subjects presently showing certain symptoms or markers. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein present methods are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, mutations in the APP gene, particularly mutations at position 717 and positions 670 and 671 referred to as the Hardy and Swedish mutations respectively (see, e.g., Hardy (1997) *Trends. Neurosci.*, 20: 154-159). Other markers of risk include mutations in the presenilin genes (PS1 and PS2), family history of AD, having the familial Alzheimer's disease (FAD) mutation, the APOE ε4 allele, hypercholesterolemia or atherosclerosis. Further susceptibility genes for the development of Alzheimer's disease are reviewed, e.g., in Sleegers, et al., (2010) *Trends Genet.* 26(2): 84-93.

In some embodiments, the subject is asymptomatic but has familial and/or genetic risk factors for developing MCI or Alzheimer's disease. In asymptomatic patients, treatment can begin at any age (e.g., 20, 30, 40, 50, years of age). Usually, however, it is not necessary to begin treatment until a patient reaches at least about 40, 50, 60, 70 or 80 years of age.

In some embodiments, the subject is one who exhibits symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include, but are not limited to measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/Aβ40 ratio, and sAPPα/Aβ42 ratio signify the presence of AD. In some embodiments, the subject or patient is clinically diagnosed as having MCI. Increased levels of neural thread protein (NTP) in urine and/or increased levels of α2-macroglobulin (α2M) and/or complement factor H (CFH) in plasma are also biomarkers of MCI and/or AD (see, e.g., Anoop et al., (2010) *Int. J. Alzheimer's Dis.* 2010:606802).

In certain embodiments, subjects amenable to treatment may have age-associated memory impairment (AAMI), or mild cognitive impairment (MCI). The methods described herein are particularly well-suited to the prophylaxis and/or treatment of MCI, particularly MCI characterized by an amyloidogenic process. In such instances, the methods can delay or prevent the onset of MCI, and or reduce one or more symptoms characteristic of MCI and/or delay or prevent the progression from MCI to early-, mid- or late-stage Alzheimer's disease, and/or reduce the ultimate severity of the disease.

Mild Cognitive Impairment (MCI)

In various embodiments, the CRFR1 receptor antagonist(s) described herein (e.g., or formulations thereof, and/or an enantiomer, a mixture of enantiomers, or a mixture of two or more diastereomers thereof, or a pharmaceutically acceptable salt, ester, amide, solvate, hydrate, or prodrug thereof or derivatives thereof) can be used for the treatment and/or prophylaxis of age-related cognitive decline and/or for the treatment and/or prophylaxis of mild cognitive impairment (MCI). Mild cognitive impairment, also known as incipient dementia, or isolated memory impairment) is a diagnosis given to individuals who have cognitive impairments beyond that expected for their age and education, but that typically do not interfere significantly with their daily activities (see, e.g., Petersen et al., (1999) *Arch. Neurol.* 56(3): 303-308). It is considered in many instances to be a boundary or transitional stage between normal aging and dementia. Although MCI can present with a variety of symptoms, when memory loss is the predominant symptom it is termed "amnestic MCI" and is can be a risk factor for Alzheimer's disease (see, e.g., Grundman et al., (2004) *Arch. Neurol.* 61(1): 59-66; and on the internet at en.wikipedia.org/wiki/Mild_cognitive_impairment-cite_note-Grundman-1). When individuals have impairments in domains other than memory it is often classified as non-amnestic single- or multiple-domain MCI and these individuals are believed to be more likely to convert to other dementias (e.g. dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al., (2006) *Arch. Neurol.*, 63(5): 665-72).

The diagnosis of MCI typically involves a comprehensive clinical assessment including clinical observation, neuroimaging, blood tests and neuropsychological testing. In certain embodiments, diagnostic criteria for MCI include, but are not limited to those described by Albert et al., (2011) *Alzheimer's & Dementia.* 1-10. As described therein, diagnostic criteria include (1) core clinical criteria that could be used by healthcare providers without access to advanced imaging techniques or cerebrospinal fluid analysis, and (2) research criteria that could be used in clinical research settings, including clinical trials. The second set of criteria incorporate the use of biomarkers based on imaging and cerebrospinal fluid measures. The final set of criteria for mild cognitive impairment due to AD has four levels of certainty, depending on the presence and nature of the biomarker findings.

In certain embodiments, clinical evaluation/diagnosis of MCI involves: (1) Concern reflecting a change in cognition reported by patient or informant or clinician (e.g., historical or observed evidence of decline over time); (2) Objective evidence of Impairment in one or more cognitive domains, typically including memory (e.g., formal or bedside testing to establish level of cognitive function in multiple domains); (3) Preservation of independence in functional abilities; (4) Not demented; and in certain embodiments, (5) An etiology of MCI consistent with AD pathophysiological processes. Typically vascular, traumatic, medical causes of cognitive decline are ruled out where possible. In certain embodiments, evidence of longitudinal decline in cognition is identified, when feasible. Diagnosis is reinforced by a history consistent with AD genetic factors, where relevant.

With respect to impairment in cognitive domain(s), there should be evidence of concern about a change in cognition, in comparison with the person's previous level. There should be evidence of lower performance in one or more cognitive domains that is greater than would be expected for the patient's age and educational background. If repeated assessments are available, then a decline in performance should be evident over time. This change can occur in a variety of cognitive domains, including memory, executive function, attention, language, and visuospatial skills. An impairment in episodic memory (e.g., the ability to learn and retain new information) is seen most commonly in MCI patients who subsequently progress to a diagnosis of AD dementia.

With respect to preservation of independence in functional abilities, it is noted that persons with MCI commonly have mild problems performing complex functional tasks which they used to perform shopping. They may take more time, be less efficient, and make more errors at performing such activities than in the past. Nevertheless, they generally maintain their independence of function in daily life, with minimal aids or assistance.

With respect to dementia, the cognitive changes should be sufficiently mild that there is no evidence of a significant impairment in social or occupational functioning. If an individual has only been evaluated once, change will be inferred from the history and/or evidence that cognitive performance is impaired beyond what would have been expected for that individual.

Cognitive testing is optimal for objectively assessing the degree of cognitive impairment for an individual. Scores on cognitive tests for individuals with MCI are typically 1 to 1.5 standard deviations below the mean for their age and education matched peers on culturally appropriate normative data (e.g., for the impaired domain(s), when available).

Episodic memory (i.e., the ability to learn and retain new information) is most commonly seen in MCI patients who subsequently progress to a diagnosis of AD dementia. There are a variety of episodic memory tests that are useful for identifying those MCI patients who have a high likelihood of progressing to AD dementia within a few years. These tests typically assess both immediate and delayed recall, so that it is possible to determine retention over a delay. Many, although not all, of the tests that have proven useful in this regard are wordlist learning tests with multiple trials. Such tests reveal the rate of learning over time, as well as the maximum amount acquired over the course of the learning trials. They are also useful for demonstrating that the individual is, in fact, paying attention to the task on immediate recall, which then can be used as a baseline to assess the relative amount of material retained on delayed recall. Examples of such tests include (but are not limited to: the Free and Cued Selective Reminding Test, the Rey Auditory Verbal Learning Test, and the California Verbal Learning Test. Other episodic memory measures include, but are not limited to: immediate and delayed recall of a paragraph such as the Logical Memory I and II of the Wechsler Memory Scale Revised (or other versions) and immediate and delayed recall of nonverbal materials, such as the Visual Reproduction subtests of the Wechsler Memory Scale-Revised I and II.

Because other cognitive domains can be impaired among individuals with MCI, it is desirable to examine domains in addition to memory. These include, but are not limited to executive functions (e.g., set-shifting, reasoning, problem-solving, planning), language (e.g., naming, fluency, expressive speech, and comprehension), visuospatial skills, and attentional control (e.g., simple and divided attention). Many clinical neuropsychological measures are available to assess these cognitive domains, including (but not limited to the Trail Making Test (executive function), the Boston Naming Test, letter and category fluency (language), figure copying (spatial skills), and digit span forward (attention).

As indicated above, genetic factors can be incorporated into the diagnosis of MCI. If an autosomal dominant form of AD is known to be present (e.g., mutation in APP, PS1, PS2), then the development of MCI is most likely the precursor to AD dementia. The large majority of these cases develop early onset AD (e.g., onset below 65 years of age).

In addition, there are genetic influences on the development of late onset AD dementia. For example, the presence of one or two ε4 alleles in the apolipoprotein E (APOE) gene is a genetic variant broadly accepted as increasing risk for late-onset AD dementia. Evidence suggests that an individual who meets the clinical, cognitive, and etiologic criteria for MCI, and is also APOE ε4 positive, is more likely to progress to AD dementia within a few years than an individual without this genetic characteristic. It is believed that additional genes play an important, but smaller role than APOE and also confer changes in risk for progression to AD dementia (see, e.g., Bertram et al., (2010) *Neuron,* 21: 270-281).

In certain embodiments, subjects suitable for the prophylactic methods described herein (e.g., administration of a CRFR1 receptor antagonist(s) described herein, and/or an enantiomer, a mixture of enantiomers, or a mixture of two or more diastereomers thereof; or a pharmaceutically acceptable salt, ester, amide, solvate, hydrate, or prodrug thereof or derivatives thereof, and/or a formulation comprising any of these) include, but need not be limited to subjects identified having one or more of the core clinical criteria described above and/or subjects identified with one or more "research criteria" for MCI, e.g., as described below.

"Research criteria" for the identification/prognosis of MCI include, but are not limited to biomarkers that increase the likelihood that MCI syndrome is due to the pathophysiological processes of AD. Without being bound to a particular theory, it is believed that the conjoint application of clinical criteria and biomarkers can result in various levels of certainty that the MCI syndrome is due to AD pathophysiological processes. In certain embodiments, two categories of biomarkers have been the most studied and applied to clinical outcomes are contemplated. These include "Aβ" (which includes CSF Aβ$_{42}$ and/or PET amyloid imaging) and "biomarkers of neuronal injury" (which include, but are not limited to CSF tau/p-tau, hippocampal, or medial temporal lobe atrophy on MM, and temporoparietal/precuneus hypometabolism or hypoperfusion on PET or SPECT).

Without being bound to a particular theory, it is believed that evidence of both Aβ, and neuronal injury (either an increase in tau/p-tau or imaging biomarkers in a topographical pattern characteristic of AD), together confers the highest probability that the AD pathophysiological process is present. Conversely, if these biomarkers are negative, this may provide information concerning the likelihood of an alternate diagnosis. It is recognized that biomarker findings may be contradictory and accordingly any biomarker combination is indicative (an indicator) used on the context of a differential diagnosis and not itself dispositive. It is recognized that varying severities of an abnormality may confer different likelihoods or prognoses, that are difficult to quantify accurately for broad application.

For those potential MCI subjects whose clinical and cognitive MCI syndrome is consistent with AD as the etiology, the addition of biomarker analysis effects levels of certainty in the diagnosis. In the most typical example in which the clinical and cognitive syndrome of MCI has been established, including evidence of an episodic memory disorder and a presumed degenerative etiology, the most likely cause is the neurodegenerative process of AD. However, the eventual outcome still has variable degrees of certainty. The likelihood of progression to AD dementia will vary with the severity of the cognitive decline and the nature of the evidence suggesting that AD pathophysiology is the underlying cause. Without being bound to a particular theory it is believed that positive biomarkers reflecting neuronal injury increase the likelihood that progression to dementia will occur within a few years and that positive findings reflecting both Ab accumulation and neuronal injury together confer the highest likelihood that the diagnosis is MCI due to AD.

A positive Aβ biomarker and a positive biomarker of neuronal injury provide an indication that the MCI syndrome is due to AD processes and the subject is well suited for the methods described herein (e.g., treatment with a CRFR1 receptor antagonist described herein).

A positive Aβ biomarker in a situation in which neuronal injury biomarkers have not been or cannot be tested or a positive biomarker of neuronal injury in a situation in which Aβ biomarkers have not been or cannot be tested indicate an intermediate likelihood that the MCI syndrome is due to AD. Such subjects are believed to be well suited for the methods described herein Negative biomarkers for both Aβ and neuronal injury suggest that the MCI syndrome is not due to AD. In such instances the subjects may not be well suited for the methods described herein.

There is evidence that magnetic resonance imaging can observe deterioration, including progressive loss of gray matter in the brain, from mild cognitive impairment to full-blown Alzheimer disease (see, e.g., Whitwell et al., (2008) *Neurology* 70(7): 512-520). A technique known as PiB PET imaging is used to clearly show the sites and shapes of beta amyloid deposits in living subjects using a C11 tracer that binds selectively to such deposits (see, e.g., Jack et al., (2008) *Brain* 131(Pt 3): 665-680).

In certain embodiments, MCI is typically diagnosed when there is 1) Evidence of memory impairment; 2) Preservation of general cognitive and functional abilities; and 3) Absence of diagnosed dementia.

In certain embodiments, MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The information to make each rating is obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia.

An illustrative CDR table is shown in Table 2.

TABLE 2

Illustrative clinical dementia rating (CDR) table.

| | Impairment: | | | | |
|---|---|---|---|---|---|
| CDR: | None 0 | Questionable 0.5 | Mild 1 | Moderate 2 | Severe 3 |
| Memory | No memory loss or slight inconsistent forgetfulness | Consistent slight forgetfulness; partial recollection of events "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home Appears well enough to be taken to functions outside a family home | Appears too ill to be taken to functions outside a family home. |
| Home and Hobbies | Life at home, hobbies, and intellectual interests well maintained | Life at home, hobbies, and intellectual interests slightly impaired | Mild bit definite impairment of function at home; more difficult chores abandoned; more complicated hobbies and interests abandoned | Only simple chores preserved; very restricted interests, poorly maintained | No significant function in home |
| Personal Care | Fully capable of self-care | | Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In certain embodiments, administration of one or more agents described herein (e.g., a CRFR1 receptor antagonist described herein, and/or an enantiomer, a mixture of enantiomers, or a mixture of two or more diastereomers thereof; or a pharmaceutically acceptable salt, ester, amide, solvate, hydrate, or prodrug thereof or derivative thereof, or a formulation comprising any of the preceding) is deemed effective when there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al., (2004) *Arch Neurol* 61: 59-66, report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemory cognitive measures included in the battery. Tests of learning, attention, perceptual speed, category fluency, and executive function may be impaired in patients with MCI, but these are far less prominent than the memory deficit.

Alzheimer's Disease (AD).

In certain embodiments, the CRFR1 receptor antagonists described herein (and/or an enantiomer, a mixture of enantiomers, or a mixture of two or more diastereomers thereof, or a pharmaceutically acceptable salt, ester, amide, solvate, hydrate, or prodrug thereof or derivative thereof) and/or formulations thereof are contemplated for the prophylaxis or therapeutic treatment of Alzheimer's disease. In such instances the methods described herein are useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease, and/or prevent or delay the progression from an early stage of Alzheimer's disease to a later stage of Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments, subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al., (1984) *Neurology* 34(7): 939-944. According to these criteria, the presence of cognitive impairment and a suspected dementia syndrome should be confirmed by neuropsychological testing for a clinical diagnosis of possible or probable AD. However, histopathologic confirmation (microscopic examination of brain tissue) is generally used for a dispositive diagnosis. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al., (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al., (1984) *Am. J. Psychiatr.*, 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al., supra). Any score greater than or equal to 25 points (out of 30) is effectively normal (intact). Below this, scores can indicate severe (≤9 points), moderate (10-20 points) or mild (21-24 points) Alzheimer's disease.

Alzheimer's disease can be broken down into various stages including: 1) Moderate cognitive decline (mild or early-stage Alzheimer's disease), 2) Moderately severe cognitive decline (moderate or mid-stage Alzheimer's disease), 3) Severe cognitive decline (moderately severe or mid-stage Alzheimer's disease), and 4) Very severe cognitive decline (severe or late-stage Alzheimer's disease) as shown in Table 3.

TABLE 3

Illustrative stages of Alzheimer's disease

Moderate Cognitive Decline (Mild or early stage AD)

At this stage, a careful medical interview detects clear-cut deficiencies in the following areas:
Decreased knowledge of recent events.
Impaired ability to perform challenging mental arithmetic. For example, to count backward from 100 by 7s.

TABLE 3-continued

Illustrative stages of Alzheimer's disease

Decreased capacity to perform complex tasks, such as marketing, planning dinner for guests, or paying bills and managing finances.
Reduced memory of personal history.
The affected individual may seem subdued and withdrawn, especially in socially or mentally challenging situations.
Moderately severe cognitive decline (Moderate or mid-stage Alzheimer's disease)

Major gaps in memory and deficits in cognitive function emerge. Some assistance with day-to-day activities becomes essential. At this stage, individuals may:
Be unable during a medical interview to recall such important details as their current address, their telephone number, or the name of the college or
high school from which they graduated.
Become confused about where they are or about the date, day of the week or season.
Have trouble with less challenging mental arithmetic; for example, counting backward from 40 by 4s or from 20 by 2s.
Need help choosing proper clothing for the season or the occasion.
Usually retain substantial knowledge about themselves and know their own name and the names of their spouse or children.
Usually require no assistance with eating or using the toilet.
Severe cognitive decline (Moderately severe or mid-stage Alzheimer's disease)

Memory difficulties continue to worsen, significant personality changes may emerge, and affected individuals need extensive help with daily activities. At this stage, individuals may:
Lose most awareness of recent experiences and events as well as of their surroundings.
Recollect their personal history imperfectly, although they generally recall their own name.
Occasionally forget the name of their spouse or primary caregiver but generally can distinguish familiar from unfamiliar faces.
Need help getting dressed properly; without supervision, may make such errors as putting pajamas over daytime clothes or shoes on wrong feet.
Experience disruption of their normal sleep/waking cycle.
Need help with handling details of toileting (flushing toilet, wiping and disposing of tissue properly).
Have increasing episodes of urinary or fecal incontinence.
Experience significant personality changes and behavioral symptoms, including suspiciousness and delusions (for example, believing that their caregiver is an impostor); hallucinations (seeing or hearing things that are not really there); or compulsive, repetitive behaviors such as hand-wringing or tissue shredding.
Tend to wander and become lost.
Very severe cognitive decline (Severe or late-stage Alzheimer's disease)

This is the final stage of the disease when individuals lose the ability to respond to their environment, the ability to speak, and, ultimately, the ability to control movement.
Frequently individuals lose their capacity for recognizable speech, although words or phrases may occasionally be uttered.
Individuals need help with eating and toileting and there is general incontinence.
Individuals lose the ability to walk without assistance, then the ability to sit without support, the ability to smile, and the ability to hold their head up. Reflexes become abnormal and muscles grow rigid. Swallowing is impaired.

In various embodiments, administration of one or more agents described herein to subjects diagnosed with Alzheimer's disease is deemed effective when the there is a reduction in the CSF of levels of one or more components selected from the group consisting of Tau, phospho-Tau (pTau), APPneo, soluble Aβ40, soluble Aβ42, and/or and Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments, subjects amenable to the present methods generally are free of a neurological disease or disorder other than Alzheimer's disease. For example, in certain embodiments, the subject does not have and is not at risk of developing a neurological disease or disorder such as Huntington's Disease, and/or Parkinson's disease, and/or schizophrenia, and/or psychosis.

In various embodiments, the effectiveness of treatment can be determined by comparing a baseline measure of a parameter of disease before administration of the CRFR1 receptor antagonists and/or formulation(s) thereof is commenced to the same parameter one or more time points after the compound/formulation has been administered. One illustrative, but non-limiting, parameter that can be measured is a biomarker (e.g., a peptide oligomer) of APP processing. Such biomarkers include, but are not limited to increased levels of sAPPα, p3 (Aβ 17-42 or Aβ 17-40), βAPPβ, soluble Aβ40, and/or soluble Aβ42 in the blood, plasma, serum, urine, mucous or cerebrospinal fluid (CSF). Detection of increased levels of sAPPα and/or p3, and decreased levels of βAPPβ and/or APPneo is an indicator that the treatment is effective. Conversely, detection of decreased levels of sAPPα and/or p3, and/or increased levels of βAPPβ, APPneo, Tau or phospho-Tau (pTau) is an indicator that the treatment is not effective.

Another parameter to determine effectiveness of treatment is the level of amyloid plaque deposits in the brain. Amyloid plaques can be determined using any method known in the art, e.g., as determined by CT, PET, PIB-PET and/or MII.

In various embodiments, administration of the CRFR1 receptor antagonist(s) described herein can result in a reduction in the rate of plaque formation, and even a retraction or reduction of plaque deposits in the brain. Effectiveness of treatment can also be determined by observing a stabilization and/or improvement of cognitive abilities of the subject. Cognitive abilities can be evaluated using any art-accepted method, including for example, Clinical Dementia Rating (CDR), the mini-mental state examination (MMSE) or Folstein test, evaluative criteria listed in the DSM-IV (Diagnostic and Statistical Manual of Mental Disorders, Fourth Edition) or DSM-V, and the like.

In certain embodiments, the monitoring methods can entail determining a baseline value of a measurable biomarker or parameter (e.g., amyloid plaque load or cognitive abilities) in a subject before administering a dosage of the multi-component formulation and optionally one or more pharmaceuticals, and comparing this biomarker or parameter with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation/ANOVA) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (e.g., more than a standard deviation) is an indicator that treatment should be resumed in the subject.

In various embodiments, the tissue sample for analysis is typically blood, plasma, serum, urine, mucous or cerebrospinal fluid from the subject.

Pharmaceutical Formulations.

In certain embodiments, one or more allosteric CRFR1 receptor antagonists described herein or an enantiomer, a mixture of enantiomers, or a mixture of two or more diastereomers thereof, a pharmaceutically acceptable salt, ester, amide, solvate, hydrate, prodrug thereof or derivative thereof) are administered to a mammal in need thereof, e.g., to a mammal at risk for or suffering from a neurodegenerative pathology including, but not limited to a pathology characterized by abnormal processing of amyloid precursor proteins (e.g., amyloidogenic MCI, Alzheimer's disease, etc.), a mammal at risk for progression from a pre-symptomatic condition to a symptomatic condition (e.g., from an asymptomatic condition to MCI, from an asymptomatic condition to AD, from MCI to AD, and the like).

The CRFR1R antagonists described herein can be administered in the "native" form or, if desired, in the form of salts, esters, amides, prodrugs, derivatives, and the like, provided the salt, ester, amide, prodrug or derivative is suitable pharmacologically, e.g., effective in the present method(s). Salts, esters, amides, prodrugs and other derivatives of the CRFR1R antagonists can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, a pharmaceutically acceptable salt can be prepared for any compound described herein having a functionality capable of forming a salt (e.g., such as a carboxylic acid functionality of the compounds described herein). A pharmaceutically acceptable salt is any salt that retains the activity of the parent compound and does not impart any deleterious or untoward effect on the subject to which it is administered and in the context in which it is administered.

Methods of pharmaceutically formulating the compounds described herein as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the compounds described herein can include halide salts, such as may be prepared using hydrochloric or hydrobromic acids. Conversely, preparation of basic salts of the CRFR1 receptor antagonists described herein (e.g., see, e.g., FIG. 4) can be prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

In various embodiments, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the active agent (e.g., CRFR1 receptor antagonist). In certain embodiments, the esters are typically acyl-substituted derivatives of free alcohol groups, e.g., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the compounds identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., amyloidogenic pathologies).

The active agent(s) described herein (e.g., a CRFR1 receptor antagonist, and/or an enantiomer, a mixture of enantiomers, or a mixture of two or more diastereomers thereof; or a pharmaceutically acceptable salt, ester, amide, solvate, hydrate, or prodrug thereof or derivatives thereof) can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the CRFR1 receptor antagonist(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the CRFR1 receptor antagonists, or excipients or other stabilizers and/or buffers.

Other physiologically acceptable compounds, particularly of use in the preparation of tablets, capsules, gel caps, and the like include, but are not limited to binders, diluent/fillers, disintegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g., calcium carbonate, carboxymethylcellulose calcium, sodium starch glycollate, crospovidone etc.), a binder (e.g., alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., a compound(s) described herein or formulation thereof, and/or an enantiomer, a mixture of enantiomers, or a mixture of two or more diastereomers thereof, a pharmaceutically acceptable salt, ester, amide, solvate, hydrate, prodrug thereof or derivatives thereof) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethyl-cellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the CRFR1 antagonist(s) described herein and on the particular physio-chemical characteristics of the CRFR1 receptor antagonist(s).

In certain embodiments, the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectable, implantable sustained-release formulations, mucoadherent films, topical varnishes, lipid complexes, etc.

Pharmaceutical compositions comprising the CRFR1 receptor antagonists described herein (e.g., a CRFR1 receptor antagonist compound or formulation thereof, and/or an enantiomer, a mixture of enantiomers, or a mixture of two or more diastereomers thereof, a pharmaceutically acceptable salt, ester, amide, solvate, hydrate, prodrug thereof or derivatives thereof) described herein can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the CRFR1 receptor antagonist(s) into preparations that can be used pharmaceutically. Proper formulation is dependent upon the route of administration chosen.

For topical administration the CRFR1 receptor antagonist(s) described herein can be formulated as solutions, gels, ointments, creams, suspensions, and the like as are well-known in the art. Systemic formulations include, but are not limited to, those designed for administration by injection, e.g., subcutaneous, intravenous, intramuscular, intrathecal or intraperitoneal injection, as well as those designed for transdermal, transmucosal oral or pulmonary administration. For injection, the CRFR1 receptor antagonist(s) described herein can be formulated in aqueous solutions, preferably in physiologically compatible buffers such as Hanks solution, Ringer's solution, or physiological saline buffer and/or in certain emulsion formulations. The solution can contain formulatory agents such as suspending, stabilizing and/or dispersing agents. In certain embodiments, the CRFR1 receptor antagonist(s) can be provided in powder form for constitution with a suitable vehicle, e.g., sterile pyrogen-free water, before use. For transmucosal administration, penetrants appropriate to the barrier to be permeated can be used in the formulation. Such penetrants are generally known in the art.

For oral administration, the compounds can be readily formulated by combining the CRFR1 receptor antagonist(s) with pharmaceutically acceptable carriers well known in the art. Such carriers enable the compounds described herein to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

For administration by inhalation, the compound(s) described herein are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In various embodiments, the compound(s) described herein can be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations can be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that may be used to protect and deliver pharmaceutically active compounds. Certain organic solvents such as dimethylsulfoxide also can be employed, although usually at the cost of greater toxicity. Additionally, the compounds may be delivered using a sustained-release system, such as semipermeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

In certain embodiments, the compound(s) and/or formulations described herein are administered orally. This is readily accomplished by the use of tablets, caplets, lozenges, liquids, and the like.

In certain embodiments, the compound(s) and/or formulations described herein are administered systemically (e.g., orally, or as an injectable) in accordance with standard methods well known to those of skill in the art. In other embodiments, the agents can also be delivered through the skin using conventional transdermal drug delivery systems, e.g., transdermal "patches" wherein the compound(s) and/or formulations described herein are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the CRFR1 receptor antagonist(s) and any other materials that are present.

In certain embodiments, one or more compound(s) described herein can be provided as a "concentrate", e.g., in a storage container (e.g., in a premeasured volume) ready for dilution, or in a soluble capsule ready for addition to a volume of water, alcohol, hydrogen peroxide, or other diluent.

In certain embodiments, the compound(s) described herein are preferably suitable for oral administration. In various embodiments, the compound(s) in the oral compositions can be either coated or non-coated. The preparation of enteric-coated particles is disclosed for example in U.S. Pat. Nos. 4,786,505 and 4,853,230.

In various embodiments, compositions contemplated herein typically comprise one or more of the various CRFR1 receptor antagonists or formulations thereof, and/or an enantiomer, a mixture of enantiomers, or a mixture of two or more diastereomers thereof, a pharmaceutically acceptable salt, ester, amide, solvate, hydrate, prodrug thereof or derivatives thereof) described herein in an effective amount to achieve a pharmacological effect or therapeutic improvement without undue adverse side effects. Various effects deemed therapeutic are described above. Illustrative pharmacological effects or therapeutic improvements include, but are not limited to a reduction in the CSF of levels of one or more components selected from the group consisting of Tau, phospho-Tau (pTau), APPneo, soluble Aβ40 and soluble Aβ 42, and/or when a reduction of the plaque load in the brain of the subject, and/or a reduction in the rate of plaque formation in the brain of the subject, and/or an improvement in the cognitive abilities of the subject, and/or a perceived improvement in quality of life by the subject, and/or a significant reduction in clinical dementia rating (CDR) of the subject, and/or a slowing in the rate of increase in clinical dementia rating, and/or when a slowing or stopping in the progression of AD (e.g., when the transition from one stage to another as listed in Table 3 is slowed or stopped).

In various embodiments, the typical daily dose of compound(s) varies and will depend on various factors such as the individual requirements of the patients and the disease to be treated. In general, the daily dose of compounds can be in the range of 1-1,000 mg or 1-800 mg, or 1-600 mg, or 1-500 mg, or 1-400 mg. In one illustrative embodiment a standard approximate amount of the CRFR1 receptor antagonist(s) described above present in the composition can be typically about 1 to 1,000 mg, more preferably about 5 to 500 mg, and most preferably about 10 to 100 mg administered once a day, in certain embodiments, administered twice a day, in certain embodiments, administered 3 times/day, and in certain embodiments, administered 4, or 6, or 6 or 7, or 8 times/day.

The active ingredients of the are preferably formulated in a single oral dosage form containing all active ingredients. Such oral formulations include solid and liquid forms. It is noted that solid formulations typically provide improved stability as compared to liquid formulations and can often afford better patient compliance.

In one illustrative embodiment, the one or more of the various compound(s) described herein are formulated in a single solid dosage form such as single- or multi-layered tablets, suspension tablets, effervescent tablets, powder, pellets, granules or capsules comprising multiple beads as well as a capsule within a capsule or a double chambered capsule. In another embodiment, the compound(s) described herein may be formulated in a single liquid dosage form such as suspension containing all active ingredients or dry suspension to be reconstituted prior to use.

In certain embodiments, the compound(s) are formulated as enteric-coated delayed-release granules or as granules coated with non-enteric time-dependent release polymers in order to avoid contact with the gastric juice. Non-limiting examples of suitable pH-dependent enteric-coated polymers are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark EUDRAGIT L 100-55®. This coating can be spray coated onto a substrate.

Illustrative non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

Illustrative non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the EUDRAGIT® brand polymers. Other film-forming materials can be used alone or in combination with each other or with the ones listed above. These other film forming materials generally include, for example, poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials suitable for making the time-dependent release coating of the compounds described herein include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include, but are not limited to poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer.

While the compositions and methods are described herein with respect to use in humans, they are also suitable for animal, e.g., veterinary use. Thus certain illustrative organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Combined Treatment Methods and Combined Formulations

In certain instances, one or more of the CRFR1 receptor antagonist(s) described herein (or formulation, and/or an enantiomer, a mixture of enantiomers, or a mixture of two or more diastereomers thereof, a pharmaceutically acceptable salt, ester, amide, solvate, hydrate, prodrug thereof or derivative thereof) are administered in conjunction with one or more additional active agent(s) that are known, or believed, to have utility in the treatment of neurodegenerative diseases including, but not limited to Alzheimer's disease, age-related cognitive impairment, MCI, and the like. The two agents (e.g., a CRFR1 receptor antagonist described herein and additional agent) can be administered simultaneously or sequentially. When administered sequentially the two agents are typically administered so that both achieve a physiologically relevant concentration and/or effect over a similar time period (e.g., so that both agents are active at some common time).

In certain instances, one or more of the CRFR1 receptor antagonist(s) described herein (or formulation, and/or an enantiomer thereof, a mixture of enantiomers, or a mixture of two or more diastereomers thereof, and/or a pharmaceutically acceptable salt, ester, amide, solvate, hydrate, or prodrug thereof or derivative thereof) are administered before the one or more additional active agent(s) or they are administered after the one or more additional active agent(s). In certain embodiments one or more of the CRFR1 receptor antagonist(s) described herein (or formulation, and/or an enantiomer thereof, a mixture of enantiomers, or a mixture of two or more diastereomers thereof, and/or a pharmaceutically acceptable salt, ester, amide, solvate, hydrate, or prodrug thereof or derivative thereof) are administered simultaneously with one or more additional active agent(s) and in such instances may be formulated as a compound formulation.

Suitable additional active agent(s) include, but are not limited to, Donepezil (e.g., Aricept), Rivastigmine (e.g., EXELON®), Galantamine (e.g., RAZADINE®), Tacrine (e.g., COGNEX®), Memantine (e.g., NAMENDA®), Solanezumab, Bapineuzmab, Alzemed, Flurizan, ELND005, Valproate, Semagacestat, Rosiglitazone, Phenserine, Cernezumab, Dimebon, EGCg, Gammagard, PBT2, PF04360365, NIC5-15, Bryostatin-1, AL-108, Nicotinamide, EHT-0202, BMS708163, NP12, Lithium, ACC001, AN1792, ABT089, NGF, CAD106, AZD3480, SB742457, AD02, Huperzine-A, EVP6124, PRX03140, PUFA, HF02, MEM3454, TTP448, PF-04447943, Ent., GSK933776, MABT5102A, Talsaclidine, UB311, Begacestat, R1450, PF3084014, V950, E2609, MK0752, CTS21166, AZD-3839, LY2886721, CHF5074, anti-inflammatories (e.g., Flurizan (Myriad Genetics), Dapsone, anti-TNF antibodies (e.g., etanercept (Amgen/Pfizer)), and the like), statins (e.g., atorvastatin (LIPITOR®), simvastatin (ZOCOR®, etc.), BACE inhibitors and the like. In certain embodiments, treatment methods comprising administration of one or more CRFR1 receptor antagonist(s) described herein in conjunction with any one of the foregoing additional active agent(s) is contemplated.

In certain embodiments, treatment methods comprising administration of one or more CRFR1 receptor antagonist(s) described herein (or formulation, and/or an enantiomer thereof, a mixture of enantiomers, or a mixture of two or more diastereomers thereof, and/or a pharmaceutically acceptable salt, ester, amide, solvate, hydrate, or prodrug thereof or derivative thereof) in conjunction with additional therapeutic agents such as disulfiram and/or analogues thereof, honokiol and/or analogues thereof, tropisetron and/or analogues thereof, nimetazepam and/or analogues thereof (e.g., as described in U.S. Ser. No. 13/213,960 (U.S. Patent Publication No: US-2012-0071468-A1), and PCT/US2011/048472 (PCT Publication No: WO 2012/024616) which are incorporated herein by reference for the compounds described therein) are contemplated. In certain embodiments the treatment method comprises administration of tropisetron in conjunction with of one or more CRFR1 receptor antagonist(s) described herein.

In certain embodiments, combination formulations comprising one or more CRFR1 receptor antagonist(s) and the like described herein in combination with additional therapeutic agents such as disulfiram and/or analogues thereof, honokiol and/or analogues thereof, tropisetron and/or analogues thereof, nimetazepam and/or analogues thereof (e.g., as described in U.S. Ser. No. 13/213,960 (U.S. Patent Publication No: US-2012-0071468-A1), and PCT/US2011/048472 (PCT Publication No: WO 2012/024616) which are incorporated herein by reference for the compounds described therein) are contemplated. In certain embodiments the combination formulation comprises a CRFR1 receptor antagonist in combination with tropisetron and/or of one or more tropinol esters, related esters, derivatives thereof, analogs thereof, polymorphs thereof (e.g. as described in PCT/US2012/049223), and the like is contemplated.

Assay Systems to Evaluate APP Processing

Without being bound to a particular theory, it is believed that, in certain embodiments, the compounds and formulations described herein promote processing of APP by the non-amyloidogenic pathway and/or reduce or inhibit processing of APP by the amyloidogenic pathway. In the non-amyloidogenic pathway, APP is first cleaved by α-secretase within the Aβ sequence, releasing the sAPPα ectodomain ("sAPPα"). In contrast, the amyloidogenic pathway is initiated when β-secretase cleaves APP at the amino terminus of the Aβ, thereby releasing the APPsβ ectodomain ("sAPPβ"). APP processing by the non-amyloidogenic and amyloidogenic pathways is known in the art and reviewed, e.g., by Xu (2009) *J. Alzheimer's Dis.*, 16(2):211-224 and De Strooper et al., (2010) *Nat Rev Neurol.*, 6(2): 99-107.

One method to evaluate the efficacy of the compounds described herein is to determine whether or not the compound(s) in question produce a reduction or elimination in the level of APP processing by the amyloidogenic pathway, e.g., a reduction or elimination in the level of APP processing by β-secretase cleavage. Assays for determining the extent of APP cleavage at the β-secretase cleavage site are well known in the art. Illustrative assays, are described, for example, in U.S. Pat. Nos. 5,744,346 and 5,942,400. Kits for determining the presence and levels in a biological sample of sAPPα and sAPPβ, as well as APPneo and Aβ commercially available, e.g., from PerkinElmer.

Cell Free Assays

Illustrative assays that can be used to evaluate the biological activity of the compounds described herein can be found, for example, in PCT Publication Nos: WO 2000/017369, and WO 2000/003819, and in U.S. Pat. Nos. 5,942,400 and 5,744,346. In certain embodiments, such assays can be performed in cell-free incubations or in cellular incubations using cells expressing an alpha-secretase and/or beta-secretase and an APP substrate having an alpha-secretase and beta-secretase cleavage sites.

One illustrative assay tests the compound(s) of interest utilizing an APP substrate containing alpha-secretase and beta-secretase cleavage sites of APP, for example, a complete APP or variant, an APP fragment, or a recombinant or synthetic APP substrate containing the amino acid sequence: KM-DA or NL-DA, which is incubated in the presence of an α-secretase and/or β-secretase enzyme, a fragment thereof, or a synthetic or recombinant polypeptide variant having alpha-secretase or beta-secretase activity and effective to cleave the alpha-secretase or beta-secretase cleavage sites of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its α-secretase and/or β-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example, approximately 200 nanomolar to 10 micromolar substrate, approximately 10 to 200 picomolar enzyme, and approximately 0.1 nanomolar to 10 micromolar of the compound of interest (CRFR1 antagonist) in aqueous solution, at an approximate pH of 4-7, at approximately 37° C., for a time period of approximately 10 minutes to 3 hours. These incubation conditions are illustrative only, and can be varied as required for the particular assay components and/or desired measurement system. Optimization of the incubation conditions for the particular assay components can account for the specific alpha-secretase and/or beta-secretase enzyme used and its pH optimum, any additional enzymes and/or markers that might be used in the assay, and the like. Such optimization is routine and does not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of alpha-secretase and/or beta-secretase results in cleavage of the substrate at the alpha-secretase and/or beta-secretase cleavage sites, respectively. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assays

Numerous cell-based assays can be used to evaluate the effect of the compounds described herein on the ratio of relative alpha-secretase activity to beta-secretase activity and/or on the processing of APP to release amyloidogenic versus non-amyloidogenic Aβ oligomers. Contact of an APP substrate with an alpha-secretase and/or beta-secretase enzyme within the cell and in the presence or absence of compound(s) in question can be used to demonstrate α-secretase and/or β-secretase inhibitory activity of the compound(s). Preferably, the assay in the presence of compound(s) provides at least about 30%, most preferably at least about 50% inhibition of the enzymatic activity, as compared with a non-inhibited control.

In one illustrative embodiment, cells that naturally express alpha-secretase and/or beta-secretase are used. Alternatively, cells can be modified to express a recombinant α-secretase and/or β-secretase or synthetic variant enzymes, as discussed above. In certain embodiments, the APP substrate can be added to the culture medium and in certain embodiments, the substrate is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the α-secretase and/or β-secretase APP cleavage sites can be used, provided that the expressed APP is permitted to contact the enzyme and enzymatic cleavage activity can be analyzed.

Human cell lines that normally process Aβ from APP provide a useful means to assay inhibitory activities of the compound(s) described herein. Production and release of Aβ and/or other cleavage products into the culture medium can be measured, for example by immunoassay, such as Western blot or enzyme-linked immunoassay (EIA) such as by ELISA.

In certain embodiments, cells expressing an APP substrate and an active α-secretase and/or β-secretase can be incubated in the presence of the compound(s) being tested to demonstrate the effect of the compound(s) on relative enzymatic activity of the α-secretase and/or β-secretase as compared with a control. Relative activity of the alpha-secretase to the beta-secretase can be measured by analysis of one or more cleavage products of the APP substrate. For example, inhibition of β-secretase activity against the substrate APP would be expected to decrease release of specific β-secretase induced APP cleavage products such as Aβ, sAPPβ and APPneo. Promotion or enhancement of α-secretase activity against the substrate APP would be expected to increase release of specific α-secretase induced APP cleavage products such as sAPPα and p3 peptide.

Although both neural and non-neural cells process and release Aβ, levels of endogenous beta-secretase activity are low and often difficult to detect by EIA. The use of cell types known to have enhanced beta-secretase activity, enhanced processing of APP to Aβ, and/or enhanced production of Aβ are therefore preferred. For example, transfection of cells with the Swedish Mutant form of APP (APP-SW); with APP-KK (APP containing an ER retention signal (-KKQN-, (SEQ ID NO:1)) appended to the C terminus of APP), or with APP-SW-KK provides cells having enhanced beta-secretase activity and producing amounts of Aβ that can be readily measured.

In such assays, for example, the cells expressing APP, alpha-secretase and/or beta-secretase are incubated in a culture medium under conditions suitable for α-secretase and/or β-secretase enzymatic activity at its cleavage site on the APP substrate. On exposure of the cells to the compound of interest (e.g., CRFR1 receptor antagonist) the amount of Aβ released into the medium and/or the amount of CTF99 fragments of APP in the cell lysates is reduced as compared with the control. The cleavage products of APP can be analyzed, for example, by immune reactions with specific antibodies, as discussed above.

In certain embodiments, preferred cells for analysis of α-secretase and/or β-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze the effect of a compound described herein on the relative alpha-secretase and/or beta-secretase activity and/or processing of APP to release Aβ. For example, transgenic animals expressing APP substrate, alpha-secretase and/or beta-secretase enzyme can be used to demonstrate activity of the compound. Certain transgenic animal models have been described, for example, in U.S. Pat. Nos. 5,877,399; 5,612,486; 5,387,742; 5,720,936; 5,850,003; 5,877,015, and 5,811,633, and in Games et al., (1995) Nature 373: 523-527. Preferred are animals that exhibit characteristics associated with the pathophysiology of AD. Administration of the compound to the transgenic mice described herein provides an alternative method for demonstrating the inhibitory activity of the compound(s) in question. In certain embodiments, administration of the compound in a pharmaceutically effective carrier and via an administrative route that reaches the target tissue in an appropriate therapeutic amount is preferred.

Inhibition of beta-secretase mediated cleavage of APP at the beta-secretase cleavage site and of Aβ release can be analyzed in these animals by measure of cleavage fragments in the animal's body fluids such as cerebral fluid or tissues. Likewise, promotion or enhancement of alpha-secretase mediated cleavage of APP at the alpha-secretase cleavage site and of release of sAPPα can be analyzed in these animals by measure of cleavage fragments in the animal's body fluids such as cerebral fluid or tissues. In certain embodiments, analysis of brain tissues for Aβ deposits or plaques is preferred.

In certain illustrative assays, an APP substrate is contacted with an alpha-secretase and/or beta-secretase enzyme in the presence of the compound of interest under conditions sufficient to permit enzymatic mediated cleavage of APP and/or release of Aβ from the substrate. The compound is deemed effective when it reduces beta-secretase-mediated cleavage of APP at the β-secretase cleavage site and/or reduces released amounts of Aβ. In certain embodiments the related compounds are also deemed effective if they enhance α-secretase-mediated cleavage of APP at the α-secretase cleavage site and to increase released amounts of sAPPα and/or to reduce Aβ deposition in brain tissues of the animal, and to reduce the number and/or size of beta amyloid plaques.

Methods of Monitoring Clinical Efficacy

In certain embodiments, clinical efficacy can be monitored using any method known in the art. Measurable biomarkers to monitor efficacy include, but are not limited to, monitoring blood, plasma, serum, mucous or cerebrospinal fluid (CSF) levels of sAPPα, sAPPβ, Aβ42, Aβ40, APPneo and p3 (e.g., Aβ17-42 or Aβ17-40). Detection of increased levels of sAPPα and/or p3 and decreased levels of sAPPβ and APPneo are indicators that the treatment or prevention regime is efficacious. Conversely, detection of decreased levels of sAPPα and/or p3, Aβ42 and increased levels of sAPPβ and APPneo are indicators that the treatment or prevention regime is not efficacious. Other biomarkers include Tau and phospho-Tau (pTau). Detection of decreased levels of Tau and pTau are indicators that the treatment or prevention regime is efficacious.

Efficacy can also be determined by measuring amyloid plaque load in the brain. The treatment or prevention regime is considered efficacious when the amyloid plaque load in the brain does not increase or is reduced. Conversely, the treatment or prevention regime is considered inefficacious when the amyloid plaque load in the brain increases. Amyloid plaque load can be determined using any method known in the art, e.g., including magnetic resonance imaging (MRI).

Efficacy can also be determined by measuring the cognitive abilities of the subject. Cognitive abilities can be measured using any method known in the art. One test is the clinical dementia rating (CDR) described above, while another is the mini mental state examination (MMSE) (Folstein, et al., *J. Psychiatric Res.* 12 (3): 189-198). In certain embodiments, subjects who maintain the same score or who achieve a higher score on a CDR and/or on an MMSE indicate that the treatment or prevention regime is efficacious. Conversely, subjects who score lower on a CDR and/or on an MMSE indicate that the treatment or prevention regime has not been efficacious.

In certain embodiments, the monitoring methods can entail determining a baseline value of a measurable biomarker or parameter (e.g., amyloid plaque load or cognitive ability) in a subject before administering a dosage of the compound of interest (e.g., a CRFR1 receptor antagonist described herein) and comparing this with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment, but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and a decision not to resume treatment can be considered/evaluated. In all of these cases, a significant difference relative to the control level (e.g., more than a standard deviation) is an indicator that resumption of the subject should be considered.

In certain embodiments, the tissue sample for analysis is typically blood, plasma, serum, mucous or cerebrospinal fluid from the subject.

Kits.

In various embodiments the active agents described herein (e.g., allosteric CRFR1 receptor antagonists or analogs and/or derivatives, or tautomer(s) thereof, or stereoisomer(s) thereof, or pharmaceutically acceptable salts, solvates, or clathrates of said antagonists or prodrugs thereof) can be provided in kits. In certain embodiments the kits comprise the active agent(s) described herein enclosed in multiple or single dose containers. In certain embodiments the kits can comprises component parts that can be assembled for use. For example, an active agent in lyophilized form and a suitable diluent may be provided as separated components for combination prior to use. A kit may include an active agent and a second therapeutic agent for co-administration. The active agent and second therapeutic agent may be provided as separate component parts. A kit may include a plurality of containers, each container holding one or more unit dose of the compounds. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration, e.g., as described herein.

In certain embodiments the kits can further comprise instructional/informational materials. In certain embodiments the informational material(s) indicate that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. In certain embodiments the informational material(s) may indicate that anaphylaxis can be fatal and may occur when any foreign substance is introduced into the body. In certain embodiments the informational material may indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

While the instructional materials typically comprise written or printed materials they are not limited to such. Any medium capable of storing such instructions and communicating them to an end user is contemplated herein. Such media include, but are not limited to electronic storage media (e.g., magnetic discs, tapes, cartridges, chips), optical media (e.g., CD ROM), and the like. Such media may include addresses to internet sites that provide such instructional materials.

In some embodiments, the kits can comprise one or more packaging materials such as, for example, a box, bottle, tube, vial, container, sprayer, insufflator, intravenous (I.V.) bag, envelope, and the like, and at least one unit dosage form of an agent comprising active agent(s) described herein and a packaging material. In some embodiments, the kits also include instructions for using the composition as prophylactic, therapeutic, or ameliorative treatment for the disease of concern.

In some embodiments, the articles of manufacture can comprise one or more packaging materials such as, for example, a box, bottle, tube, vial, container, sprayer, insufflator, intravenous (I.V.) bag, envelope, and the like; and a first composition comprising at least one unit dosage form of an agent comprising one or more CRFR1 receptor antagonists described herein within the packaging material.

EXAMPLES

The following examples are offered to illustrate, but not to limit the claimed invention.

Example 1

Preparation of 6-(4-methoxy-2-methylphenoxy)-N-(1-methoxybutan-2-yl)-2,5-dimethylpyrimidin-4-amine (T36) and 6-(4-chloro-2-methylphenoxy)-N-(1-methoxybutan-2-yl)-2,5-dimethylpyrimidin-4-amine (T37)

Figure 3:
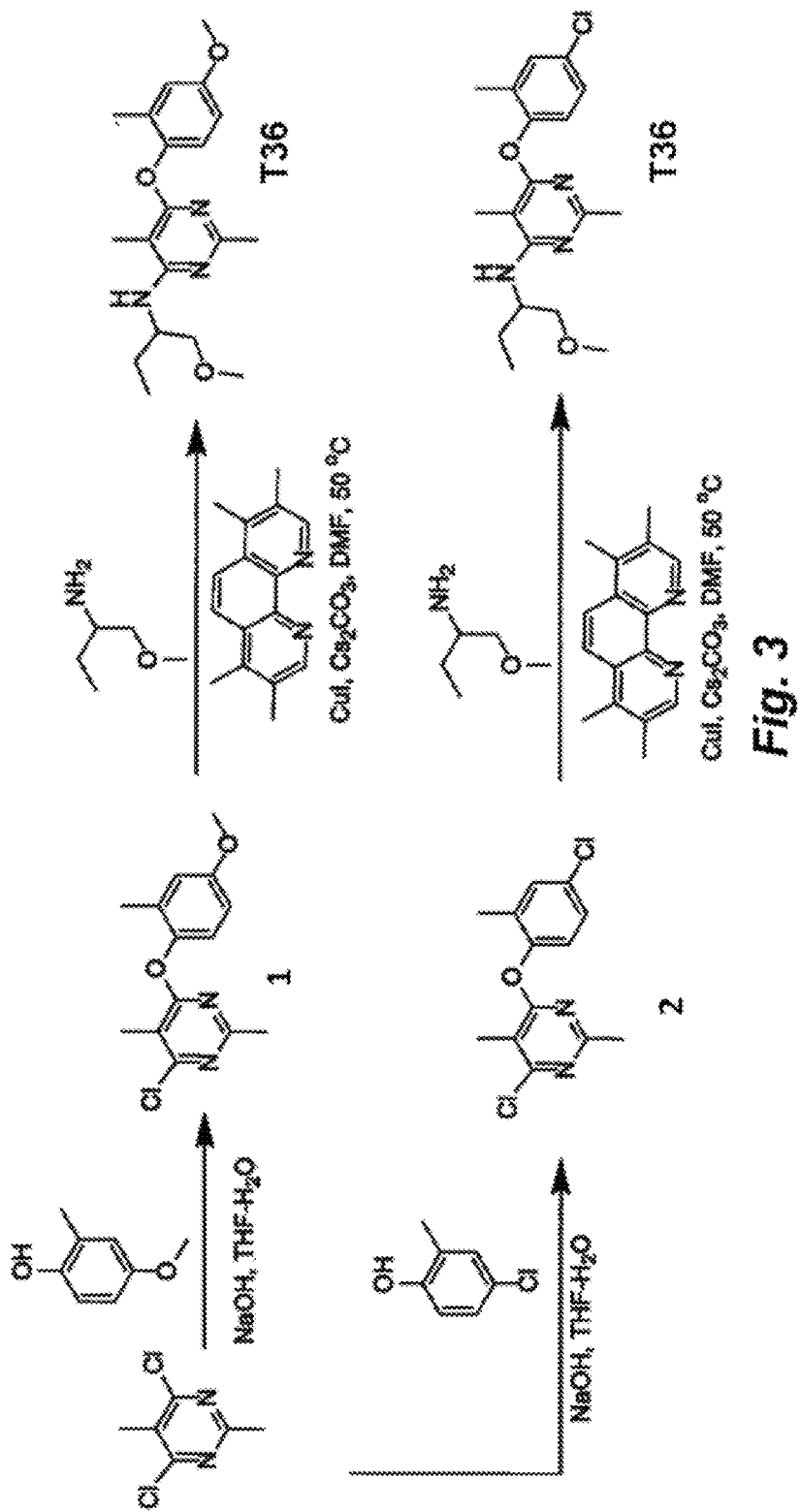
FIG. 3 illustrative synthesis schemes for T36 and T37.

Synthesis schemes for T36 and T37 are shown in FIG. 3.

4-Chloro-6-(4-methoxy-2-methylphenoxy)-2,5-dimethylpyrimidine (1)

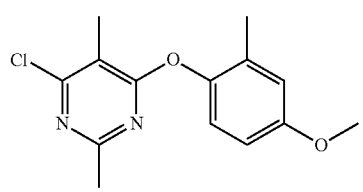 [SMILES: COc1ccc(Oc2nc(C)nc(Cl)c2C)c(C)c1]

Figure 4:
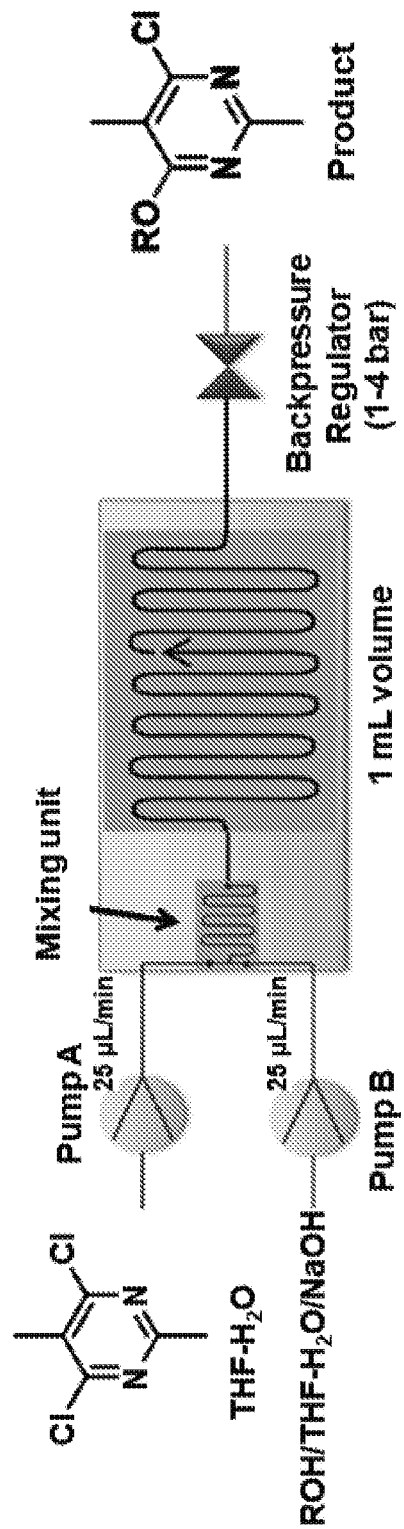
FIG. 4 illustrative schematic for a microfluidic reactor setup.

Two solutions, one with the aryl halide (0.56 mmol, 1.0 equivalent) in THF-H$_2$O (2.5 mL, 3:2 v/v) and one with phenol (0.84 mmol, 1.5 equivalent) and NaOH (0.84 mmol, 1.5 equivalent) in THF-H$_2$O (2.5 mL, 3:2 v/v) were prepared and then introduced into Asia microfluidic reactor by Pump A & B (see, e.g., FIG. 4). The mixture was pumped through a preheated 1 mL glass microfluidic reactor at a predetermined flow rate to achieve the desired residence time. The crude product was collected in a flask and extracted with ethyl acetate. The organic phase was combined, dried MgSO$_4$ and concentrated under reduced pressure. The isolated crude product was purified using a prepacked silica cartridge on a Teledyne CombiFlash R$_f$ 200 instrument. Fractions corresponding to the product peak were combined and concentrated using rotavap to afford 1 as white solid (135 mg, 87%). $^1$H NMR (CDCl$_3$) δ2.08 (s, 3H), 2.36 (s, 3H), 2.41 (s, 3H), 3.79 (s, 3H), 6.72-6.79 (m, 2H) and 6.94 (d, J=8.4 Hz, 1H); $^{13}$C NMR (CDCl$_3$) δ11.6, 16.7, 25.5, 55.6, 111.9, 113.0, 116.2, 122.6, 131.3, 144.9, 157.1, 160.1, 165.2 and 168.1; mass spectrum (APCI), m/z calcd for C$_{14}$H$_{16}$ClN$_2$O$_2$ (M+H)$^+$ 279.0895, found 279.0888.

4-Chloro-6-(4-chloro-2-methylphenoxy)-2,5-dimethylpyrimidine (2)

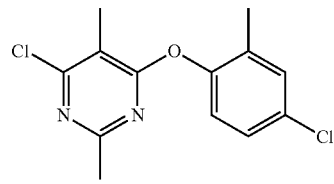 [SMILES: Cc1nc(Cl)c(C)c(Oc2ccc(Cl)cc2C)n1]

Two solutions, one with the aryl halide (0.56 mmol, 1.0 equivalent) in THF-H$_2$O (2.5 mL, 3:2 v/v) and one with phenol (0.84 mmol, 1.5 equivalent) and NaOH (0.84 mmol, 1.5 equivalent) in THF-H$_2$O (2.5 mL, 3:2 v/v) were prepared and then introduced into Asia microfluidic reactor by Pump A & B (see, e.g., FIG. 4). The mixture was pumped through a preheated 1 mL glass microfluidic reactor at a predetermined flow rate to achieve the desired residence time. The crude product was collected in a flask and extracted with ethyl acetate. The organic phase was combined, dried MgSO$_4$ and concentrated under reduced pressure. The isolated crude product was purified using a prepacked silica cartridge on a Teledyne CombiFlash R$_f$ 200 instrument. Fractions corresponding to the product peak were combined and concentrated using rotavap to afford 2 as white powder (131 mg, 83%). $^1$H NMR (CDCl$_3$) δ2.09 (s, 3H), 2.36 (s, 3H), 2.41 (s, 3H), 6.97 (d, J=8.8 Hz, 1H) and 7.15-7.23 (m, 2H); $^{13}$C NMR (CDCl$_3$) δ11.6, 16.4, 25.4, 113.2, 123.4, 127.0, 130.8, 131.1, 132.3, 149.9, 160.5, 165.3 and 167.5; mass spectrum (APCI), m/z calcd for C$_{13}$H$_{13}$Cl$_2$N$_2$O (M+H)$^+$ 283.0399, found 283.0396.

6-(4-methoxy-2-methylphenoxy)-N-(1-methoxybutan-2-yl)-2,5-dimethylpyrimidin-4-amine (T36)

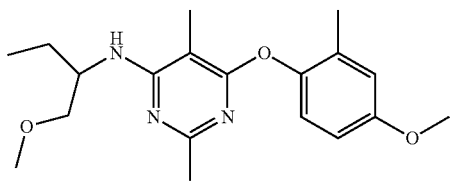 [SMILES: CCC(COC)Nc1nc(C)nc(Oc2ccc(OC)cc2C)c1C]

50 mL round bottom flask was charged with 1, CuI, Me$_4$-phenanthroline, Cs$_2$CO$_3$, and 4-methoxy-2-methylaniline in dry DMF under nitrogen. Reaction mixture was stirred for 16 h at 50° C. and then cooled to room temperature. Mixture was filtered through a short silica plug and washed with EtOAC. Crude obtained was washed with NaHCO$_3$ and extracted with EtOAC (2×10 mL). Combined organic phase was dried (MgSO$_4$), followed by purification using silica gel chromatography on Combiflash $R_f$ 200 by employing hexane-EtOAC step gradient (95:5→80:20) over 30 min. Fractions corresponding to the product peak were combined and concentrated using rotavap.

6-(4-chloro-2-methylphenoxy)-N-(1-methoxybutan-2-yl)-2,5-dimethylpyrimidin-4-amine (T37)

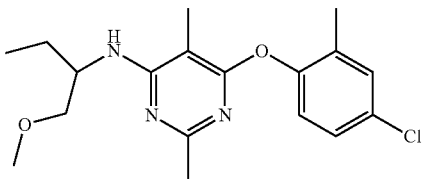 [SMILES: CCC(COC)Nc1nc(C)nc(Oc2ccc(Cl)cc2C)c1C]

50 mL round bottom flask was charged with 2, Cu', Me₄-phenanthroline, Cs₂CO₃, and 4-methoxy-2-methylaniline in dry DMF under nitrogen. Reaction mixture was stirred for 16 h at 50° C. and then cooled to room temperature. Mixture was filtered through a short silica plug and washed with EtOAC. Crude obtained was washed with NaHCO₃ and extracted with EtOAC (2×10 mL). Combined organic phase was dried (MgSO₄), followed by purification using silica gel chromatography on Combiflash $R_f$ 200 by employing hexane-EtOAC step gradient (95:5→80:20) over 30 min. Fractions corresponding to the product peak were combined and concentrated using rotavap.

Example 2

Preparation of N-(4-methoxy-2-methylphenyl)-641-methoxybutan-2-yl)oxy)-2,5-dimethylpyrimidin-4-amine (T38)

Figure 5:
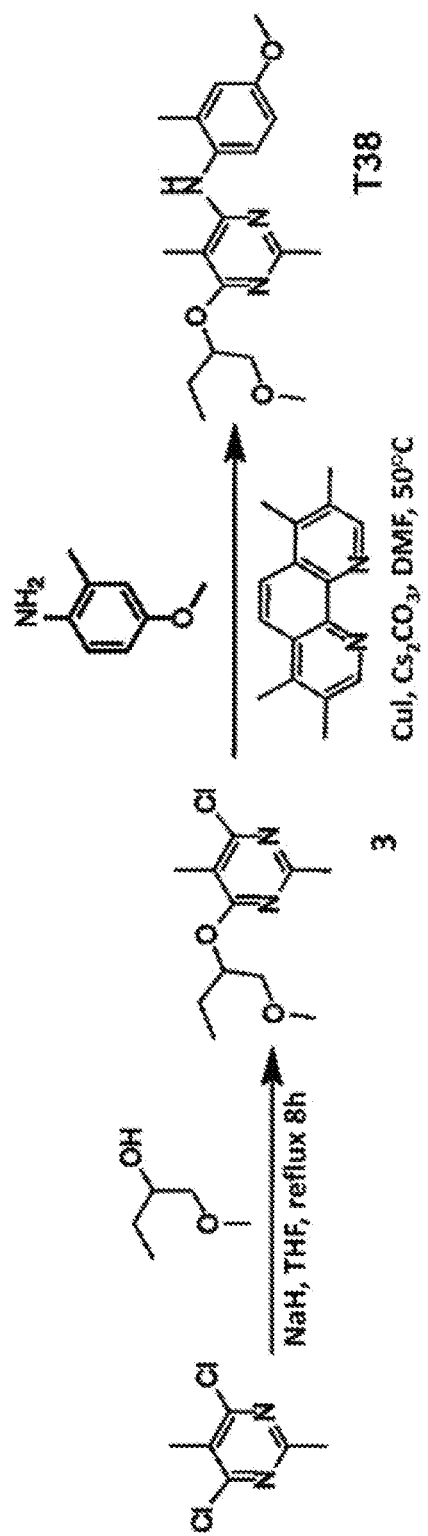
FIG. 5 illustrative scheme for the synthesis of T38.

A synthesis scheme for T38 is shown in FIG. 5.

4-chloro-6-((1-methoxybutan-2-yl)oxy)-2,5-dimethylpyrimidine (3)

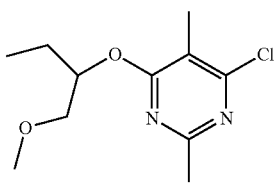 [SMILES: CCC(COC)Oc1nc(C)nc(Cl)c1C]

To a dried flask was added 500 mg of 2,4-dichloro-3,5-dimethylpyrimidine, NaH and suspended in dry THF. 1-Methoxy-2-butanol was added to mixture dropwise and mixture was left for stirring at reflux for 6 h. Crude obtained was washed with NaHCO₃ and extracted with EtOAC (2×10 mL). Combined organic phase was dried (MgSO₄), followed by purification using silica gel chromatography on Combiflash $R_f$ 200 by employing hexane-EtOAC step gradient (100:0→90:10) over 30 min. Fractions corresponding to the product peak were combined and concentrated using rotavap.

N-(4-methoxy-2-methylphenyl)-6-((1-methoxybutan-2-yl)oxy)-2,5-dimethylpyrimidin-4-amine (T38)

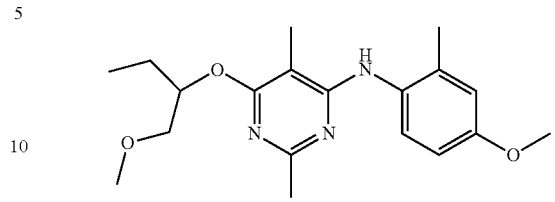

60 mL round bottom flask was charged with 2, CuI Me₄-phenanthroline, Cs₂CO₃, and 4-methoxy-2-methylaniline in dry DMF under nitrogen. Reaction mixture was stirred for 16 h at 50° C. and then cooled to room temperature. Mixture was filtered through a short silica plug and washed with EtOAC. Crude obtained was washed with NaHCO₃ and extracted with EtOAC (2×10 mL). Combined organic phase was dried (MgSO₄), followed by purification using silica gel chromatography on Combiflash $R_f$ 200 by employing hexane-EtOAC step gradient (95:5→80:20) over 30 min. Fractions corresponding to the product peak were combined and concentrated using rotavap.

Example 3

Preparation of Compounds T39, T41, T45, T46, T47, and T48

Figure 6A:
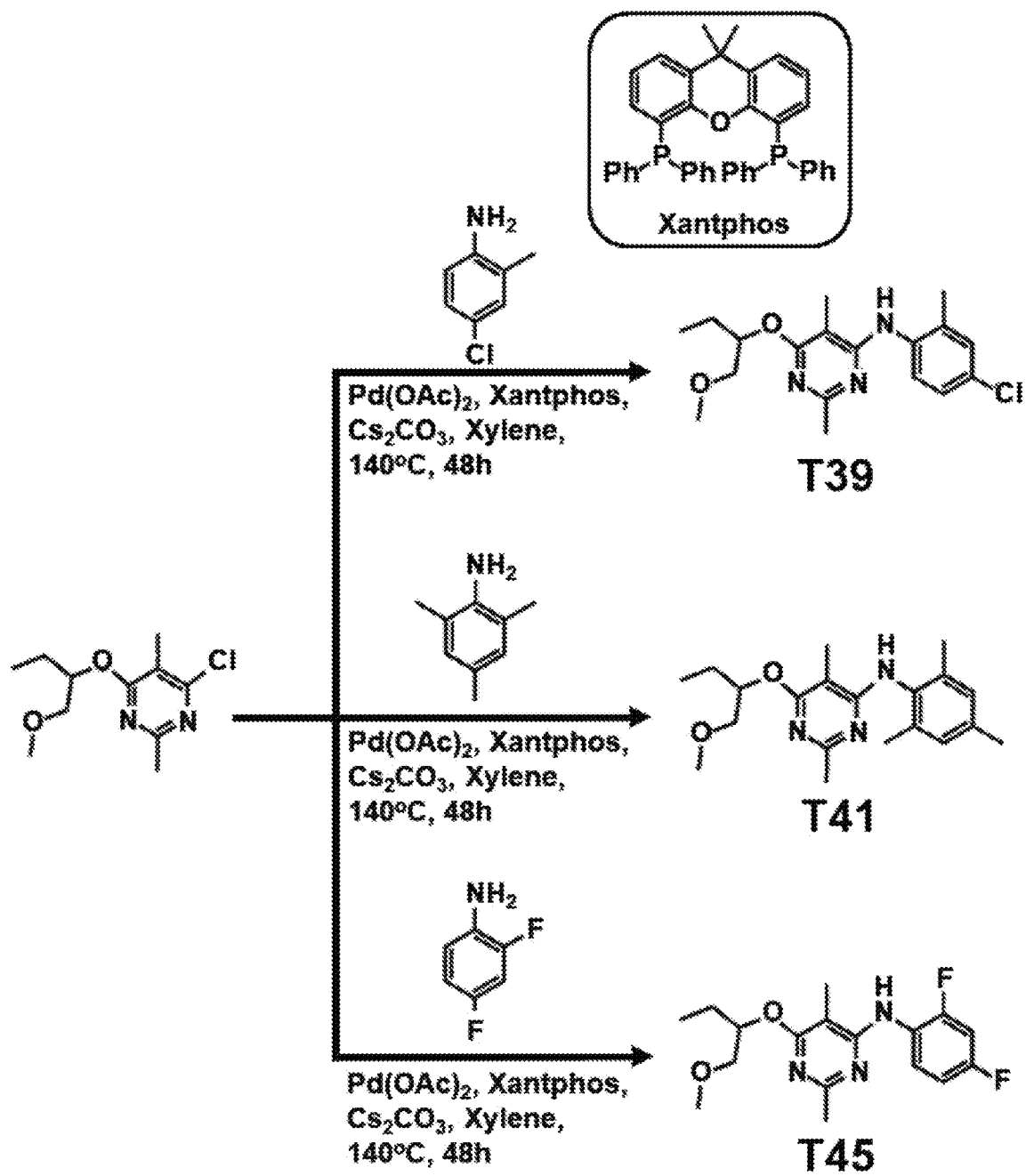
FIGS. 6A and 6B illustrative schemes for the synthesis of T39, T41, and T45 (FIG. 6A), and T46, T47, and T48 (FIG. 6B).
Figure 6B:
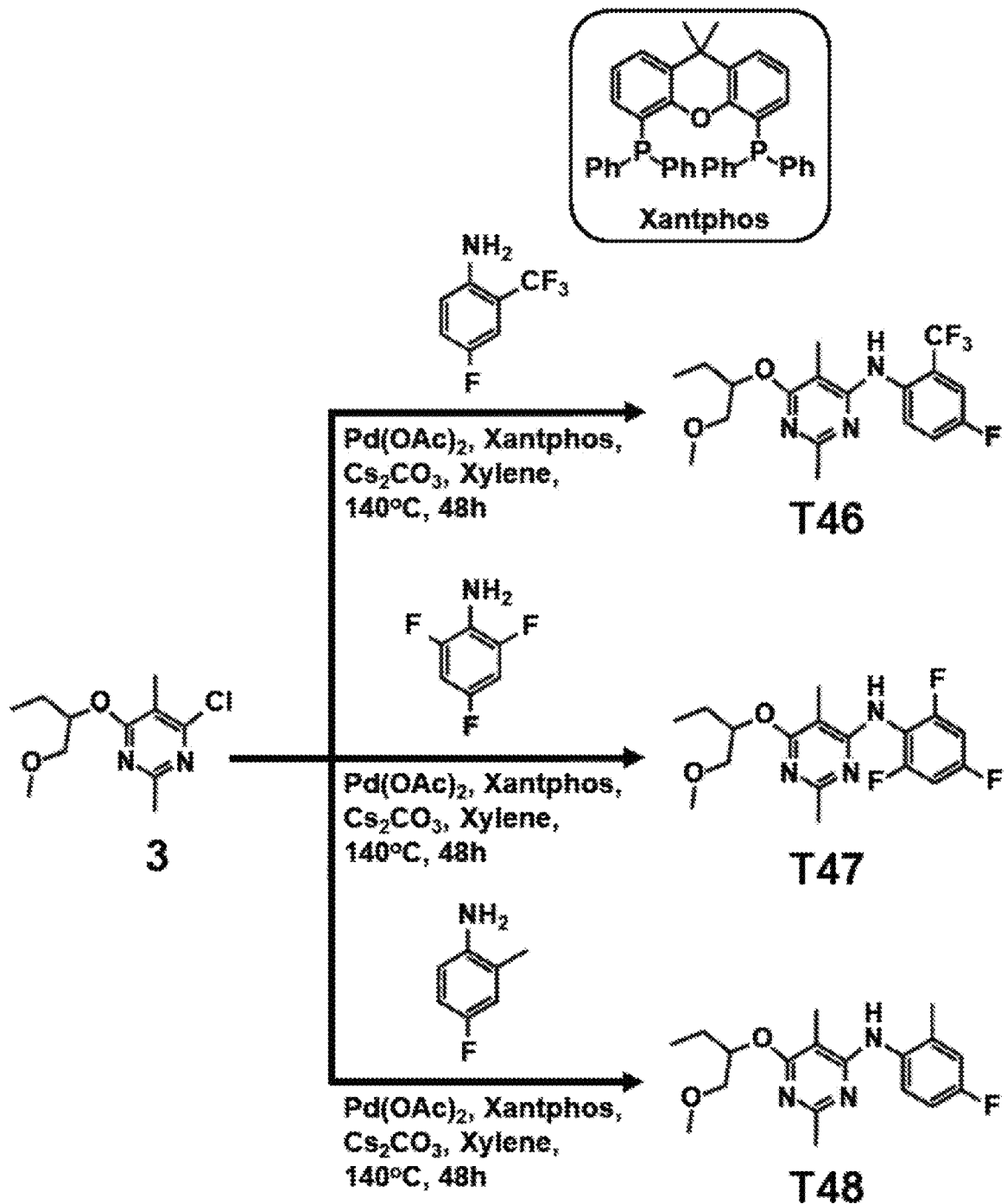

Reaction schemes for the preparation of T39, T41, T45, T46, T47, and T48 are shown in FIG. 6.

General Procedure:

15 mL glass pressure tube was charged with 3, Cs₂CO₃, xantphos, Pd(OAC)₂, and corresponding amines in xylene under nitrogen. Reaction mixture was stirred for 48 h at 140° C. and then cooled to room temperature. Mixture was filtered through a short silica plug and washed with EtOAC. Crude obtained was washed with NaHCO₃ and extracted with EtOAC (2×10 mL). Combined organic phase was dried (MgSO₄), followed by purification using silica gel chromatography on Combiflash $R_f$ 200 by employing hexane-EtOAC step gradient (95:5→80:20) over 30 min. Fractions corresponding to the product peak were combined and concentrated using rotavap to afford the desired compound.

Radioligand-Receptor Binding Assays (Agonist Radioligand).

Isolation of membranes from permanently transfected HEK293 cells expressing tCRFR1 or hCRFR1 and Scatchard analysis were performed with 50-100 ng protein as described (3) except that 50 pM [$^{125}$I]Tyr-sauvagine (NEN) was used as radioligand. [$^{125}$I]Tyr-Sauvagine was chosen as radioligand because of its equal high affinity for both CRF-R1 and CRF-R2. Nonspecific binding was always defined as residual [$^{125}$I]Tyr-sauvagine binding in the presence of 1 μM unlabeled ligand. The dissociation constant, $K_D$, was calculated by the Ligand program (Munson et al. (1980) *Anal. Biochem.* 107: 220).

Radioligand Receptor Binding Assay of Cloned Receptor (Antagonist Effect).

COS-M6 cells were transfected with 10-20 ng of plasmid DNA, and after two days cells were washed with HDB and detached by incubation with 0.5 mM EDTA in HDB for 15 min at 21° C. The cells were washed twice with HDB and homogenized in 5% sucrose. The homogenate was centrifuged at 600×g for 5 min, after which the supernatant was centrifuged at 40,000×g for 20 min. The resulting membrane homogenate, P2, was resuspended at 1-4 mg/ml in 10% sucrose and used in the binding assay (Perrin et al. (1986) *Endrocrinology*, 118: 11715). Dissociation constants were calculated from relative potencies by using the ALLFIT program (DeLean et al. (1978) *Am. J. Physiol.* 235: E97) and determined from competitive displacement assays with rat/human CRF (r/hCRF) as the standard.

Receptor Binding, Inhibition, and Parallel Artificial Membrane Permeability Assay (PAMPA).

Agilent 1260 infinity high-performance liquid chromatography system was used for analysis. The analytical column used was an IAM.PC.DD.2 column (4.6 mm i.d.×10 cm length, particle size 10 pm, pore size 300 Å) purchased from Regis Technologies (Morton Grove, Ill.). The mobile phase was a mixture of acetonitrile and water (35:65 v/v). The flow rate of the mobile phase was maintained at 1.0 ml/min at 25° C., and the ultraviolet absorption wavelength was set at 254 nm. Analysis was performed using 5 μL injection of the 2 mM stock solutions of the compounds. Compounds with $k_{IAM}$ values >1 in the PAMPA assay in our hands are indicative of good brain permeability.

Initial results of the receptor binding study are shown in Table 4. Structures of the various tested compounds are shown in Table 5.

TABLE 4

Illustrative compounds evaluated in the primary receptor binding screening and PAMPA.

| Compound | MW (Da) | CRF1 (agonist radio-ligand) $K_d$/(nM) | $EC_{50}$ (CRF1 antagonist effect) | cLogP | PAMPA $K_{IAM}$ | p-tau (% control) |
|---|---|---|---|---|---|---|
| T33 | 343.47 | ~30 | >2 μM | 4.61 | 6.34 | ND |
| T36 | 345.44 | >100 | | 3.84 | 2.31 | ND |
| T37 | 349.86 | >100 | | 4.46 | 5.79 | |
| T38 | 345.44 | ~30 | >2 μM | 4.27 | 2.02 | |
| T39 | 349.86 | 75 | >10 μM | 4.89 | 6.19 | |
| T40 | 312.41 | >100 | | 2.75 | 4.68 | |
| T41 | 343.47 | 15 | 400 nM | 5.04 | 4.01 | |
| T45 | 337.37 | >100 | | 4.10 | 3.32 | |
| T46 | 387.38 | >100 | | 4.83 | 2.90 | |
| T47 | 355.36 | >>100 | | 4.19 | 2.00 | |
| T48 | 333.41 | 100 | | 4.38 | 3.27 | |
| T49 | 347.43 | 40 | | 4.76 | | |
| T50 | 329.44 | 100 | | 4.64 | | |
| T51 | 330.43 | 1000 | | 3.77 | | |
| T53 | 319.41 | DEAD | | 2.44 | | |
| T54 | 305.38 | DEAD | | 2.41 | | |
| J03 | 355.43 | 7 | 1000 nM | 4.10 | 1.03 | 30 |
| J32 | 368.49 | 50 | 400 nM | | | 30 |

Of the compounds tested. T41 had the best CRFR1 binding (see Table 4, above) with a Kd~15 nM (done at CEREP). T41 gave 70% inhibition of CRFR1 CAMP signaling ("CRF1 antagonist effect") at 1 μM upon CRF binding, with a $K_I$ of 400 nM. T41 was also tested in the Parallel Artificial Membrane Permeability Assay (PAMPA) for its potential to be brain penetrant (cross the blood-brain barrier, BBB), and this compound gave a relatively good KW of ~4.

TABLE 5

Compounds tested in receptor binding study.

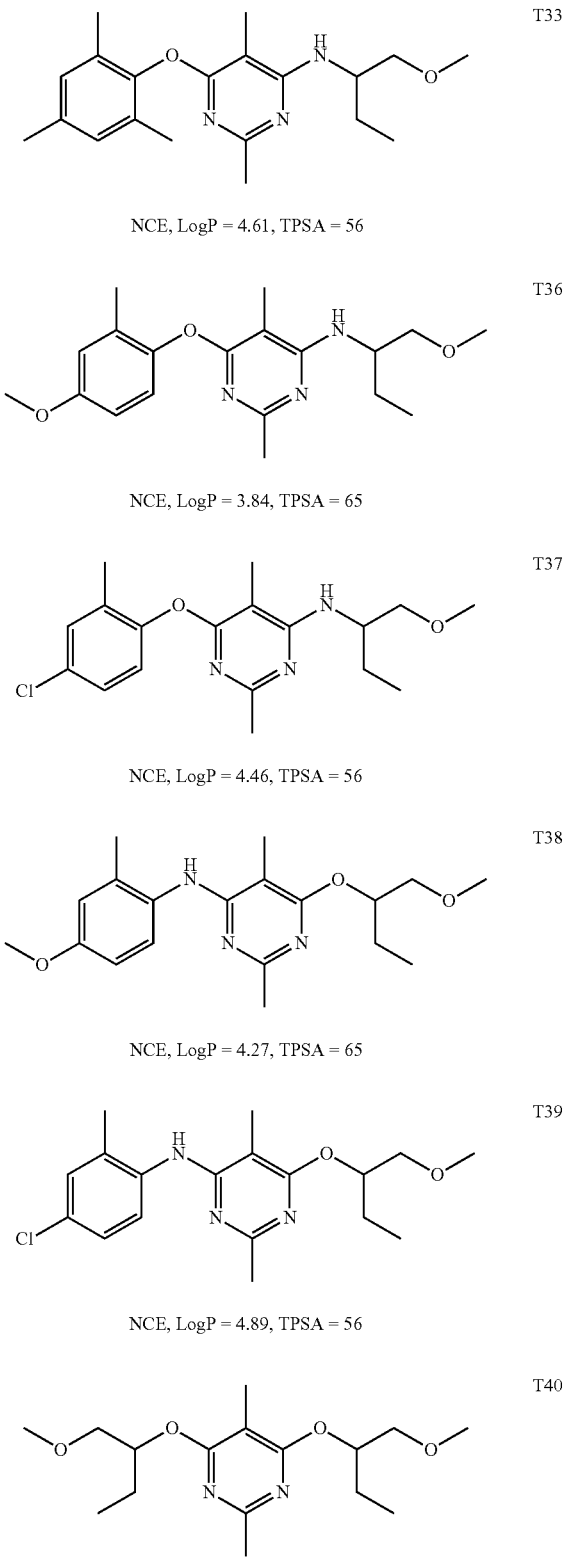

TABLE 5-continued
Compounds tested in receptor binding study.
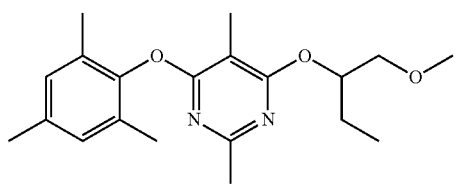
T41
NCE, LogP = 5.04, TPSA = 56
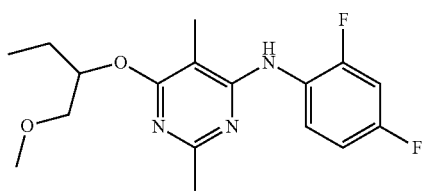
T45
NCE, LogP = 4.1, TPSA = 56
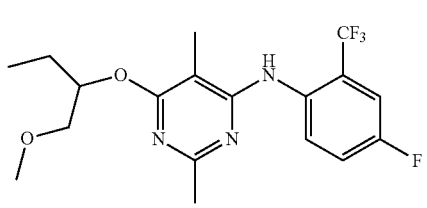
T46
NCE, LogP = 4.83, TPSA = 56
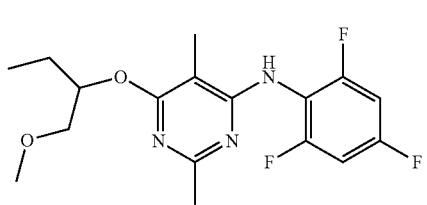
T47
NCE, LogP = 4.19, TPSA = 56
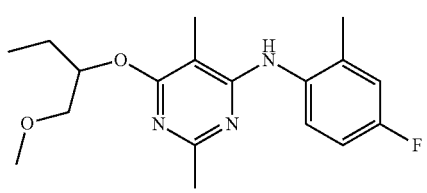
T48
NCE, LogP = 4.38, TPSA = 56
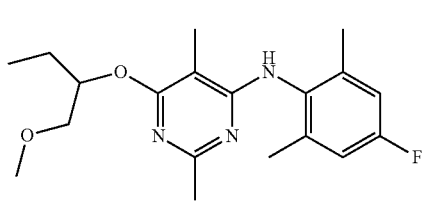
T49
NCE, LogP = 4.76, TPSA = 56
TABLE 5-continued
Compounds tested in receptor binding study.
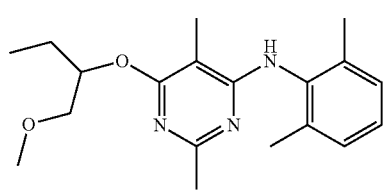
T50
NCE, LogP = 4.64, TPSA = 56
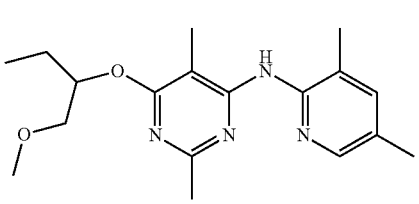
T51
NCE, LogP = 3.77, TPSA = 69
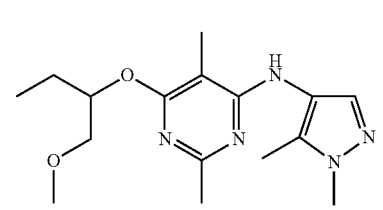
T53
NCE, LogP = 2.44, TPSA = 74
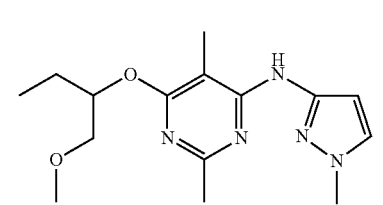
T54
NCE, LogP = 2.41, TPSA = 74
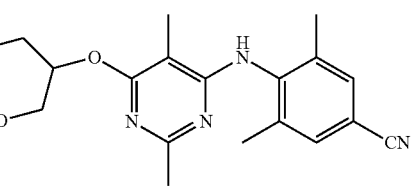
T55
NCE, LogP = 4.35, TPSA = 80
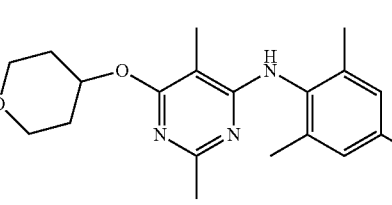
T61
NCE, LogP = 4.57, TPSA = 56

TABLE 5-continued

Compounds tested in receptor binding study.

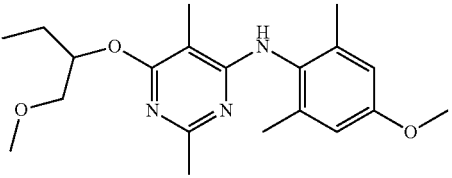

T56

NCE, LogP = 4.65, TPSA = 65

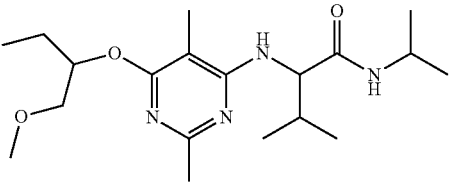

T58

NCE, LogP = 2.59, TPSA = 85 p-Tau & Tau Effects after Compound Treatment

Figure 7A:
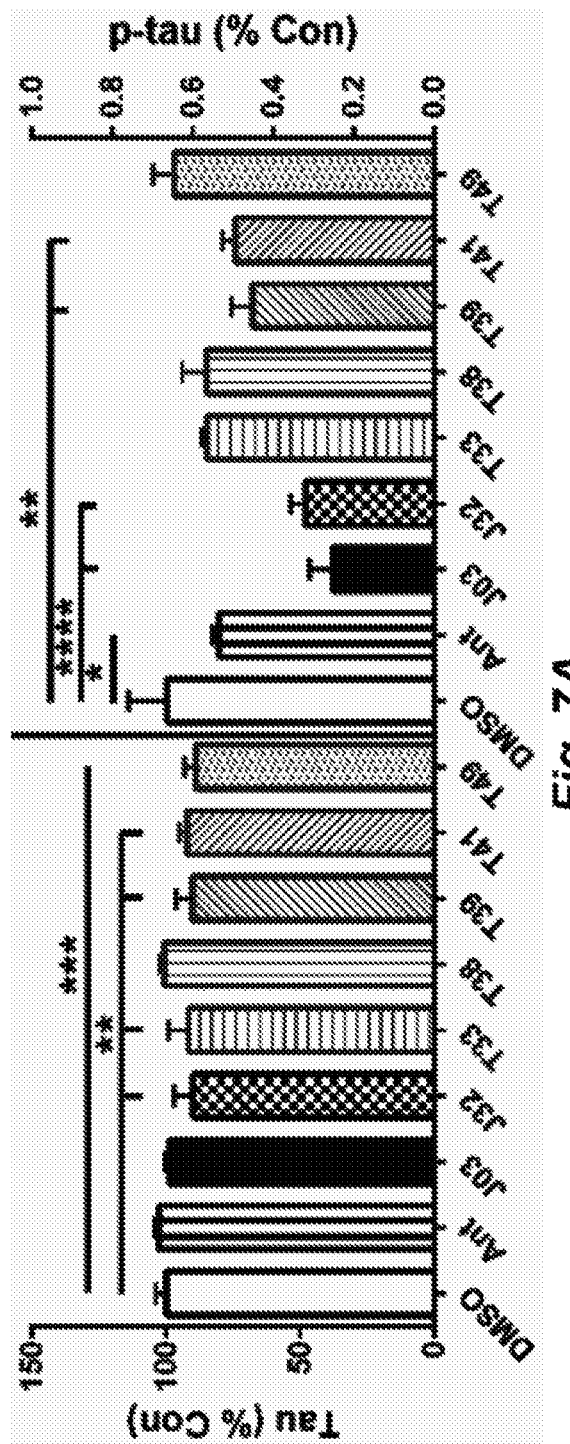
FIG. 7A shows tau and ptau levels.
Figure 7B:
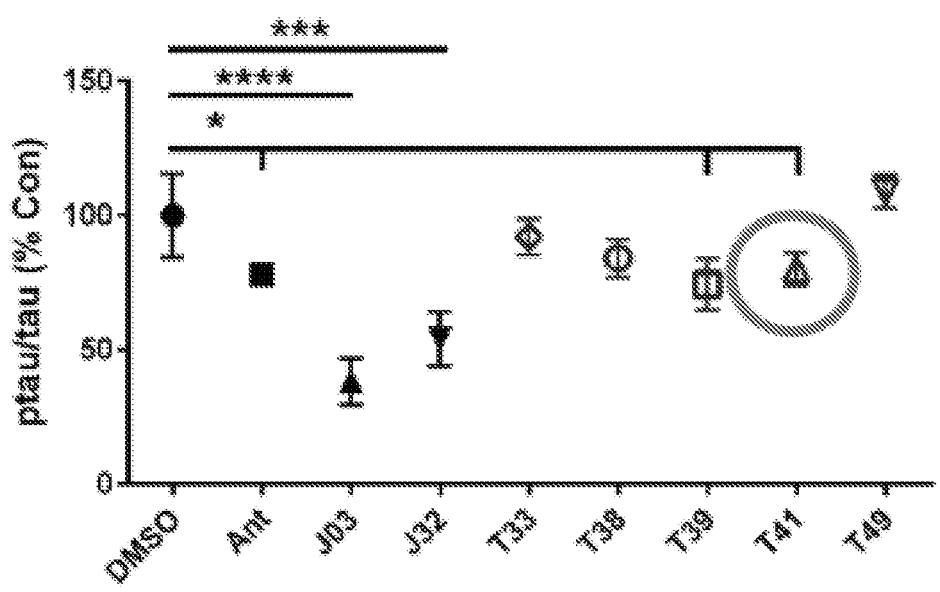
FIG. 7B shows ptau/tau concentration ins SH-SY5Y cells.

FIG. 7A shows tau and p-tau levels, and FIG. 7B shows p-tau/tau concentration ins SH-SY5Y cells. Human neuroblastoma SH-SY5Y cells were treated for 24 hours with 1 µM compound, and then tau and ptau levels were determined from cell lysates using AlphaLISA (FIG. 7A). T41, as well as J32. T33. and T39 slightly decreased total tau (left side of bar graph). and p-tau (right side of bar graph). As shown in FIG. 7B, while not as significant as the decrease with ligand-site inhibitors J03 and J32. T39, T41 (circled) significantly decreased the p-tau/tau ratio. Antalarmin (Ant), a known CRF1 antagonist, was used as a control.

CRF Challenge Assay

SH-SY5Y cells were plated at 50,000 cell/well into 96 well plates which contain compounds of interest at 50 nM. On the next day, cells were treated with 100 nM CRF for 3 days. Next, cells were lysed with RIPA buffer complemented with Halt Cocktail Inhibitors, and freeze/thaw 3 times. Cell lysate was assayed using AlphaLISA tau kit AL271C and for ptau detection we are comparing both antibodies: anti-Tau Phospho pSer202+Thr205 ("AT8") and anti-Tau Phospho Ser404 ("404")

Figure 8A:
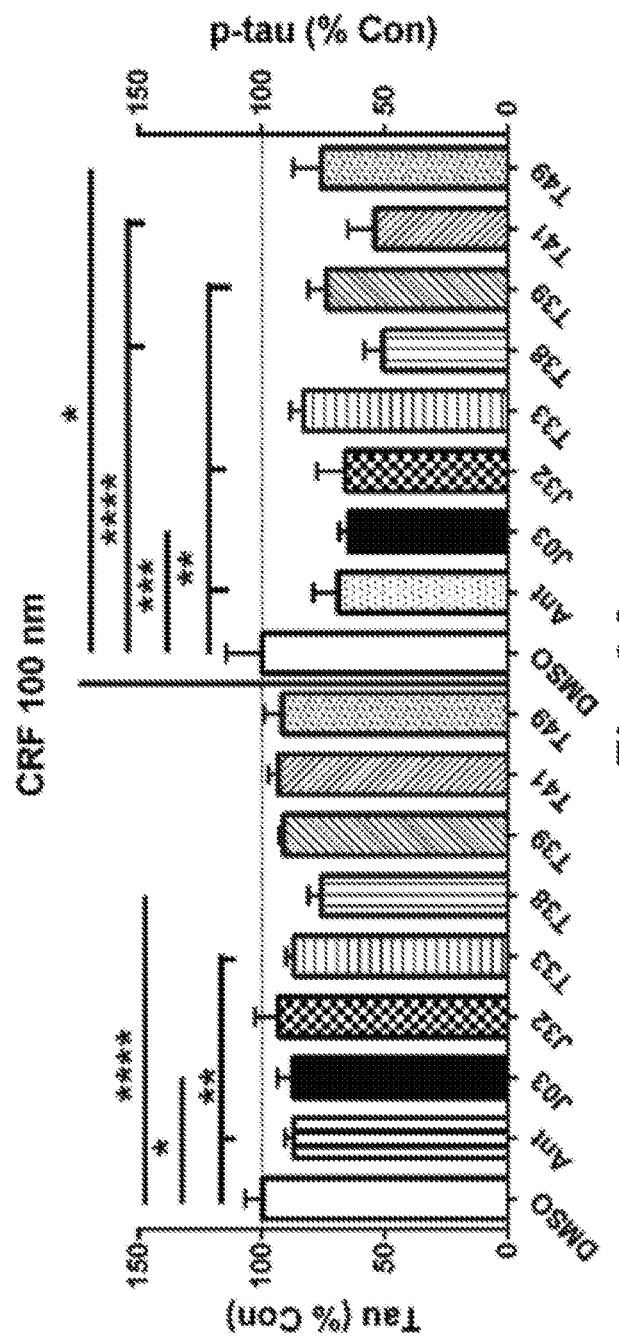
FIG. 8A shows tau and ptau levels.
Figure 8B:
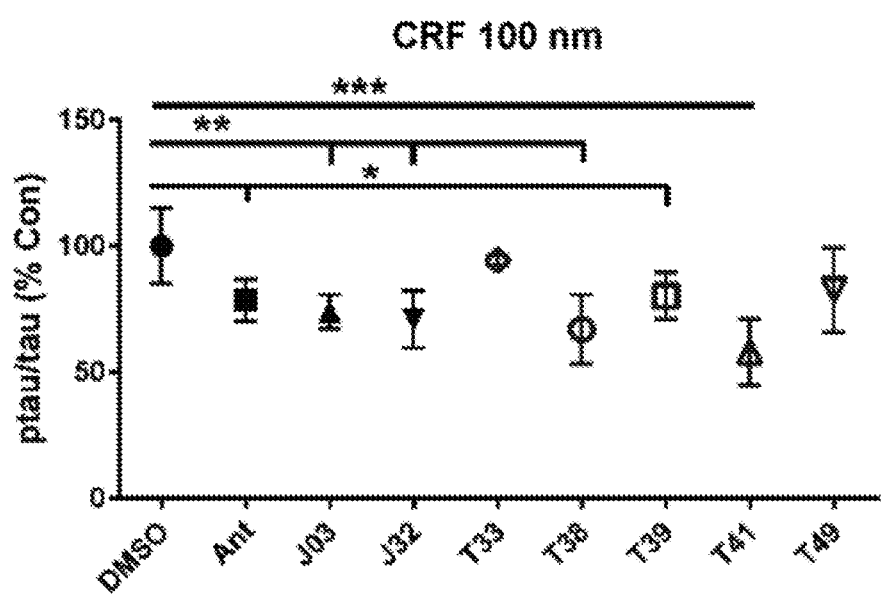
FIG. 8B shows ptau/tau concentration ins SH-SY5Y cells with CRF challenge.

FIG. 8A shows tau and p-tau levels, and FIG. 8B shows p-tau/tau concentration ins SH-SY5Y cells with CRF challenge. As shown in FIG. 8A, when both 1 µM compound and 100 nM CRF are present in SH-SY5Y cells for 24 hours, T41 does not lower tau but lowers p-tau with high significance, leading to a significant lowering of the p-tau/tau ratio (FIG. 8B).

Figure 9:
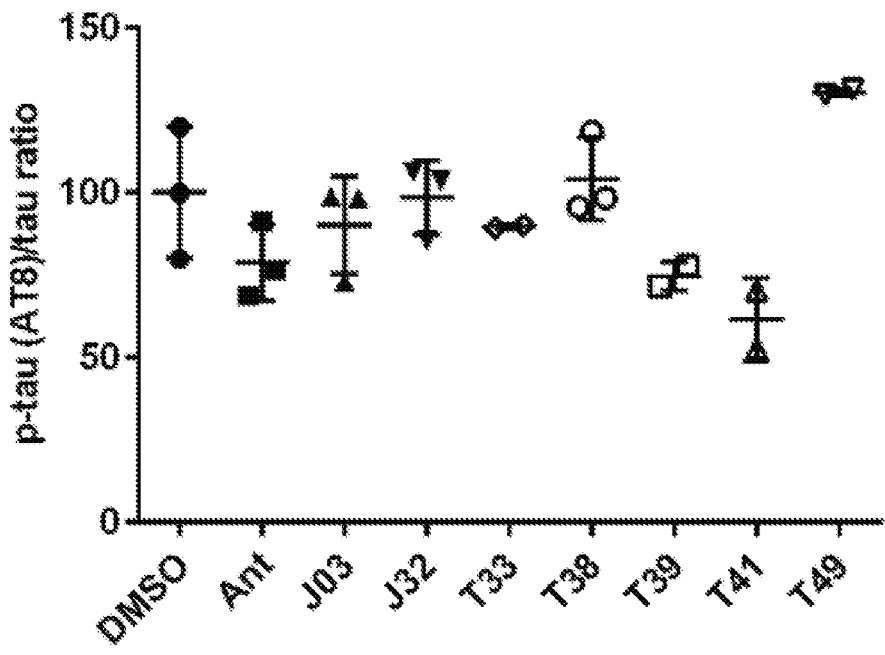
FIG. 9 shows ptau levels (top) and ptau/tau ratio (bottom) in SH-SY5Y cells when both 1 μM compound and 100 nM CRF are present in SH-SY5Y cells for 24 hours.
Figure 9:
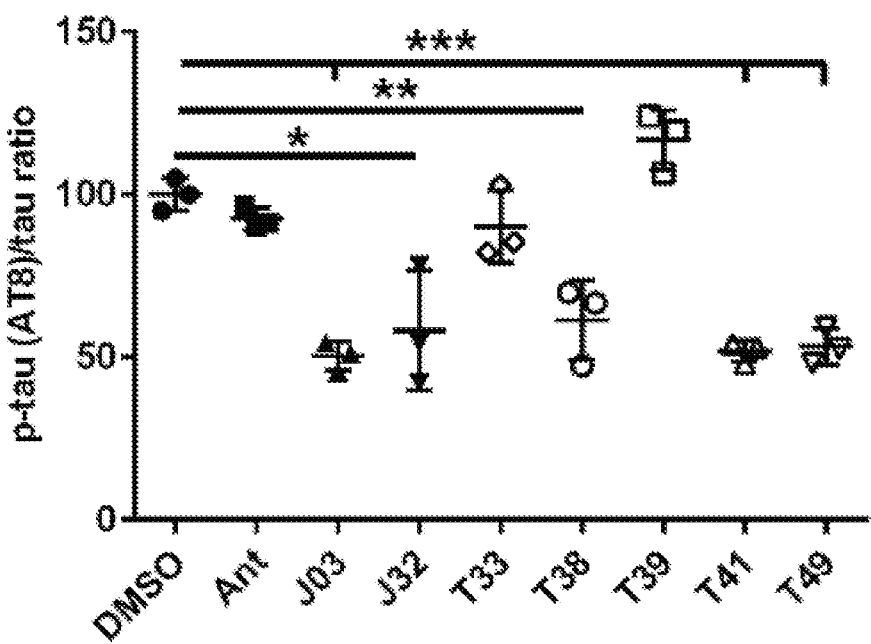

FIG. 9 shows p-tau/tau after 3 days with and without CRF1. T41 lowers the ptau/tau ratio in the absence (top) or presence (bottom) of 1 µM compound and (when present) 100 nM CRF after three days of treatment. Significance was not seen without CRF due to low N#, but is highly significant with CRF.

Figure 10:
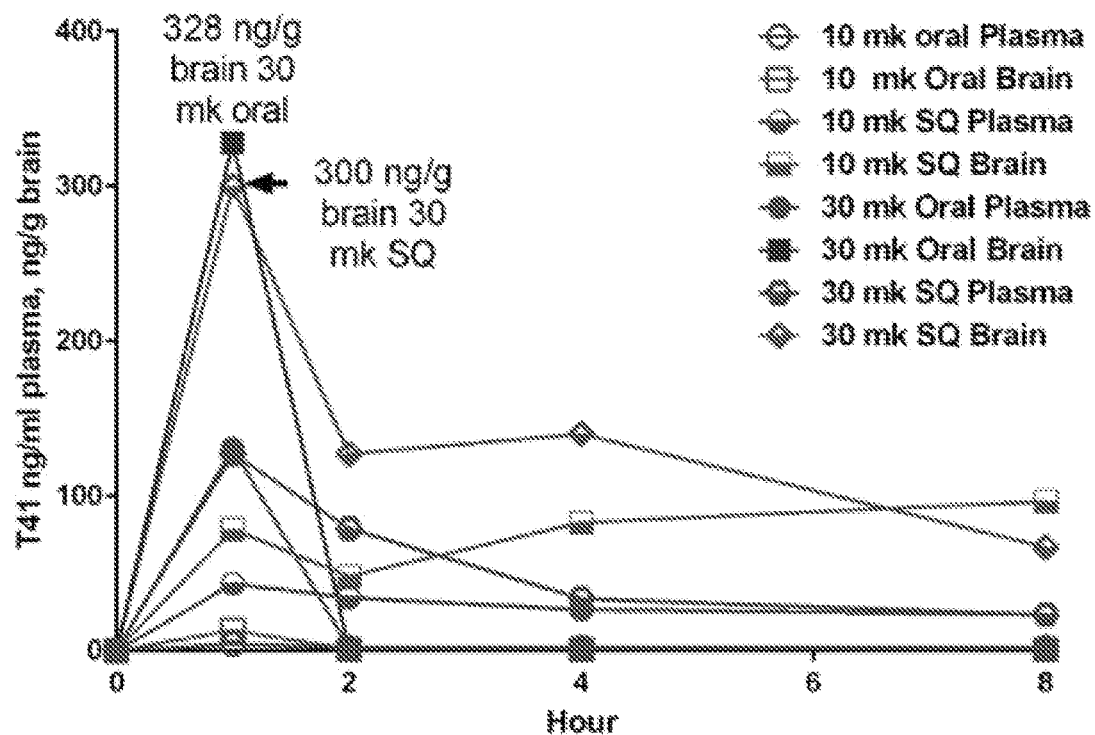
FIG. 10 illustrates in vivo pharmacokinetics after 3 days with (top) or without (bottom) T41.
Figure 10:
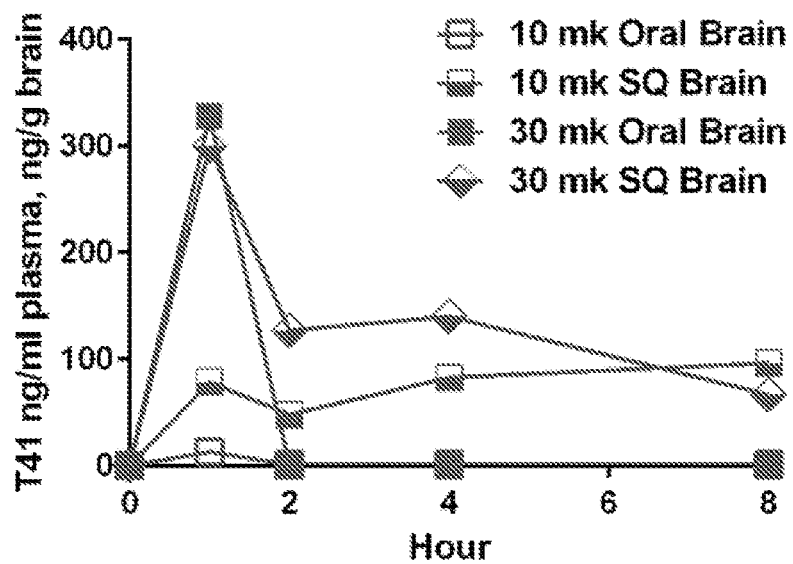

FIG. 10 illustrates in vivo pharmacokinetics for T41. As shown in the top panel, after oral or subcutaneous (SQ) dosing of adult mice at 10 or 30 mg/kg. and collection of plasma and brain at 1, 2, 4, and 8 hours, the brain/plasma ratio was ~3:2 for 30 mg/kg oral dosing and ~2:1 for 30 mg/kg SQ injection. The bottom panel shows that brain levels were higher at 30 than 10 mg/kg and higher with SQ injection than oral delivery as expected. After oral dosing at 30 mg/kg, brain levels peaked at 1 hour at 328 ng/g.

Example 4

Behavioral and Biochemical Effects of T41

The purpose of this study was to determine behavioral and biochemical effects of T41 (shown below and in FIG. 2) and its ability to prevent corticosterone (CTS)-induced increases in ptau in the "Goldstein" (GS) prnp-huAPPwt-YFP mouse model. Corticosterone is known to increase CRF, which then should bind the receptor and trigger increases in ptau with chronic CTS injection. Biochemistry included total tau, ptau, and sAPPα from combined entorhinal cortex and hippocampus. Levels of sAPPβ, βCTF, and Aβ1-4 and -42 are believed to be too low to detect in this model.

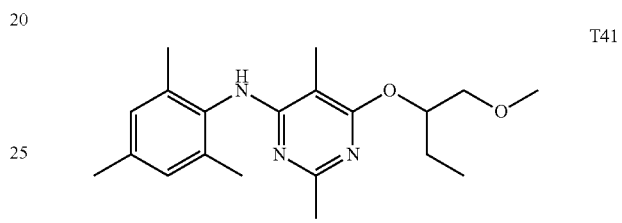

T41

Protocol and experimental parameters are shown in Table 6.

TABLE 6

Experimental parameters.

Dose of T41: 30 mkd
Route: Oral delivery 1 hour before injection of CTS.
Stock/vehicle/concentration: 25 mg/ml, 1:1 in 10% 2-hydroxypropyl-β-cyclodextrin made in 50% sucrose in water. Vehicle does not contain T41:
Duration: 21 days
Volume: 30 µL for 25 g mouse (36 µL for a 30 g mouse, etc.}
Aliquots: Daily aliquots for 7 days at a time were made in advance and stored at 4° C.
Weights: Weights were determined daily before dosing.
Dosing/timing: Once a day in am:
Dose of CTS: 30 mkd
Route: Subcutaneous injection 1 hour after oral delivery of T41.
Stock/vehicle/concentration: 4 mg/ml. 2-Hydroxypropyl-β-cyclodextrin (10% in 0.1µ filtered water). Vehicle control is [1:1, 2-Hydroxypropyl-β-cyclodextrin syrup (10% in 0.1µ filtered water).
Duration: 21 days
Volume: 187.5 µL for a 25 g mouse. Higher for heavier mice.
Aliquots: Daily aliquots for 7 days at a time were made in advance and stored at 4° C.
Weights: Weights were determined daily before dosing.
Dosing/timing: Once a day in am, 1 hour after T41 dosing.
Testing: Novel Object Recognition (NOR) and open field testing one week before start of the study and one day before end of the study.
Mice: NTg veh/veh (8), NTg veh/CTS (8), GS veh/veh (9), GS veh/CTS (10), and GS T41/CTS (10).
Anesthesia: Ketamine/xylazine, 2 hours after T41 or first vehicle injection of the last day. CTS or second vehicle not injected on the last day.
Perfusion: Saline perfusion at 5 ml/min.
Tissue collection: Plasma and brain for T41 levels, and combined hippocampus (Hip) and entorhinal cortex (ECX) from the right half brain for biochemistry.
Analysis: Total tau, ptau and the ratio; sAPPα, SirT1, and, if measurable, Aβ1-40 and/or 42.

Figure 11:
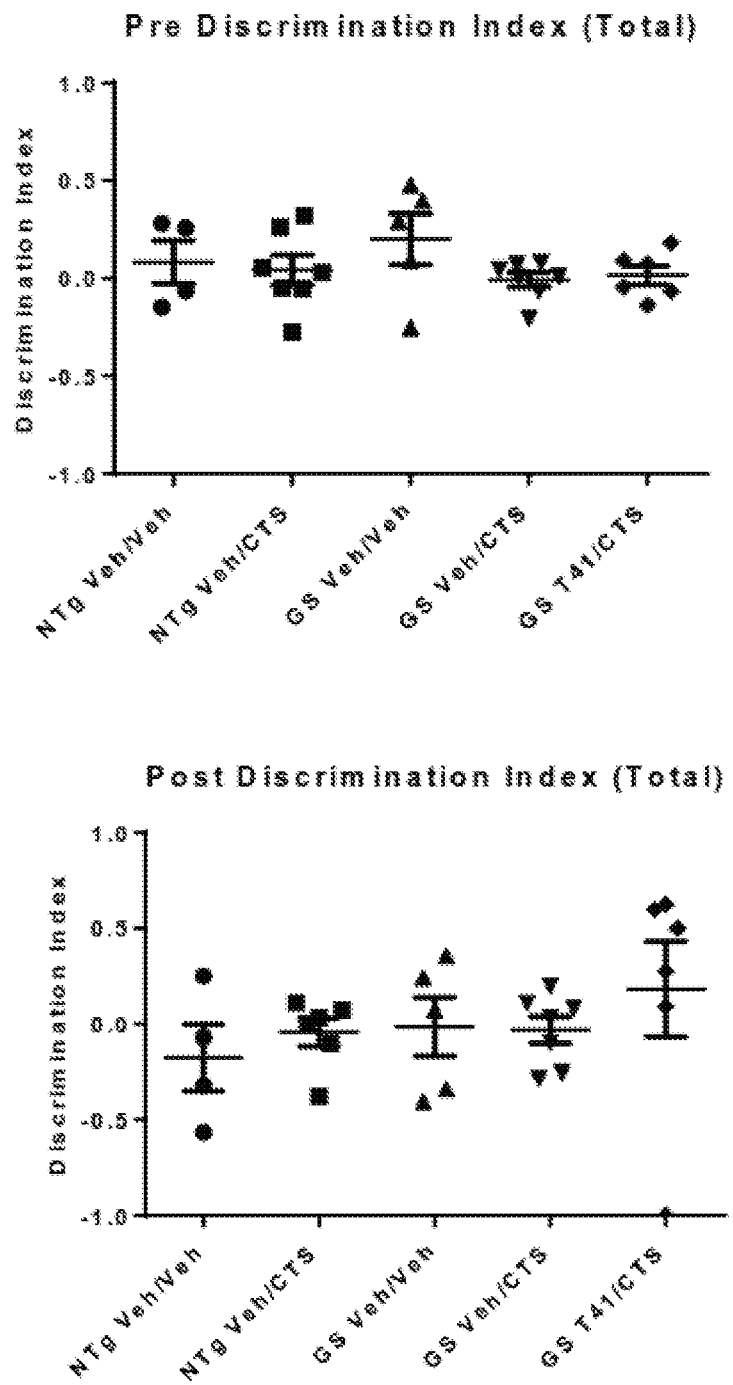
FIG. 11 illustrates discrimination (novelty preference) pre- (top) and post-study (bottom) and in response to treatment.

As shown in FIG. 11 there was no clear novelty preference either Pre- (top) or post- (bottom) study, suggesting modifications are needed in the testing paradigm. However, there was a promising trend toward some increased novelty preference in the T41-CTS mice post-study. Note that pre-study NTg Veh/Veh, and NTg Veh/CTS mice are all untreated and are considered as the same groups. Similarly, all GS mice are a group pre-study.

Figure 12:
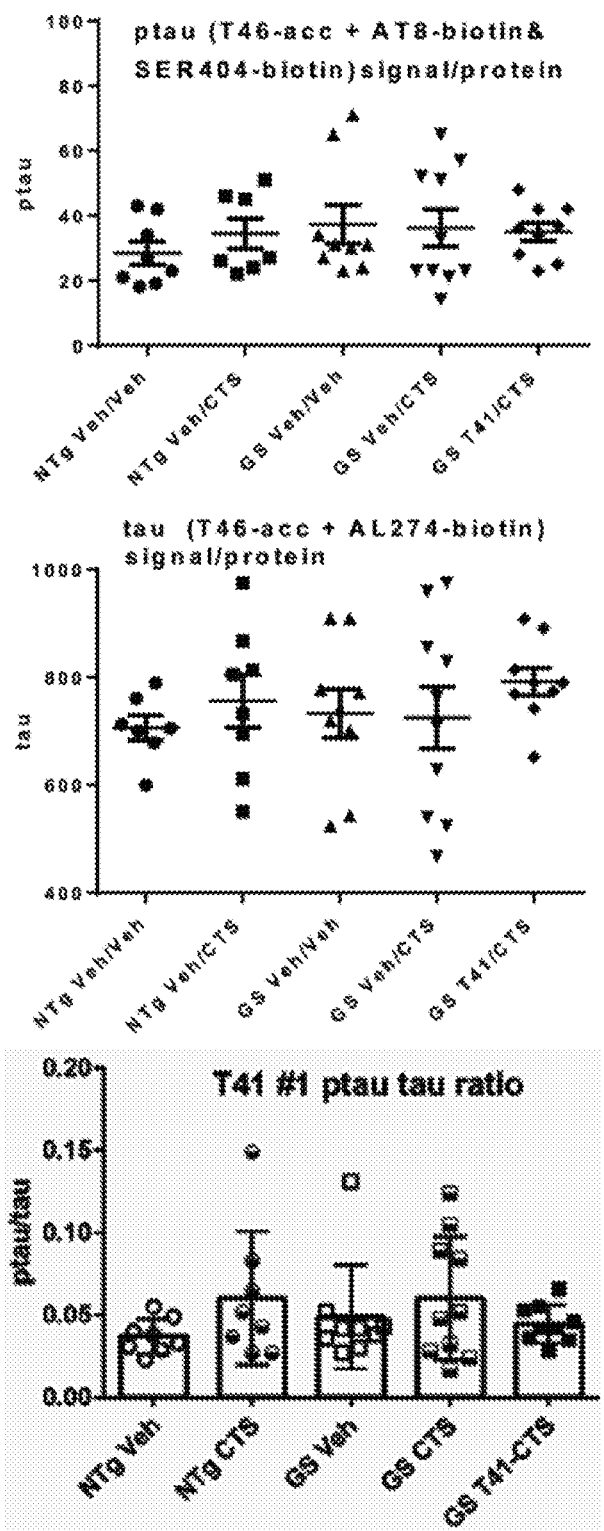
FIG. 12 illustrates in vivo ptau (top), total tau (middle) and ptau/total tau ratio (bottom).

There were no significant difference in ptau amongst groups (FIG. 12, top), although values for NTg Veh, GS Veh, GS CTS, and GS T41-CTS mice were all slightly higher than those for NTg Veh mice. There were also no significant differences in total tau amongst groups (FIG. 12, middle) and there was a lot of individual variation, but GS T41-CTS mice overall had the highest value. The ptau/tau ratio is calculated for each individual mouse, and while there were no significant differences amongst groups, there was a trend for CTS alone to increase the ratio, and for T41 pre-treatment to prevent that increase (FIG. 12, bottom). The T-41-induced reduction of the ratio did not reach statistical significance due to great variation in the CTS alone group and the N number.

Figure 13:
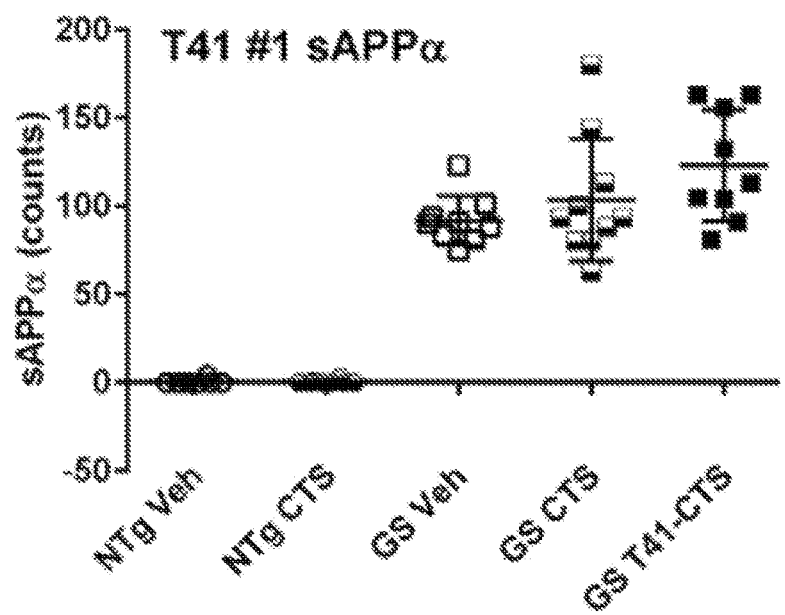
FIG. 13 shows sAPPα post-study after treatment with T41.

The assay used to detect sAPPα recognizes human sAPPα, therefore the signal is expected to be undetectable in NTg mice. There was little or no difference between GS Veh and GS CTS mice (FIG. 13). There was a trend toward an increase in sAPPα in T41-treated mice that was not statistically significant. Increases in sAPPα are correlated with improvement in cognition.

SUMMARY AND CONCLUSIONS

CTS injection was anticipated to increase the ptau/tau ratio, and T41 pre-treatment was predicted to prevent this increase. The trends for both were promising, and perhaps either BID injection of CTS or a higher dose will enhance the CTS effect, and allow any amelioration of this effect by T41 to be more readily seen. While the behavioral testing paradigm needs some adjustment to elicit the control novelty preference in NTg mice (it is also predicted that GS vehicle mice will show novelty preference), there was a promising trend for G5 T41-CTS mice to show some novelty preference at the end of the study. The decline in almost all movement and exploratory activity measures post-study suggest treatment and handling were stressful, and this stress should be reduced as the study purpose is to ascertain the effects of a stress pathway triggering chemical (CTS) and the amelioration of these effects by T41. Further stress adds individual variability.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound that is a CRFR1 receptor antagonist, wherein said compound is a compound according to the formula

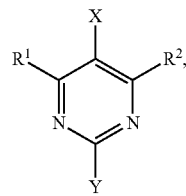

I or a pharmaceutically acceptable salt, enantiomer, or solvate thereof, wherein:

X and Y are independently selected from the group consisting of Me, H, $CF_3$, deuterated methyl, and halogen;

$R^1$ is an unsubstituted aminoaryl or a substituted aminoaryl, wherein the substituted aminoaryl is substituted with a substituent selected from the group consisting of $CH_3$, $OCH_3$, halogen, $CH_2NH_2$, CN, and $CR^8{}_3$, wherein $R^8$ is halogen; and $R^2$ is an unsubstituted branched alkoxide or a substituted branched alkoxide, wherein the substituted branched alkoxide is substituted with a substituent selected from the group consisting of $OCH_3$, $CH_3$, and $CH_2OH$, and wherein at least one of $R^1$ or $R^2$ is substituted with —$OCH_3$.

2. The compound of claim 1, wherein X and/or Y is $CH_3$.

3. The compound of claim 1, wherein $R^2$ is

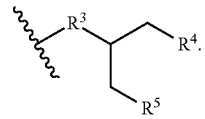

wherein:
$R^3$ is O,
$R^4$ is selected from the group consisting of $OCH_3$, $CH_3$, and $CH_2OH$; and
$R^5$ is selected from the group consisting of $CH_3$ and $OCH_3$.

4. The compound of claim 3, wherein $R^2$ is selected from the group consisting of

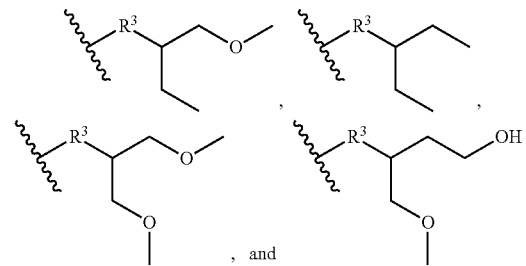

5. The compound of claim 1, wherein $R^1$ is

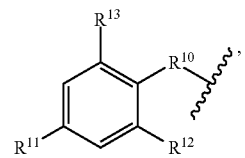

wherein
$R^{10}$ is NH;
$R^{11}$ is selected from the group consisting of H, $CH_3$, $OCH_3$, halogen, $CH_2NH_2$, CN, and $CR^8{}_3$ where $R^8$ is halogen;
$R^{12}$ is selected from the group consisting of H, $CH_3$, or halogen; and
$R^{13}$ is selected from the group consisting of $CH_3$, halogen, and $CR^9{}_3$ where $R^9$ is halogen.

6. The compound of claim 5, wherein R¹ is selected from the group consisting of
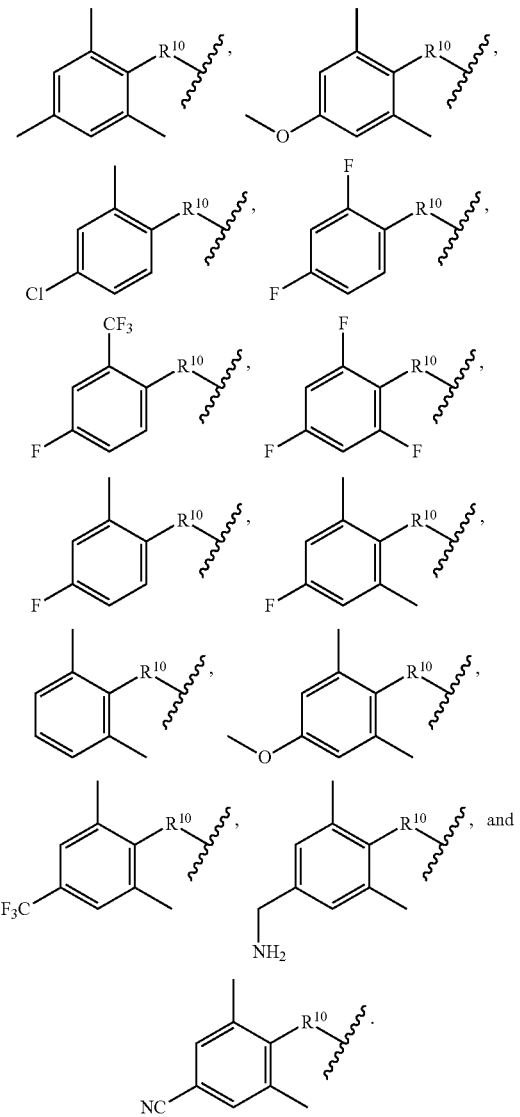
7. The compound of claim 1, wherein said compound is selected from the group consisting of
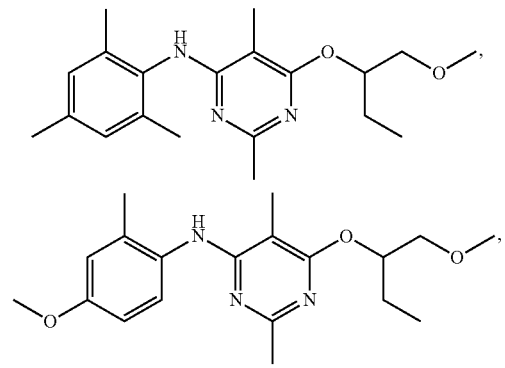
-continued
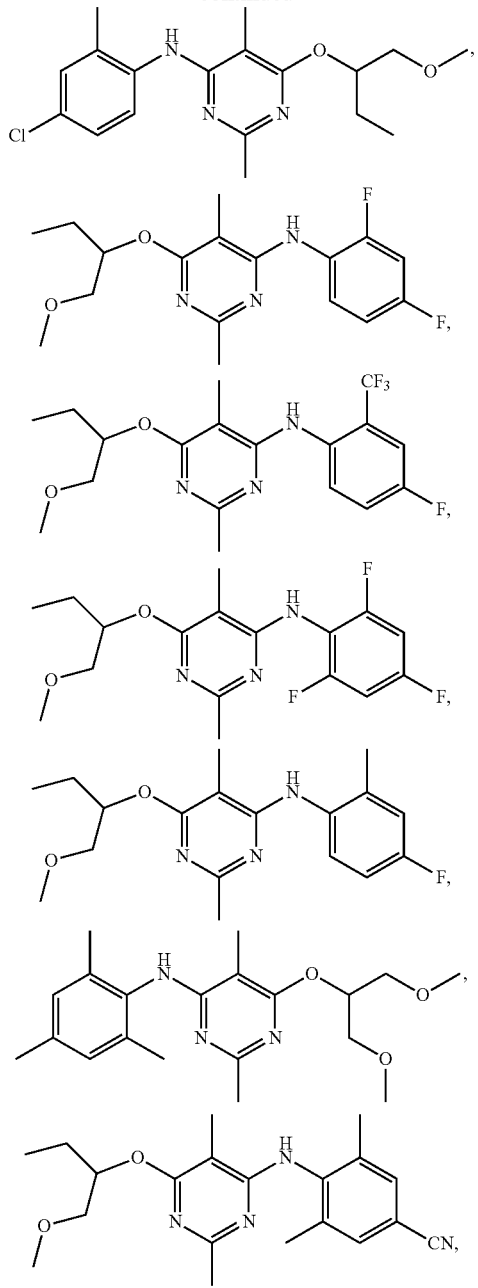
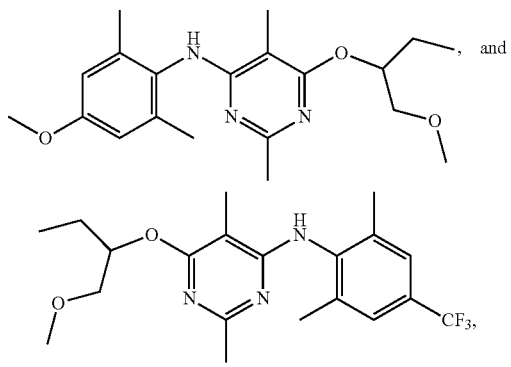
or a pharmaceutically acceptable salt, enantiomer, or solvate thereof.

8. A pharmaceutical formulation comprising the compound of claim 1, and a pharmaceutically acceptable carrier or excipient.

9. The compound of claim 1, wherein $R^1$ is the substituted aminoaryl.

10. The compound of claim 1, wherein $R^2$ is the substituted branched alkoxide.

11. The compound of claim 1, wherein said compound is

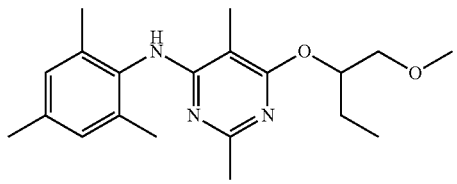

or a pharmaceutically acceptable salt or solvate thereof.

12. A pharmaceutical formulation comprising the compound of claim 11, and a pharmaceutically acceptable carrier or excipient.

13. The compound of claim 1, wherein said compound is an enantiomer of

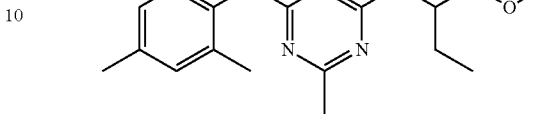

or a pharmaceutically acceptable salt or solvate thereof.

14. A pharmaceutical formulation comprising the compound of claim 13, and a pharmaceutically acceptable carrier or excipient.

* * * * *